US012297232B2

(12) United States Patent
Zhu et al.

(10) Patent No.: US 12,297,232 B2
(45) Date of Patent: May 13, 2025

(54) COMPOSITIONS AND METHODS FOR MUCOSAL VACCINATION AGAINST SARS-COV-2

(71) Applicant: University of Maryland, College Park, College Park, MD (US)

(72) Inventors: Xiaoping Zhu, Clarksville, MD (US); Weizhong Li, College Park, MD (US); Tao Wang, Ellicott City, MD (US)

(73) Assignee: University of Maryland, College Park, College Park, MD (US)

( * ) Notice: Subject to any disclaimer, the term of this patent is extended or adjusted under 35 U.S.C. 154(b) by 346 days.

(21) Appl. No.: 17/187,214

(22) Filed: Feb. 26, 2021

(65) Prior Publication Data

US 2022/0098242 A1 Mar. 31, 2022

Related U.S. Application Data

(60) Provisional application No. 62/981,873, filed on Feb. 26, 2020.

(51) Int. Cl.

| | |
|---|---|
| ***C07K 14/005*** | (2006.01) |
| ***A61K 39/00*** | (2006.01) |
| ***A61P 31/14*** | (2006.01) |

(52) U.S. Cl.

CPC ............ *C07K 14/005* (2013.01); *A61P 31/14* (2018.01); *A61K 39/00* (2013.01); *A61K 2039/543* (2013.01); *C07K 2319/30* (2013.01)

(58) Field of Classification Search

None

See application file for complete search history.

(56) References Cited

U.S. PATENT DOCUMENTS

| | | | | |
|---|---|---|---|---|
| 11,376,317 | B2 * | 7/2022 | Zhu | A61P 31/14 |
| 11,591,371 | B2 * | 2/2023 | Zhu | A61K 39/12 |
| 2007/0009523 | A1 * | 1/2007 | Presta | C07K 16/2887 435/7.1 |
| 2011/0086058 | A1 * | 4/2011 | Jiang | A61P 31/16 424/192.1 |
| 2013/0164286 | A1 | 6/2013 | Chou et al. | |
| 2015/0079121 | A1 | 3/2015 | Weiner et al. | |
| 2015/0125473 | A1 | 5/2015 | Burt et al. | |
| 2018/0244756 | A1 | 8/2018 | Graham et al. | |
| 2019/0060440 | A1 | 2/2019 | Zhu et al. | |
| 2019/0359655 | A1 | 11/2019 | Zhu et al. | |
| 2022/0401547 | A1 * | 12/2022 | Zhu | A61K 39/12 |
| 2023/0295240 | A1 * | 9/2023 | Zhu | A61K 39/145 424/206.1 |

FOREIGN PATENT DOCUMENTS

| | | | | |
|---|---|---|---|---|
| WO | WO-2019/046864 A1 | | 3/2019 | |
| WO | WO-2019046859 A1 | * | 3/2019 | A61K 47/6803 |

OTHER PUBLICATIONS

Wrapp et al, Science 367, 1260-1263 (2020). (Year: 2020).*

Written Opinion and Search Report issued Jul. 1, 2021 by the International Search Report for Application No. PCT/US2021/020099 filed on Feb. 26, 2021 (Applicant: University of Maryland) (10 pages).

Walls et al. "Structure, function and antigenicity of the SARS-CoV-2 spike glycoprotein" bioRxiv, Feb. 20, 2020; Cell 180, 281-292, Apr. 16, 2020.

U.S. Appl. No. 62/981,873, filed Feb. 26, 2020, Xiaoping Zhu (University of Maryland).

PCT, PCT/US2012/020099 (WO/2021174128), Feb. 26, 2021, (Sep. 2, 2021), Xiaoping Zhu (University of Maryland).

U.S. Appl. No. 18/517,578, filed Nov. 22, 2023, Zhu.

U.S. Appl. No. 16/373,272, filed Apr. 2, 2019, Zhu.

U.S. Appl. No. 17/831,928, filed Jun. 3, 2022, Zhu.

Allie SR, Randall TD. Pulmonary immunity to viruses. Clin Sci (Lond). Jun. 30, 2017;131(14):1737-1762.

Bai Y, et al.(2011) Intracellular neutralization of viral infection in polarized epithelial cells by neonatal Fc receptor (FcRn)-mediated IgG transport. Proc Natl Acad Sci U S A. 108:18406-11.

Barría MI, et al (2013) Localized mucosal response to intranasal live attenuated influenza vaccine in adults. J Infect Dis. 207:115-24.

Berneman A, Belec L, Fischetti VA, Bouvet JP. 1998. The specificity patterns of human immunoglobulin G antibodies in serum differ from those in autologous secretions. Infect Immun. 66:4163-4168.

Boukhvalova MS, Blanco JC. 2013. The cotton rat Sigmodon hispidus model of respiratory syncytial virus infection. Curr Top Microbiol Immunol. 372:347-58.

Brokstad KA (2002) Parenteral vaccination against influenza does not induce a local antigen-specific immune response in the nasal mucosa. J Infect Dis. 185:878-84.

Brown DM, et al. (2012) Multifunctional CD4 cells expressing gamma interferon and perforin mediate protection against lethal influenza virus infection. J Virol. 86:6792-803.

(Continued)

*Primary Examiner* — Anand U Desai
*Assistant Examiner* — Cheom-Gil Cheong
(74) *Attorney, Agent, or Firm* — BALLARD SPAHR LLP

(57) ABSTRACT

Disclosed are peptides comprising a monomeric Fc fragment of an immunoglobulin recognized by a FcRn; SARS-COV-2 antigen; and a trimerization domain. Disclosed are peptide complexes comprising three peptides, wherein each of the three peptides comprises a monomeric Fc fragment of an immunoglobulin recognized by a FcRn; SARS-COV-2 antigen; and a trimerization domain. Disclosed are compositions comprising any of the disclosed peptides or peptide complexes. Disclosed are methods for eliciting a protective immune response against SARS-COV-2 comprising administering to a subject an effective amount of one or more of the compositions disclosed herein. Disclosed are methods of treating a subject exposed to SARS-COV-2 or at risk of being exposed to SARS-COV-2 comprising administering to a subject an effective amount of one or more of the compositions disclosed herein.

16 Claims, 10 Drawing Sheets

Specification includes a Sequence Listing.

(56) References Cited

OTHER PUBLICATIONS

Castilow EM, Varga SM. 2008. Overcoming T cell-mediated immunopathology to achieve safe RSV vaccination. Future Virol. 3:445-454.
Chiu C, Openshaw PJ (2015) Antiviral B cell and T cell immunity in the lungs. Nat Immunol. 16:18-26.
Cullen LM, Blanco JC, Morrison TG. 2015. Cotton rat immune responses to virus-like particles containing the pre-fusion form of respiratory syncytial virus fusion protein. J Transl Med. 13:350.
Dickinson BL, et al. (1999) Bidirectional FcRn-dependent IgG transport in a polarized human intestinal epithelial cell line. J Clin Invest. 104:903-11.
Duncan AR, Winter G (1988) The binding site for C1q on IgG. Nature. 332:738-40.
Ekiert DC, et al. (2011) A highly conserved neutralizing epitope on group 2 influenza A viruses. Science. 333:843-50.
Erbelding EJ, et al. (2018) A Universal Influenza Vaccine: The Strategic Plan for the National Institute of Allergy and Infectious Diseases. J Infect Dis. 218:347-54.
Ermler ME, et al. (2017) Chimeric Hemagglutinin Constructs Induce Broad Protection against Influenza B Virus Challenge in the Mouse Model. J Virol. 91: pii: e00286-17.
Frey A, Di Canzio J, Zurakowski D (1998) A statistically defined endpoint titer determination method for immunoassays. J. Immunol. Methods, 221:35-41.
Friesen RH, et al. (2014) A common solution to group 2 influenza virus neutralization. Proc Natl Acad Sci U S A. Jan. 7, 2014;111(1):445-50.
Garg R, Latimer L, Simko E, Gerdts V, Potter A, van den Hurk Sv. Induction of mucosal immunity and protection by intranasal immunization with a respiratory syncytial virus subunit vaccine formulation. J Gen Virol. Feb. 2014;95(Pt 2):301-6.
Garg R, Theaker M, Martinez EC, van Drunen Littel-van den Hurk S. A single intranasal immunization with a subunit vaccine formulation induces higher mucosal IgA production than live respiratory syncytial virus. Virology. Dec. 2016;499:288-297.
Gebril A, Alsaadi M, Acevedo R, Mullen AB, Ferro VA. 2012. Optimizing efficacy of mucosal vaccines. Expert Rev Vaccines. 11:1139-55.
Graham BS, Modjarrad K, Mclellan JS. 2015. Novel antigens for RSV vaccines. Curr Opin Immunol. 35:30-8.
Hirst GK (1942) The Quantitative Determination of Influenza Virus and Abs by Means of Red Cell Agglutination. J. Exp. Med. 75:49-64.
Hodge LM, et al. (2001) Immunoglobulin A (IgA) responses and IgE-associated inflammation along the respiratory tract after mucosal but not systemic immunization. Infect Immun. 69:2328-38.
Holmgren J, Svennerholm AM. 2012. Vaccines against mucosal infections. Curr Opin Immunol. 24:343-53.
Houser K, Subbarao K (2015) Influenza vaccines: challenges and solutions. Cell Host Microbe. 17:295-300.
Iho S, Maeyama J, Suzuki F (2015) CpG oligodeoxynucleotides as mucosal adjuvants. Hum Vaccin Immunother. 11:755-60.
Iijima N, Iwasaki A (2015) Tissue instruction for migration and retention of TRM cells. Trends Immunol. 36:556-64.
Iwasaki A. (2016) Exploiting Mucosal Immunity for Antiviral Vaccines. Annu Rev Immunol. 34:575-608.
Iwasaki A, Foxman EF, Molony RD (2017) Early local immune defenses in the respiratory tract. Nat Rev Immunol. 17:7-20.
Johnson TR, Rangel D, Graham BS, Brough DE, Gall JG. Genetic vaccine for respiratory syncytial virus provides protection without disease potentiation. Mol Ther. Jan. 2014;22(1):196-205.
Johnson TR, Rao S, Seder RA, Chen M, Graham BS. 2009. TLR9 agonist, but not TLR7/8, functions as an adjuvant to diminish FI-RSV vaccine-enhanced disease, while either agonist used as therapy during primary RSV infection increases disease severity. Vaccine. 27:3045-52.
Joyce MG, et al. 2016. Iterative structure-based improvement of a fusion-glycoprotein vaccine against RSV. Nat Struct Mol Biol. 23:811-20.
Kim JK, Tsen MF, Ghetie V, Ward ES (1994) Localization of the site of the murine IgG1 molecule that is involved in binding to the murine intestinal Fc receptor. Eur J Immunol. 24:2429-34.
Kinnear E, Lambert L, McDonald JU, Cheeseman HM, Caproni LJ, Tregoning JS. Airway T cells protect against RSV infection in the absence of antibody. Mucosal Immunol. May 24, 2017.
Ko SY, et al. (2014) Enhanced neonatal Fc receptor function improves protection against primate SHIV infection. Nature. 514:642-5.
Krammer F, et al. (2012) A carboxy-terminal trimerization domain stabilizes conformational epitopes on the stalk domain of soluble recombinant hemagglutinin substrates. PLoS One. 7:e43603.
Krammer F, Pica N, Hai R, Margine I, Palese P (2013) Chimeric hemagglutinin influenza virus vaccine constructs elicit broadly protective stalk-specific Abs. J Virol. 87:6542-50.
Krammer F, et al. (2014) Assessment of influenza virus hemagglutinin stalk-based immunity in ferrets. J Virol. 88:3432-42.
Krammer F, Palese P. (2015) Advances in the development of influenza virus vaccines. Nat Rev Drug Discov. 14:167-82.
Krarup A, et al., 2015. A highly stable prefusion Rsv F vaccine derived from structural analysis of the fusion mechanism. Nat Commun. 6:8143.
Laidlaw BJ, et al. (2014) CD4+ T cell help guides formation of CD103+ lung-resident memory CD8+ T cells during influenza viral infection. Immunity. 41:633-45.
Liang et al., Enhanced Neutralizing Antibody Response Induced by Respiratory Syncytial Virus Prefusion F Protein Expressed by a Vaccine Candidate. J Virol. 2015, vol. 89(18), p. 9499-510.
Lu et al. A neonatal Fc receptor-targeted mucosal vaccine strategy effectively induces HIV-1 antigen-specific immunity to genital infection. J Virol. Oct. 2011. pp. 10542-10553, vol. 85, No. 20.
McGhee JR. 2011. A mucosal gateway for vaccines. Nat Biotechnol. 29:136-8.
McLellan et al., Structure-Based Design of a Fusion Glycoprotein Vaccine for Respiratory Syncytial Virus. Science. 2013, vol. 342(6158), pp. 592-598.
McMaster SR, Wilson JJ, Wang H, Kohlmeier JE (2015) Airway-Resident Memory CD8 T Cells Provide Antigen-Specific Protection against Respiratory Virus Challenge through Rapid IFN-γ Production. J Immunol. 195:203-9.
McMaster SR, et al. (2018) Pulmonary antigen encounter regulates the establishment of tissue-resident CD8 memory T cells in the lung airways and parenchyma. Mucosal Immunol. 11:1071-8.
Major D, et al. (2015) Intranasal vaccination with a plant-derived H5 HA vaccine protects mice and ferrets against highly pathogenic avian influenza virus challenge. Hum Vaccin Immunother. 11:1235-43.
Margine I, et al. (2013) Hemagglutinin stalk-based universal vaccine constructs protect against group 2 influenza A viruses. J Virol. 87:10435-46.
Minne A, et al. (2007) The delivery site of a monovalent influenza vaccine within the respiratory tract impacts on the immune response. Immunology. 122:316-25.
Moghaddam A, Olszewska W, Wang B, Tregoning JS, Helson R, Sattentau QJ, Openshaw PJ. 2006. A potential molecular mechanism for hypersensitivity caused by formalin-inactivated vaccines. Nat Med. 12:905-7.
Morabito KM, Ruckwardt TR, Redwood AJ, Moin SM, Price DA, Graham BS. 2017. Intranasal administration of RSV antigen-expressing MCMV elicits robust tissue-resident effector and effector memory CD8+ T cells in the lung. Mucosal Immunol. 10:545-554.
Mueller SN, Gebhardt T, Carbone FR, Heath WR (2013) Memory T cell subsets, migration patterns, and tissue residence. Annu Rev Immunol. 31:137-61.
Muszkat M, et al. (2003) Local and systemic immune response in nursing-home elderly following intranasal or intramuscular immunization with inactivated influenza vaccine. Vaccine. 21:1180-6.
Neutra MR, Kozlowski PA. 2006. Mucosal vaccines: the promise and the challenge. Nat Rev Immunol. 6:148-58.

(56) References Cited

OTHER PUBLICATIONS

Ngwuta JO, et al. 2015. Prefusion F-specific antibodies determine the magnitude of RSV neutralizing activity in human sera. Sci Transl Med. 7:309ra162.
Oh S, et al. (2009) Neutralizing monoclonal Abs to different clades of Influenza A H5N1 viruses. J Virol Methods. 157:161-7.
Openshaw PJ, Tregoning JS. 2005. Immune responses and disease enhancement during respiratory syncytial virus infection. Clin Microbiol Rev. 18:541-55.
Oshansky CM, Zhang W, Moore E, Tripp RA. 2009. The host response and molecular pathogenesis associated with respiratory syncytial virus infection. Future Microbiol. 4:279-97.
Palomo C, et al. 2016. Influence of Respiratory Syncytial Virus F Glycoprotein Conformation on Induction of Protective Immune Responses. J Virol. 90:5485-98.
Passmore C, et al. Intranasal immunization with W 80 5EC adjuvanted recombinant RSV rF-ptn enhances clearance of respiratory syncytial virus in a mouse model. Hum Vaccin Immunother. 2014;10(3):615-22.
Pavot V, Rochereau N, Genin C, Verrier B, Paul S. 2012. New insights in mucosal vaccine development. Vaccine. 30:142-54.
Pierantoni A, et al. Mucosal delivery of a vectored RSV vaccine is safe and elicits protective immunity in rodents and nonhuman primates. Mol Ther Methods Clin Dev. May 20, 2015;2:15018.
Pizzolla A, et al. (2017) Resident memory CD8+T cells in the upper respiratory tract prevent pulmonary influenza virus infection. Sci Immunol. 2. pii: eaam6970.
Qiao SW, et al. (2008) Dependence of Ab mediated presentation of antigen on FcRn. Proc Natl Acad Sci U S A. 105:9337-42.
Rath et al., Regulation of immune responses by the neonatal Fc receptor and its therapeutic implications. Front Immunol. 2015, vol. 5:664.
Renegar KB, Small PA Jr, Boykins LG, Wright PF (2004) Role of IgA versus IgG in the control of influenza viral infection in the murine respiratory tract. J Immunol. 173:1978-86.
Ruan et al., Suppressive effect of locally produced interleukin-10 on respiratory syncytial virus infection. Immunology. 2001, vol. 104(3), p. 355-60.
Sallusto F, Lanzavecchia A, Araki K, Ahmed R (2010) From vaccines to memory and back. Immunity. 33:451-63.
Slifka MK, Antia R, Whitmire JK, Ahmed R (1998) Humoral immunity due to long-lived plasma cells. Immunity. 8:363-72.
Slütter B, et al. (2017) Dynamics of influenza-induced lung-resident memory T cells underlie waning heterosubtypic immunity. Sci Immunol. 2. pii: eaag2031.
Spiekermann GM, et al. (2002) Receptor-mediated immunoglobulin G transport across mucosal barriers in adult life: functional expression of FcRn in the mammalian lung. J Exp Med. 196:303-10.
Tan GS, et al. (2012) A pan-H1 anti-hemagglutinin monoclonal Ab with potent broad-spectrum efficacy in vivo. J Virol. 86:6179-88.
Turner DL, Farber DL (2014) Mucosal resident memory CD4 T cells in protection and immunopathology. Front Immunol. 14;5:331.
Van Riet E, Ainai A, Suzuki T, Hasegawa H (2012) Mucosal IgA responses in influenza virus infections; thoughts for vaccine design. Vaccine. 30:5893-900.
Vaughn DE, Bjorkman PJ. (1998) Structural basis of pH-dependent Ab binding by the neonatal Fc receptor. Structure. 6:63-73.
Vissers M, Ahout IML, de Jonge MI, Ferwerda G. 2016. Mucosal IgG levels correlate better with respiratory syncytial virus load and inflammation than plasma IgG levels. Clin Vaccine Immunol 23:243-245.
Weldon WC, et al. (2010) Enhanced immunogenicity of stabilized trimeric soluble influenza hemagglutinin. PLoS One. 5. pii: e12466.
Wu T, et al. (2014) Lung-resident memory CD8 T cells (TRM) are indispensable for optimal cross-protection against pulmonary virus infection. J Leukoc Biol. 95:215-24.
Yang K, Varga SM. 2014. Mucosal vaccines against respiratory syncytial virus. Curr Opin Virol. 6:78-84.
Yoshida M, et al. (2006) Neonatal Fc receptor for IgG regulates mucosal immune responses to luminal bacteria. J Clin Invest. 116:2142-2151.
Zens KD, Chen JK, Farber DL (2016) Vaccine-generated lung tissue-resident memory T cells provide heterosubtypic protection to influenza infection. JCI Insight. 1. pii: e85832.
Zhirnov OP, Ikizler MR, Wright PF (2002) Cleavage of influenza a virus hemagglutinin in human respiratory epithelium is cell associated and sensitive to exogenous antiproteases. J Virol. 76:8682-9.
International Search Report and Written Opinion were mailed on Feb. 22, 2019 by the International Searching Authority for International Application No. PCT/US2018/055896, filed on Oct. 15, 2018 and published as WO 2019/046864 on Apr. 4, 2019 (Applicant-Xiaoping Zhu) (14 Pages).
Afkhami, S. et al. Respiratory mucosal delivery of next-generation COVID-19 vaccine provides robust protection against both ancestral and variant strains of SARS-CoV-2. *Cell* 185, 896-915.e19 (2022).
Al-Aly Z, Bowe B, & Xie Y. Long COVID after breakthrough SARS-CoV-2 infection. *Nat. Med.* 28, 1461-1467 (2022).
Allie, S. R et al. The establishment of resident memory B cells in the lung requires local antigen encounter. Nat. Immunol. 20, 97-108 (2019).
Andrews, M. G. et al. Tropism of SARS-CoV-2 for human cortical astrocytes. *Proc. Natl. Acad. Sci. USA.* 119(30), pp. 1-12, e2122236119 (2022).
Baker, K. et al. Neonatal Fc receptor for IgG (FcRn) regulates cross-presentation of IgG immune complexes by CD8-CD11b+ dendritic cells. *Proc. Natl. Acad. Sci. U S A.* 108(24:9927-9932 (2011).
Bauer, L. et al. The neuroinvasiveness, neurotropism, and neurovirulence of SARS-CoV-2. *Trends Neurosci.* 45(5):358-368 (2022).
Chandrashekar, A. et al. Vaccine protection against the SARS-CoV-2 Omicron variant in macaques. *Cell* 185, 1549-1555.e11 (2022).
Dan, J. M. et al. Immunological memory to SARS-CoV-2 assessed for up to 8 months after infection. *Science* 371, eabf4063 (2021).
Dekkers, G. et al. Affinity of human IgG subclasses to mouse Fc gamma receptors. *MAbs* 9, 767-773 (2017).
Du, L. et al. The spike protein of SARS-CoV—a target for vaccine and therapeutic development. *Nat. Rev. Microbiol.* 7, 226-236 (2009).
Fischer, H. & Widdicombe, J. H. Mechanisms of acid and base secretion by the airway epithelium. *J. Membr. Biol.* 211, 139-150 (2006).
Fröberg, J et al. SARS-CoV-2 mucosal antibody development and persistence and their relation to viral load and COVID-19 symptoms. *Nat. Commun.* 12, 5621 (2021).
Golden, J. W. et al. Hamsters Expressing Human Angiotensin-Converting Enzyme 2 Develop Severe Disease following Exposure to SARS-CoV-2. *mBio* 13, e0290621(2022).
Grau-Expósito, J. et al. Peripheral and lung resident memory T cell responses against SARS-CoV-2. *Nat. Commun.* 12, 3010 (2021).
Hassan, A. O. et al. A Single-Dose Intranasal ChAd Vaccine Protects Upper and Lower Respiratory Tracts against SARS-CoV-2. *Cell* 183, 169-184, e13 (2020).
Hartwell, B. L. et al. Intranasal vaccination with lipid-conjugated immunogens promotes antigen transmucosal uptake to drive mucosal and systemic immunity. *Sci. Transl. Med.* 14(654), pp. 1-14, eabn1413 (2022).
He, W. et al. FcRn-mediated antibody transport across epithelial cells revealed by electron tomography. *Nature* 455, 542-546 (2008).
Hou, Y. J. et al. SARS-CoV-2 reverse genetics reveals a variable infection gradient in the respiratory tract. *Cell* 182, 429-446, e14 (2020).
Hunter, P. Viral diseases and the brain: Long COVID puts the spotlight on how viral infections affect the brain. *EMBO Rep.* 23, e54342 (2022).
Idusogie, E, E, et al. Mapping of the C1q binding site on rituxan, a chimeric antibody with a human IgG1 Fc. *J. Immunol.* 164, 4178-4184 (2000).
Jeyanathan, M. et al. Immunological considerations for COVID-19 vaccine strategies. *Nat. Rev. Immunol.* 20, 615-632 (2020).

(56) References Cited

OTHER PUBLICATIONS

Kubo, T. et al. CpG-DNA enhances the tight junction integrity of the bronchial epithelial cell barrier. *J. Allergy. Clin. Immunol.* 136, 1413-6.e1-8 (2015).
Letarov, A.V., Londer, et al., The carboxy-terminal domain initiates trimerization of bacteriophage T4 fibritin. *Biochemistry* 64(7), 817-823 (1999).
Li, Z. et al. Transfer of IgG in the female genital tract by MHC class I-related neonatal Fc receptor (FcRn) confers protective immunity to vaginal infection. *Proc. Natl. Acad. Sci. U S A.* 108, 4388-4393 (2011).
Liu, X. et al. The neonatal FcR-mediated presentation of immune-complexed antigen is associated with endosomal and phagosomal pH and antigen stability in macrophages and dendritic cells. *J. Immunol.* 186(8), 4674-4686 (2011).
Lu, L. et al. A neonatal Fc receptor-targeted mucosal vaccine strategy effectively induces HIV-1 antigen-specific immunity to genital infection. *J. Virol.* 85(20, 10542-10553 (2011).
Lipsitch, M., Krammer, F., Regev-Yochay, G., Lustig, Y., & Balicer, R.D. SARS-CoV-2 breakthrough infections in vaccinated individuals: measurement, causes and impact. *Nat. Rev. Immunol.* 22, 57-65 (2022).
Lund, F. E. & Randall, T. D. Scent of a vaccine. *Science* 373, 397-399 (2021).
Mao, T. et al. Unadjuvanted intranasal spike vaccine elicits protective mucosal immunity against sarbecoviruses. Science 378(872), pp. 1-14, eabo2523 (2022).
Meinhardt, J. et al. Olfactory transmucosal SARS-CoV-2 invasion as a port of central nervous system entry in individuals with COVID-19. *Nat. Neurosci.* 24, 168-175 (2021).
Ochsner, S. P. et al. FcRn-Targeted Mucosal Vaccination against Influenza Virus Infection. *J Immunol.* 207(5), 1310-1321 (2021).
Oh, J. E. et al. Intranasal priming induces local lung-resident B cell populations that secrete protective mucosal antiviral IgA. *Sci. Immunol.* 6, pp. 1-11, eabj5129 (2021).
Oladunni, F. S. et al. Lethality of SARS-CoV-2 infection in K18 human angiotensin-converting enzyme 2 transgenic mice. *Nat. Commun.* 11, 6122 (2020).
Pallesen, J. et al. Immunogenicity and structures of a rationally designed prefusion MERS-CoV spike antigen. *Proc. Natl. Acad. Sci. U S A.* 114, E7348-E7357 (2017).
Planas, D. et al. Considerable escape of SARS-CoV-2 Omicron to antibody neutralization. *Nature* 602, 671-675 (2022).
Roopenian, D. C. & Akilesh, S. FcRn: the neonatal Fc receptor comes of age. *Nat. Rev. Immunol.* 9, 715-725 (2007).
Roukens, A. H. E. et al. Prolonged activation of nasal immune cell populations and development of tissue-resident SARS-CoV-2-specific $CD8^+$ T cell responses following COVID-19. *Nat. Immunol.* 23, 23-32 (2022).
Russell, M. W. & Mestecky, J. Mucosal immunity: The missing link in comprehending SARS-CoV-2 infection and transmission. *Front Immunol.* 13: 957107 (2022).
Sakurai, A. et al. Natural History of Asymptomatic SARS-CoV-2 Infection. *N. Engl. J. Med.* 383, 885-886 (2020).
Sia, S. F. et al. Pathogenesis and transmission of SARS-CoV-2 in golden hamsters. *Nature* 583, 834-838 (2020).
Spiekermann, G. M. et al. Receptor-mediated immunoglobulin G transport across mucosal barriers in adult life: functional expression of FcRn in the mammalian lung. *J. Exp. Med.* 196, 303-310 (2002). Erratum in: *J. Exp. Med.* 197, 1601 (2003).
Sterlin, D. et al. IgA dominates the early neutralizing antibody response to SARS-CoV-2. *Sci. Transl. Med.* 13, pp. 1-10, eabd2223 (2021).
Sui, Y. et al. Protection against SARS-CoV-2 infection by a mucosal vaccine in rhesus macaques. JCI Insight. Apr. 28, 2021;6(10): e148494.
Szabo, P. A., Miron, M., & Farber, D. L. Location, location, location: Tissue resident memory T cells in mice and humans. Sci. Immunol. 4(34), eaas9673 (2019).
Tang, J. et al. Respiratory mucosal immunity against SARS-CoV-2 after mRNA vaccination. *Sci. Immunol.* 7(76), eadd4853 (2022).
Van Doremalen, N. et al. ChAdOx1 nCOV-19 vaccine prevents SARS-CoV-2 pneumonia in rhesus macaques. *Nature* 586, 578-592 (2020). Erratum in: *Nature* 590, E24 (2021).
V'kovski, P., Kratzel, A., Steiner, S., Stalder, H., & Thiel, V. Coronavirus biology and replication: implications for SARS-CoV-2. *Nat. Rev. Microbiol.* 19, 155-170 (2021).
Walls A. C. et al. Structure, Function, and Antigenicity of the SARS-CoV-2 Spike Glycoprotein. *Cell* 180, 281-292 (2020). Erratum in: Cell 183, 1735 (2020).
Ward, E.S., Zhou, J., Ghetie, V., & Ober, R. J. Evidence to support the cellular mechanism involved in serum IgG homeostasis in humans. *Int. Immunol6.* 15, 187-195 (2003).
Ye, L., Zeng, R., Bai, Y., Roopenian, D. C., & Zhu, X. Efficient mucosal vaccination mediated by the neonatal Fc receptor. *Nat. Biotechnol.* 29, 158-163 (2011).
Yen, H. L. et al. Transmission of SARS-CoV-2 delta variant (AY.127) from pet hamsters to humans, leading to onward human-to-human transmission: a case study. *Lancet* 399, 1070-1078 (2022).
Yoshida, M. et al. Human neonatal Fc receptor mediates transport of IG into luminal secretions for delivery of antigens to mucosal dendritic cells. *Immunity* 20, 769-783 (2004).
Zeng, et al. SARS-CoV-2 spreads through cell-to-cell transmission. *Proc. Natl. Acad. Sci. U S A.* 119(1), e2111400119 (2022).
Zhou, D. et al. Robust SARS-CoV-2 infection in nasal turbinates after treatment with systemic neutralizing antibodies. *Cell Host Microbe.* 29(4), 551-563.e5 (2021).
An, Xingyue et al., "Single-does intranasal vaccination elicits systemic and mucosal immunity against SARS-CoV-2," BioRxiv, XP093120206, DOI: 10.1101/2020.07.23.212357 (2020).
Li, Jie et al., "Immunogenicity and Protection Efficacy of Monomeric and Trimeric Recombinant SARS Coronavirus Spike Protein Subunit Vaccine Candidates," Viral Immunology, 26(2): 126-132 (2013).
Li, Weizhong et al., An FcRn-targeted mucosal vaccine against SARS-CoV-2 infection and transmission, bioRxiv, XP093119729, DOI: 10.1101/2022.11.23.517678 (2022).
Shan et al., Communications Biology (2021) 4:1048; and https://doi.org/10.1038/s42003-021-02566-5, Nature.com/commsbio (Year: 2021).
Supplementary European Search Report mailed Jan. 29, 2024 for EP 21760268.9, filed Sep. 23, 2022.

* cited by examiner

SEQUENCE LISTING

```
<160> NUMBER OF SEQ ID NOS: 25

<210> SEQ ID NO 1
<211> LENGTH: 1504
<212> TYPE: PRT
<213> ORGANISM: Artificial Sequence
<220> FEATURE:
<223> OTHER INFORMATION: synthetic construct; SARS peptide

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240
```

-continued

```
Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655
```

-continued

```
Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Ala Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Ala Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
```

-continued

```
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Gly Ser  Gly Ser Gly
    1205                1210                1215

Ser Arg  Ser Leu Val Pro Arg  Gly Ser Pro Gly Ser  Gly Tyr Ile
    1220                1225                1230

Pro Glu  Ala Pro Arg Asp Gly  Gln Ala Tyr Val Arg  Lys Asp Gly
    1235                1240                1245

Glu Trp  Val Leu Leu Ser Thr  Phe Leu Gly Gly Ser  Gly Gly Gly
    1250                1255                1260

Gly Ser  Gly Gly Gly Gly Ser  Gly Ser Glu Pro Lys  Ser Cys Asp
    1265                1270                1275

Lys Thr  His Thr Ser Pro Pro  Ser Pro Ala Pro Glu  Leu Leu Gly
    1280                1285                1290

Gly Pro  Ser Val Phe Leu Phe  Pro Pro Lys Pro Lys  Asp Thr Leu
    1295                1300                1305

Met Ile  Ser Arg Thr Pro Glu  Val Thr Cys Val Val  Val Asp Val
    1310                1315                1320

Ser His  Glu Asp Pro Glu Val  Lys Phe Asn Trp Tyr  Val Asp Gly
    1325                1330                1335

Val Glu  Val His Asn Ala Lys  Thr Lys Pro Arg Glu  Glu Gln Tyr
    1340                1345                1350

Asn Ser  Thr Tyr Arg Val Val  Ser Val Leu Thr Val  Leu His Gln
    1355                1360                1365

Asp Trp  Leu Asn Gly Lys Glu  Tyr Lys Cys Ala Val  Ser Asn Lys
    1370                1375                1380

Ala Leu  Pro Ala Pro Ile Glu  Lys Thr Ile Ser Lys  Ala Lys Gly
    1385                1390                1395

Gln Pro  Arg Glu Pro Gln Val  Tyr Thr Leu Pro Pro  Ser Arg Asp
    1400                1405                1410

Glu Leu  Thr Lys Asn Gln Val  Ser Leu Thr Cys Leu  Val Lys Gly
    1415                1420                1425

Phe Tyr  Pro Ser Asp Ile Ala  Val Glu Trp Glu Ser  Asn Gly Gln
    1430                1435                1440

Pro Glu  Asn Asn Tyr Lys Thr  Thr Pro Pro Val Leu  Asp Ser Asp
    1445                1450                1455

Gly Ser  Phe Phe Leu Tyr Ser  Lys Leu Thr Val Asp  Lys Ser Arg
    1460                1465                1470
```

```
Trp Gln  Gln Gly Asn Val Phe  Ser Cys Ser Val Met  His Glu Ala
    1475                1480                1485

Leu His  Asn His Tyr Thr Gln  Lys Ser Leu Ser Leu  Ser Pro Gly
    1490                1495                1500

Lys


<210> SEQ ID NO 2
<211> LENGTH: 4533
<212> TYPE: DNA
<213> ORGANISM: Artificial Sequence
<220> FEATURE:
<223> OTHER INFORMATION: synthetic construct; SARs construct

<400> SEQUENCE: 2

ggtaccgcca ccatgttcgt gtttctggtg ctgctgccac tggtgtccag ccagtgcgtg     60

aacctgacca caagaaccca gctgccccct gcctatacca attctttcac aagaggcgtg    120

tactatccag acaaggtgtt tcgctcttcc gtgctgcaca gcacacagga tctgtttctg    180

cccttctttt ctaacgtgac ctggttccac gccatccacg tgtccggcac caatggcaca    240

aagaggttcg acaatcctgt gctgcccttc aacgatggcg tgtacttcgc ttctaccgag    300

aagtccaaca tcatccgggg ctggatcttt ggcaccacac tggacagcaa gacacagtct    360

ctgctgatcg tgaacaatgc caccaacgtg gtcatcaagg tgtgcgagtt ccagttttgt    420

aatgatcctt tcctgggcgt gtactatcat aagaacaata agtcctggat ggagagcgag    480

tttcgcgtgt atagctctgc taacaattgt acatttgagt acgtgagcca gccattcctg    540

atggacctgg agggcaagca gggcaatttc aagaacctga gagagttcgt gtttaagaat    600

atcgatggct acttcaagat ctacagcaag cacaccccta tcaacctggt gcgcgacctg    660

ccacagggct tctctgccct ggagcctctg gtggatctgc caatcggcat caacatcacc    720

aggtttcaga cactgctggc tctgcatcgg tcttacctga cacctggcga ctccagctct    780

ggatggaccg ctggagctgc tgcttactat gtgggctatc tgcagccaag aaccttcctg    840

ctgaagtaca acgagaatgg caccatcaca gacgccgtgg attgcgctct ggatccactg    900

tccgagacca agtgtacact gaagagcttt accgtggaga agggcatcta tcagacatcc    960

aatttcagag tgcagcccac cgagagcatc gtgcgctttc caaatatcac aaacctgtgc   1020

ccctttggcg aggtgttcaa cgccacccgc ttcgcttccg tgtacgcctg gaatagaaag   1080

cgcatctcca actgcgtggc tgactatagc gtgctgtaca actccgccag cttctctacc   1140

tttaagtgct atggcgtgtc ccccacaaag ctgaatgacc tgtgctttac caacgtgtac   1200

gccgatagct tcgtgatcag aggcgacgag gtgcgccaga tcgctccagg acagacaggc   1260

aagatcgccg actacaatta taagctgcct gacgatttca ccggctgcgt gatcgcttgg   1320

aactccaaca atctggatag caaagtgggc ggcaactaca attatctgta caggctgttt   1380

cggaagagca atctgaagcc tttcgagagg gacatctcta cagagatcta ccaggccggc   1440

tccaccccat gcaatggcgt ggagggcttt aactgttatt tccccctgca gtcttacggc   1500

ttccagccta ccaacggcgt gggctatcag ccataccggg tggtggtgct gtcttttgag   1560

ctgctgcacg ctccagctac agtgtgcgga cctaagaagt ccaccaatct ggtgaagaac   1620

aagtgcgtga acttcaactt caacggactg accggcacag gcgtgctgac cgagagcaac   1680

aagaagttcc tgccctttca gcagttcggc agggacatcg ctgataccac agacgccgtg   1740

cgggacccac agaccctgga gatcctggat atcacaccct gctctttcgg cggcgtgtcc   1800
```

-continued

```
gtgatcacac ctggcaccaa tacatctaac caggtggccg tgctgtatca ggacgtgaat   1860
tgtaccgagg tgcctgtggc catccacgct gatcagctga ccccaacatg gagggtgtac   1920
agcaccggct ctaacgtgtt tcagacacgg gctggatgtc tgatcggagc tgagcatgtg   1980
aacaattcct atgagtgcga catccccatc ggcgctggca tctgtgccag ctaccagacc   2040
cagacaaaca gccctaggag ggctgcttct gtggcttccc agagcatcat cgcctatacc   2100
atgtccctgg gcgctgagaa tagcgtggcc tactccaaca atagcatcgc tatcccaacc   2160
aacttcacaa tctccgtgac cacagagatc ctgcccgtga gcatgaccaa gacatctgtg   2220
gactgcacaa tgtatatctg tggcgattct accgagtgct ccaacctgct gctgcagtac   2280
ggcagctttt gtacccagct gaatagggct ctgacaggca tcgccgtgga gcaggataag   2340
aacacacagg aggtgttcgc ccaggtgaag cagatctaca agaccccacc catcaaggac   2400
tttggcggct tcaacttctc ccagatcctg cctgatccat ctaagccctc caaggctagc   2460
tttatcgagg acctgctgtt caacaaggtg accctggctg atgccggctt catcaagcag   2520
tatggcgatt gcctgggcga catcgctgcc agggacctga tctgtgctca gaagtttaat   2580
ggcctgaccg tgctgcctcc actgctgaca gatgagatga tcgcccagta cacatctgcc   2640
ctgctggctg gcaccatcac atccggatgg accttcggcg ctggagctgc cctgcagatc   2700
ccttttgcta tgcagatggc ctatcggttc aacggcatcg gcgtgaccca gaatgtgctg   2760
tacgagaacc agaagctgat cgctaatcag tttaactccg ccatcggcaa gatccaggac   2820
tctctgtcca gcacagcttc cgccctgggc aagctgcagg atgtggtgaa tcagaacgct   2880
caggccctga ataccctggt gaagcagctg tcttccaact tcggcgctat cagctctgtg   2940
ctgaatgata tcctgagcag actggaccca cctgaggctg aggtgcagat cgacaggctg   3000
atcacaggcc ggctgcagag cctgcagacc tacgtgacac agcagctgat cagagctgcc   3060
gagatccgcg cttctgccaa cctggctgcc accaagatgt ctgagtgcgt gctgggccag   3120
tccaagcgcg tggacttttg tggcaagggc tatcacctga tgagcttccc ccagtctgct   3180
cctcacggcg tggtgtttct gcatgtgacc tacgtgcccg cccaggagaa gaacttcacc   3240
acagctcctg ccatctgcca cgatggcaag gcccattttc ccagagaggg cgtgttcgtg   3300
tctaacggca cccattggtt tgtgacacag cgcaatttct acgagcctca gatcatcacc   3360
acagacaata ccttcgtgtc cggcaactgt gacgtggtca tcggcatcgt gaacaatacc   3420
gtgtatgatc ccctgcagcc tgagctggac tcttttaagg aggagctgga taagtacttc   3480
aagaatcaca cctccccaga cgtggatctg ggcgacatct ccggcatcaa tgctagcgtg   3540
gtgaacatcc agaaggagat cgacaggctg aacgaggtgg ccaagaatct gaacgagtct   3600
ctgatcgatc tgcaggagct gggcaagtat gagcagtaca tcaagtggcc aggatctgga   3660
tccggcagca ggtctctggt gccacggggc tctccaggat ccggatatat cccagaggct   3720
cccagagacg gacaggctta cgtgcgcaag gatggcgagt gggtgctgct gtccaccttc   3780
ctgggcggct ctggaggagg aggatccgga ggaggaggat ccggcagcga gcctaagtcc   3840
tgcgacaaga cccacacaag cccaccatct ccagctcctg agctgctggg aggaccaagc   3900
gtgttcctgt ttcctccaaa gcctaaggat acactgatga tctctcggac cccagaggtg   3960
acatgcgtgg tggtggacgt gtcccacgag gaccccgagg tgaagtttaa ctggtacgtg   4020
gacggcgtgg aggtgcataa tgctaagacc aagccaaggg aggagcagta taacagcaca   4080
taccgggtgg tgtctgtgct gaccgtgctg catcaggatt ggctgaacgg caaggaatac   4140
aagtgcgctg tgagcaataa ggccctgcca gctcccatcg agaagacaat ctctaaggcc   4200
```

-continued aagggccagc ctagagagcc acaggtgtat accctgccac cttcccgcga cgagctgacc 4260
aagaatcagg tgagcctgac atgtctggtg aagggcttct accctagcga tatcgctgtg 4320
gagtgggagt ctaacggcca gccagagaac aattataaga ccacaccacc cgtgctggac 4380
tccgatggca gcttctttct gtacagcaag ctgacagtgg acaagtctcg gtggcagcag 4440
ggcaacgtgt tctcctgctc cgtgatgcat gaggccctgc acaaccatta cacccagaag 4500
agcctgtctc tgtcccctgg caagtgactc gag 4533

<210> SEQ ID NO 3
<211> LENGTH: 976
<212> TYPE: PRT
<213> ORGANISM: Artificial Sequence
<220> FEATURE:
<223> OTHER INFORMATION: synthetic construct; SARS peptide

<400> SEQUENCE: 3

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

-continued

```
Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Ala Gly Ser Gly
        675                 680                 685

Ser Gly Ser Arg Ser Leu Val Pro Arg Gly Ser Pro Gly Ser Gly Tyr
    690                 695                 700

Ile Pro Glu Ala Pro Arg Asp Gly Gln Ala Tyr Val Arg Lys Asp Gly
705                 710                 715                 720
```

-continued

```
Glu Trp Val Leu Leu Ser Thr Phe Leu Gly Gly Ser Gly Gly Gly Gly
                725                 730                 735

Ser Gly Gly Gly Gly Ser Gly Ser Glu Pro Lys Ser Cys Asp Lys Thr
            740                 745                 750

His Thr Ser Pro Pro Ser Pro Ala Pro Glu Leu Leu Gly Gly Pro Ser
        755                 760                 765

Val Phe Leu Phe Pro Pro Lys Pro Lys Asp Thr Leu Met Ile Ser Arg
    770                 775                 780

Thr Pro Glu Val Thr Cys Val Val Val Asp Val Ser His Glu Asp Pro
785                 790                 795                 800

Glu Val Lys Phe Asn Trp Tyr Val Asp Gly Val Glu Val His Asn Ala
                805                 810                 815

Lys Thr Lys Pro Arg Glu Glu Gln Tyr Asn Ser Thr Tyr Arg Val Val
            820                 825                 830

Ser Val Leu Thr Val Leu His Gln Asp Trp Leu Asn Gly Lys Glu Tyr
        835                 840                 845

Lys Cys Ala Val Ser Asn Lys Ala Leu Pro Ala Pro Ile Glu Lys Thr
    850                 855                 860

Ile Ser Lys Ala Lys Gly Gln Pro Arg Glu Pro Gln Val Tyr Thr Leu
865                 870                 875                 880

Pro Pro Ser Arg Asp Glu Leu Thr Lys Asn Gln Val Ser Leu Thr Cys
                885                 890                 895

Leu Val Lys Gly Phe Tyr Pro Ser Asp Ile Ala Val Glu Trp Glu Ser
            900                 905                 910

Asn Gly Gln Pro Glu Asn Asn Tyr Lys Thr Thr Pro Pro Val Leu Asp
        915                 920                 925

Ser Asp Gly Ser Phe Phe Leu Tyr Ser Lys Leu Thr Val Asp Lys Ser
    930                 935                 940

Arg Trp Gln Gln Gly Asn Val Phe Ser Cys Ser Val Met His Glu Ala
945                 950                 955                 960

Leu His Asn His Tyr Thr Gln Lys Ser Leu Ser Leu Ser Pro Gly Lys
                965                 970                 975
```

```
<210> SEQ ID NO 4
<211> LENGTH: 2949
<212> TYPE: DNA
<213> ORGANISM: Artificial Sequence
<220> FEATURE:
<223> OTHER INFORMATION: synthetic construct; SARs construct

<400> SEQUENCE: 4

ggtaccgcca ccatgttcgt gtttctggtg ctgctgccac tggtgtccag ccagtgcgtg     60

aacctgacca caagaaccca gctgccccct gcctatacca attctttcac aagaggcgtg    120

tactatccag acaaggtgtt tcgctcttcc gtgctgcaca gcacacagga tctgtttctg    180

cccttctttt ctaacgtgac ctggttccac gccatccacg tgtccggcac caatggcaca    240

aagaggttcg acaatcctgt gctgcccttc aacgatggcg tgtacttcgc ttctaccgag    300

aagtccaaca tcatccgggg ctggatcttt ggcaccacac tggacagcaa gacacagtct    360

ctgctgatcg tgaacaatgc caccaacgtg gtcatcaagg tgtgcgagtt ccagttttgt    420

aatgatcctt tcctgggcgt gtactatcat aagaacaata agtcctggat ggagagcgag    480

tttcgcgtgt atagctctgc taacaattgt acatttgagt acgtgagcca gccattcctg    540

atggacctgg agggcaagca gggcaatttc aagaacctga gagagttcgt gtttaagaat    600

atcgatggct acttcaagat ctacagcaag cacaccccta tcaacctggt gcgcgacctg    660
```

-continued

```
ccacagggct tctctgccct ggagcctctg gtggatctgc caatcggcat caacatcacc    720
aggtttcaga cactgctggc tctgcatcgg tcttacctga cacctggcga ctccagctct    780
ggatggaccg ctggagctgc tgcttactat gtgggctatc tgcagccaag aaccttcctg    840
ctgaagtaca acgagaatgg caccatcaca gacgccgtgg attgcgctct ggatccactg    900
tccgagacca agtgtacact gaagagcttt accgtggaga agggcatcta tcagacatcc    960
aatttcagag tgcagcccac cgagagcatc gtgcgctttc caaatatcac aaacctgtgc   1020
ccctttggcg aggtgttcaa cgccacccgc ttcgcttccg tgtacgcctg gaatagaaag   1080
cgcatctcca actgcgtggc tgactatagc gtgctgtaca actccgccag cttctctacc   1140
tttaagtgct atggcgtgtc ccccacaaag ctgaatgacc tgtgctttac caacgtgtac   1200
gccgatagct tcgtgatcag aggcgacgag gtgcgccaga tcgctccagg acagacaggc   1260
aagatcgccg actacaatta taagctgcct gacgatttca ccggctgcgt gatcgcttgg   1320
aactccaaca atctggatag caaagtgggc ggcaactaca attatctgta caggctgttt   1380
cggaagagca atctgaagcc tttcgagagg gacatctcta cagagatcta ccaggccggc   1440
tccaccccat gcaatggcgt ggagggcttt aactgttatt tccccctgca gtcttacggc   1500
ttccagccta ccaacggcgt gggctatcag ccataccggg tggtggtgct gtcttttgag   1560
ctgctgcacg ctccagctac agtgtgcgga cctaagaagt ccaccaatct ggtgaagaac   1620
aagtgcgtga acttcaactt caacggactg accggcacag gcgtgctgac cgagagcaac   1680
aagaagttcc tgccctttca gcagttcggc agggacatcg ctgataccac agacgccgtg   1740
cgggacccac agaccctgga gatcctggat atcacaccct gctctttcgg cggcgtgtcc   1800
gtgatcacac ctggcaccaa tacatctaac caggtggccg tgctgtatca ggacgtgaat   1860
tgtaccgagg tgcctgtggc catccacgct gatcagctga ccccaacatg gagggtgtac   1920
agcaccggct ctaacgtgtt tcagacacgg gctggatgtc tgatcggagc tgagcatgtg   1980
aacaattcct atgagtgcga catccccatc ggcgctggca tctgtgccag ctaccagacc   2040
cagacaaaca gccctaggag ggctgctgga tctggatccg gcagcaggtc tctggtgcca   2100
cggggctctc caggatccgg atatatccca gaggctccca gagacggaca ggcttacgtg   2160
cgcaaggatg gcgagtgggt gctgctgtcc accttcctgg gcggctctgg aggaggagga   2220
tccggaggag gaggatccgg cagcgagcct aagtcctgcg acaagaccca cacaagccca   2280
ccatctccag ctcctgagct gctgggagga ccaagcgtgt tcctgtttcc tccaaagcct   2340
aaggatacac tgatgatctc tcggacccca gaggtgacat gcgtggtggt ggacgtgtcc   2400
cacgaggacc ccgaggtgaa gtttaactgg tacgtggacg gcgtggaggt gcataatgct   2460
aagaccaagc caagggagga gcagtataac agcacatacc gggtggtgtc tgtgctgacc   2520
gtgctgcatc aggattggct gaacggcaag gaatacaagt gcgctgtgag caataaggcc   2580
ctgccagctc ccatcgagaa gacaatctct aaggccaagg gccagcctag agagccacag   2640
gtgtataccc tgccaccttc ccgcgacgag ctgaccaaga atcaggtgag cctgacatgt   2700
ctggtgaagg gcttctaccc tagcgatatc gctgtggagt gggagtctaa cggccagcca   2760
gagaacaatt ataagaccac accacccgtg ctggactccg atggcagctt ctttctgtac   2820
agcaagctga cagtggacaa gtctcggtgg cagcagggca acgtgttctc ctgctccgtg   2880
atgcatgagg ccctgcacaa ccattacacc cagaagagcc tgtctctgtc ccctggcaag   2940
tgactcgag                                                           2949
```

-continued

<210> SEQ ID NO 5
<211> LENGTH: 530
<212> TYPE: PRT
<213> ORGANISM: Artificial Sequence
<220> FEATURE:
<223> OTHER INFORMATION: synthetic construct; SARS peptide

<400> SEQUENCE: 5

```
Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Gly
225                 230                 235                 240

Ser Gly Ser Gly Ser Arg Ser Leu Val Pro Arg Gly Ser Pro Gly Ser
                245                 250                 255

Gly Tyr Ile Pro Glu Ala Pro Arg Asp Gly Gln Ala Tyr Val Arg Lys
            260                 265                 270

Asp Gly Glu Trp Val Leu Leu Ser Thr Phe Leu Gly Gly Ser Gly Gly
        275                 280                 285

Gly Gly Ser Gly Gly Gly Gly Ser Gly Ser Glu Pro Lys Ser Cys Asp
    290                 295                 300

Lys Thr His Thr Ser Pro Pro Ser Pro Ala Pro Glu Leu Leu Gly Gly
305                 310                 315                 320

Pro Ser Val Phe Leu Phe Pro Pro Lys Pro Lys Asp Thr Leu Met Ile
                325                 330                 335

Ser Arg Thr Pro Glu Val Thr Cys Val Val Val Asp Val Ser His Glu
            340                 345                 350

Asp Pro Glu Val Lys Phe Asn Trp Tyr Val Asp Gly Val Glu Val His
        355                 360                 365
```

-continued

```
Asn Ala Lys Thr Lys Pro Arg Glu Glu Gln Tyr Asn Ser Thr Tyr Arg
    370                 375                 380

Val Val Ser Val Leu Thr Val Leu His Gln Asp Trp Leu Asn Gly Lys
385                 390                 395                 400

Glu Tyr Lys Cys Ala Val Ser Asn Lys Ala Leu Pro Ala Pro Ile Glu
                405                 410                 415

Lys Thr Ile Ser Lys Ala Lys Gly Gln Pro Arg Glu Pro Gln Val Tyr
            420                 425                 430

Thr Leu Pro Pro Ser Arg Asp Glu Leu Thr Lys Asn Gln Val Ser Leu
        435                 440                 445

Thr Cys Leu Val Lys Gly Phe Tyr Pro Ser Asp Ile Ala Val Glu Trp
    450                 455                 460

Glu Ser Asn Gly Gln Pro Glu Asn Asn Tyr Lys Thr Thr Pro Pro Val
465                 470                 475                 480

Leu Asp Ser Asp Gly Ser Phe Phe Leu Tyr Ser Lys Leu Thr Val Asp
                485                 490                 495

Lys Ser Arg Trp Gln Gln Gly Asn Val Phe Ser Cys Ser Val Met His
            500                 505                 510

Glu Ala Leu His Asn His Tyr Thr Gln Lys Ser Leu Ser Leu Ser Pro
        515                 520                 525

Gly Lys
    530


<210> SEQ ID NO 6
<211> LENGTH: 1611
<212> TYPE: DNA
<213> ORGANISM: Artificial Sequence
<220> FEATURE:
<223> OTHER INFORMATION: synthetic construct; SARS construct

<400> SEQUENCE: 6

ggtaccgcca ccatgttcgt gtttctggtg ctgctgccac tggtgtccag ccagtgcgtg      60

agagtgcagc ccaccgagag catcgtgcgc tttccaaata tcacaaacct gtgccccttt     120

ggcgaggtgt tcaacgccac ccgcttcgct tccgtgtacg cctggaatag aaagcgcatc     180

tccaactgcg tggctgacta tagcgtgctg tacaactccg ccagcttctc tacctttaag     240

tgctatggcg tgtcccccac aaagctgaat gacctgtgct ttaccaacgt gtacgccgat     300

agcttcgtga tcagaggcga cgaggtgcgc cagatcgctc caggacagac aggcaagatc     360

gccgactaca attataagct gcctgacgat ttcaccggct gcgtgatcgc ttggaactcc     420

aacaatctgg atagcaaagt gggcggcaac tacaattatc tgtacaggct gtttcggaag     480

agcaatctga agcctttcga gagggacatc tctacagaga tctaccaggc cggctccacc     540

ccatgcaatg gcgtggaggg ctttaactgt tatttccccc tgcagtctta cggcttccag     600

cctaccaacg gcgtgggcta tcagccatac cgggtggtgg tgctgtcttt tgagctgctg     660

cacgctccag ctacagtgtg cggacctaag aagtccacca atctggtgaa gaacaagtgc     720

gtgaacttcg gatctggatc cggcagcagg tctctggtgc cacggggctc tccaggatcc     780

ggatatatcc cagaggctcc cagagacgga caggcttacg tgcgcaagga tggcgagtgg     840

gtgctgctgt ccaccttcct gggcggctct ggaggaggag gatccggagg aggaggatcc     900

ggcagcgagc ctaagtcctg cgacaagacc cacacaagcc caccatctcc agctcctgag     960

ctgctgggag gaccaagcgt gttcctgttt cctccaaagc ctaaggatac actgatgatc    1020

tctcggaccc cagaggtgac atgcgtggtg gtggacgtgt cccacgagga ccccgaggtg    1080
```

-continued

```
aagtttaact ggtacgtgga cggcgtggag gtgcataatg ctaagaccaa gccaagggag   1140

gagcagtata acagcacata ccgggtggtg tctgtgctga ccgtgctgca tcaggattgg   1200

ctgaacggca aggaatacaa gtgcgctgtg agcaataagg ccctgccagc tcccatcgag   1260

aagacaatct ctaaggccaa gggccagcct agagagccac aggtgtatac cctgccacct   1320

tcccgcgacg agctgaccaa gaatcaggtg agcctgacat gtctggtgaa gggcttctac   1380

cctagcgata tcgctgtgga gtgggagtct aacggccagc cagagaacaa ttataagacc   1440

acaccacccg tgctggactc cgatggcagc ttctttctgt acagcaagct gacagtggac   1500

aagtctcggt ggcagcaggg caacgtgttc tcctgctccg tgatgcatga ggccctgcac   1560

aaccattaca cccagaagag cctgtctctg tcccctggca agtgactcga g            1611
```

```
<210> SEQ ID NO 7
<211> LENGTH: 232
<212> TYPE: PRT
<213> ORGANISM: Artificial Sequence
<220> FEATURE:
<223> OTHER INFORMATION: synthetic construct; IgG1 fragment

<400> SEQUENCE: 7

Glu Pro Lys Ser Cys Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 8
<211> LENGTH: 1213
<212> TYPE: PRT
<213> ORGANISM: Artificial Sequence
<220> FEATURE:
```

-continued

<223> OTHER INFORMATION: synthetic construct; fragment of SARS Cov-2 S protein

<400> SEQUENCE: 8

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400
```

```
Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Ala Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Ala Ser
                805                 810                 815
```

-continued

```
Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro
    1205                1210
```

<210> SEQ ID NO 9
<211> LENGTH: 699
<212> TYPE: DNA
<213> ORGANISM: Artificial Sequence
<220> FEATURE:
<223> OTHER INFORMATION: synthetic construct; fragment of IgG1

<400> SEQUENCE: 9
gagcctaagt cctgcgacaa gacccacaca agcccaccat ctccagctcc tgagctgctg 60
ggaggaccaa gcgtgttcct gtttcctcca aagcctaagg atacactgat gatctctcgg 120
accccagagg tgacatgcgt ggtggtggac gtgtcccacg aggaccccga ggtgaagttt 180
aactggtacg tggacggcgt ggaggtgcat aatgctaaga ccaagccaag ggaggagcag 240
tataacagca cataccgggt ggtgtctgtg ctgaccgtgc tgcatcagga ttggctgaac 300
ggcaaggaat acaagtgcgc tgtgagcaat aaggccctgc cagctcccat cgagaagaca 360
atctctaagg ccaagggcca gcctagagag ccacaggtgt ataccctgcc accttcccgc 420
gacgagctga ccaagaatca ggtgagcctg acatgtctgg tgaagggctt ctaccctagc 480
gatatcgctg tggagtggga gtctaacggc cagccagaga acaattataa gaccacacca 540
cccgtgctgg actccgatgg cagcttcttt ctgtacagca agctgacagt ggacaagtct 600
cggtggcagc agggcaacgt gttctcctgc tccgtgatgc atgaggccct gcacaaccat 660
tacacccaga agagcctgtc tctgtcccct ggcaagtga 699

<210> SEQ ID NO 10
<211> LENGTH: 699
<212> TYPE: DNA
<213> ORGANISM: Artificial Sequence
<220> FEATURE:
<223> OTHER INFORMATION: synthetic construct; IgG2a

<400> SEQUENCE: 10
gagcccagag ggcccacaat caagccctct cctccatcca aatccccagc acctaacctc 60
ttgggtggac catccgtctt catcttccct ccaaagatca aggatgtact catgatctcc 120
ctgagcccca tagtcacatg tgtggtggtg gatgtgagcg aggatgaccc agatgtccag 180
atcagctggt ttgtgaacaa cgtggaagta cacacagctc agacacaaac ccatagagag 240
gattacaaca gtactctccg ggtggtcagt gccctcccca tccagcacca ggactggatg 300
agtggcaagg cgttcgcatg cgcggtcaac aacaaagacc tcccagcgcc catcgagaga 360
accatctcaa aacccaaagg gtcagtaaga gctccacagg tatatgtctt gcctccacca 420
gaagaagaga tgactaagaa acaggtcact ctgacctgca tggtcacaga cttcatgcct 480
gaagacattt acgtggagtg gaccaacaac gggaaaacag agctaaacta caagaacact 540
gaaccagtcc tggactctga tggttcttac ttcatgtaca gcaagctgag agtggaaaag 600
aagaactggg tggaaagaaa tagctactcc tgttcagtgg tccacgaggg tctgcacaat 660
caccacacga ctaagagctt ctcccggact ccgggtaaa 699

<210> SEQ ID NO 11
<211> LENGTH: 1273
<212> TYPE: PRT
<213> ORGANISM: Artificial Sequence
<220> FEATURE:
<223> OTHER INFORMATION: synthetic construct; SARS-COV-2 S protein
variant

<400> SEQUENCE: 11

Met Phe Val Phe Leu Val Leu Leu Pro Leu Val Ser Ser Gln Cys Val

-continued

```
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430
```

-continued

```
Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Gly Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845
```

-continued

```
Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
```

```
    1250                1255                1260

Val Leu  Lys Gly Val Lys Leu  His Tyr Thr
    1265                1270


<210> SEQ ID NO 12
<211> LENGTH: 1270
<212> TYPE: PRT
<213> ORGANISM: Artificial Sequence
<220> FEATURE:
<223> OTHER INFORMATION: synthetic construct; SARS COV-2 S protein
      variant

<400> SEQUENCE: 12

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile Ser Gly Thr Asn Gly Thr Lys Arg Phe Asp Asn Pro
65                  70                  75                  80

Val Leu Pro Phe Asn Asp Gly Val Tyr Phe Ala Ser Thr Glu Lys Ser
                85                  90                  95

Asn Ile Ile Arg Gly Trp Ile Phe Gly Thr Thr Leu Asp Ser Lys Thr
            100                 105                 110

Gln Ser Leu Leu Ile Val Asn Asn Ala Thr Asn Val Val Ile Lys Val
        115                 120                 125

Cys Glu Phe Gln Phe Cys Asn Asp Pro Phe Leu Gly Val Tyr His Lys
    130                 135                 140

Asn Asn Lys Ser Trp Met Glu Ser Glu Phe Arg Val Tyr Ser Ser Ala
145                 150                 155                 160

Asn Asn Cys Thr Phe Glu Tyr Val Ser Gln Pro Phe Leu Met Asp Leu
                165                 170                 175

Glu Gly Lys Gln Gly Asn Phe Lys Asn Leu Arg Glu Phe Val Phe Lys
            180                 185                 190

Asn Ile Asp Gly Tyr Phe Lys Ile Tyr Ser Lys His Thr Pro Ile Asn
        195                 200                 205

Leu Val Arg Asp Leu Pro Gln Gly Phe Ser Ala Leu Glu Pro Leu Val
    210                 215                 220

Asp Leu Pro Ile Gly Ile Asn Ile Thr Arg Phe Gln Thr Leu Leu Ala
225                 230                 235                 240

Leu His Arg Ser Tyr Leu Thr Pro Gly Asp Ser Ser Ser Gly Trp Thr
                245                 250                 255

Ala Gly Ala Ala Ala Tyr Tyr Val Gly Tyr Leu Gln Pro Arg Thr Phe
            260                 265                 270

Leu Leu Lys Tyr Asn Glu Asn Gly Thr Ile Thr Asp Ala Val Asp Cys
        275                 280                 285

Ala Leu Asp Pro Leu Ser Glu Thr Lys Cys Thr Leu Lys Ser Phe Thr
    290                 295                 300

Val Glu Lys Gly Ile Tyr Gln Thr Ser Asn Phe Arg Val Gln Pro Thr
305                 310                 315                 320

Glu Ser Ile Val Arg Phe Pro Asn Ile Thr Asn Leu Cys Pro Phe Gly
                325                 330                 335
```

-continued

Glu Val Phe Asn Ala Thr Arg Phe Ala Ser Val Tyr Ala Trp Asn Arg
340 345 350

Lys Arg Ile Ser Asn Cys Val Ala Asp Tyr Ser Val Leu Tyr Asn Ser
355 360 365

Ala Ser Phe Ser Thr Phe Lys Cys Tyr Gly Val Ser Pro Thr Lys Leu
370 375 380

Asn Asp Leu Cys Phe Thr Asn Val Tyr Ala Asp Ser Phe Val Ile Arg
385 390 395 400

Gly Asp Glu Val Arg Gln Ile Ala Pro Gly Gln Thr Gly Lys Ile Ala
405 410 415

Asp Tyr Asn Tyr Lys Leu Pro Asp Asp Phe Thr Gly Cys Val Ile Ala
420 425 430

Trp Asn Ser Asn Asn Leu Asp Ser Lys Val Gly Gly Asn Tyr Asn Tyr
435 440 445

Leu Tyr Arg Leu Phe Arg Lys Ser Asn Leu Lys Pro Phe Glu Arg Asp
450 455 460

Ile Ser Thr Glu Ile Tyr Gln Ala Gly Ser Thr Pro Cys Asn Gly Val
465 470 475 480

Glu Gly Phe Asn Cys Tyr Phe Pro Leu Gln Ser Tyr Gly Phe Gln Pro
485 490 495

Thr Tyr Gly Val Gly Tyr Gln Pro Tyr Arg Val Val Val Leu Ser Phe
500 505 510

Glu Leu Leu His Ala Pro Ala Thr Val Cys Gly Pro Lys Lys Ser Thr
515 520 525

Asn Leu Val Lys Asn Lys Cys Val Asn Phe Asn Phe Asn Gly Leu Thr
530 535 540

Gly Thr Gly Val Leu Thr Glu Ser Asn Lys Lys Phe Leu Pro Phe Gln
545 550 555 560

Gln Phe Gly Arg Asp Ile Asp Asp Thr Thr Asp Ala Val Arg Asp Pro
565 570 575

Gln Thr Leu Glu Ile Leu Asp Ile Thr Pro Cys Ser Phe Gly Gly Val
580 585 590

Ser Val Ile Thr Pro Gly Thr Asn Thr Ser Asn Gln Val Ala Val Leu
595 600 605

Tyr Gln Gly Val Asn Cys Thr Glu Val Pro Val Ala Ile His Ala Asp
610 615 620

Gln Leu Thr Pro Thr Trp Arg Val Tyr Ser Thr Gly Ser Asn Val Phe
625 630 635 640

Gln Thr Arg Ala Gly Cys Leu Ile Gly Ala Glu His Val Asn Asn Ser
645 650 655

Tyr Glu Cys Asp Ile Pro Ile Gly Ala Gly Ile Cys Ala Ser Tyr Gln
660 665 670

Thr Gln Thr Asn Ser His Arg Arg Ala Arg Ser Val Ala Ser Gln Ser
675 680 685

Ile Ile Ala Tyr Thr Met Ser Leu Gly Ala Glu Asn Ser Val Ala Tyr
690 695 700

Ser Asn Asn Ser Ile Ala Ile Pro Ile Asn Phe Thr Ile Ser Val Thr
705 710 715 720

Thr Glu Ile Leu Pro Val Ser Met Thr Lys Thr Ser Val Asp Cys Thr
725 730 735

Met Tyr Ile Cys Gly Asp Ser Thr Glu Cys Ser Asn Leu Leu Leu Gln
740 745 750

Tyr Gly Ser Phe Cys Thr Gln Leu Asn Arg Ala Leu Thr Gly Ile Ala

```
        755                 760                 765

Val Glu Gln Asp Lys Asn Thr Gln Glu Val Phe Ala Gln Val Lys Gln
    770                 775                 780

Ile Tyr Lys Thr Pro Pro Ile Lys Asp Phe Gly Gly Phe Asn Phe Ser
785                 790                 795                 800

Gln Ile Leu Pro Asp Pro Ser Lys Pro Ser Lys Arg Ser Phe Ile Glu
                805                 810                 815

Asp Leu Leu Phe Asn Lys Val Thr Leu Ala Asp Ala Gly Phe Ile Lys
            820                 825                 830

Gln Tyr Gly Asp Cys Leu Gly Asp Ile Ala Ala Arg Asp Leu Ile Cys
        835                 840                 845

Ala Gln Lys Phe Asn Gly Leu Thr Val Leu Pro Pro Leu Leu Thr Asp
    850                 855                 860

Glu Met Ile Ala Gln Tyr Thr Ser Ala Leu Leu Ala Gly Thr Ile Thr
865                 870                 875                 880

Ser Gly Trp Thr Phe Gly Ala Gly Ala Ala Leu Gln Ile Pro Phe Ala
                885                 890                 895

Met Gln Met Ala Tyr Arg Phe Asn Gly Ile Gly Val Thr Gln Asn Val
            900                 905                 910

Leu Tyr Glu Asn Gln Lys Leu Ile Ala Asn Gln Phe Asn Ser Ala Ile
        915                 920                 925

Gly Lys Ile Gln Asp Ser Leu Ser Ser Thr Ala Ser Ala Leu Gly Lys
    930                 935                 940

Leu Gln Asp Val Val Asn Gln Asn Ala Gln Ala Leu Asn Thr Leu Val
945                 950                 955                 960

Lys Gln Leu Ser Ser Asn Phe Gly Ala Ile Ser Ser Val Leu Asn Asp
                965                 970                 975

Ile Leu Ala Arg Leu Asp Lys Val Glu Ala Glu Val Gln Ile Asp Arg
            980                 985                 990

Leu Ile Thr Gly Arg Leu Gln Ser  Leu Gln Thr Tyr Val  Thr Gln Gln
        995                 1000                1005

Leu Ile  Arg Ala Ala Glu Ile  Arg Ala Ser Ala Asn  Leu Ala Ala
    1010                1015                1020

Thr Lys  Met Ser Glu Cys Val  Leu Gly Gln Ser Lys  Arg Val Asp
    1025                1030                1035

Phe Cys  Gly Lys Gly Tyr His  Leu Met Ser Phe Pro  Gln Ser Ala
    1040                1045                1050

Pro His  Gly Val Val Phe Leu  His Val Thr Tyr Val  Pro Ala Gln
    1055                1060                1065

Glu Lys  Asn Phe Thr Thr Ala  Pro Ala Ile Cys His  Asp Gly Lys
    1070                1075                1080

Ala His  Phe Pro Arg Glu Gly  Val Phe Val Ser Asn  Gly Thr His
    1085                1090                1095

Trp Phe  Val Thr Gln Arg Asn  Phe Tyr Glu Pro Gln  Ile Ile Thr
    1100                1105                1110

Thr His  Asn Thr Phe Val Ser  Gly Asn Cys Asp Val  Val Ile Gly
    1115                1120                1125

Ile Val  Asn Asn Thr Val Tyr  Asp Pro Leu Gln Pro  Glu Leu Asp
    1130                1135                1140

Ser Phe  Lys Glu Glu Leu Asp  Lys Tyr Phe Lys Asn  His Thr Ser
    1145                1150                1155

Pro Asp  Val Asp Leu Gly Asp  Ile Ser Gly Ile Asn  Ala Ser Val
    1160                1165                1170
```

```
Val Asn  Ile Gln Lys Glu Ile  Asp Arg Leu Asn Glu  Val Ala Lys
    1175                 1180                 1185

Asn Leu  Asn Glu Ser Leu Ile  Asp Leu Gln Glu Leu  Gly Lys Tyr
    1190                 1195                 1200

Glu Gln  Tyr Ile Lys Trp Pro  Trp Tyr Ile Trp Leu  Gly Phe Ile
    1205                 1210                 1215

Ala Gly  Leu Ile Ala Ile Val  Met Val Thr Ile Met  Leu Cys Cys
    1220                 1225                 1230

Met Thr  Ser Cys Cys Ser Cys  Leu Lys Gly Cys Cys  Ser Cys Gly
    1235                 1240                 1245

Ser Cys  Cys Lys Phe Asp Glu  Asp Asp Ser Glu Pro  Val Leu Lys
    1250                 1255                 1260

Gly Val  Lys Leu His Tyr Thr
    1265                 1270


<210> SEQ ID NO 13
<211> LENGTH: 1273
<212> TYPE: PRT
<213> ORGANISM: Artificial Sequence
<220> FEATURE:
<223> OTHER INFORMATION: synthetic construct; SARS Cov-2 variant

<400> SEQUENCE: 13

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Ala
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Gly Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255
```

-continued

```
Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Asn Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Lys Gly Phe Asn Cys Tyr Phe Pro Leu Gln Ser Tyr Gly
                485                 490                 495

Phe Gln Pro Thr Tyr Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670
```

-continued

```
Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Val Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
```

```
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270


<210> SEQ ID NO 14
<211> LENGTH: 1273
<212> TYPE: PRT
<213> ORGANISM: Artificial Sequence
<220> FEATURE:
<223> OTHER INFORMATION: synthetic construct; SARS Cov-2 S protein
      variant

<400> SEQUENCE: 14

Met Phe Val Phe Leu Val Leu Leu Pro Leu Val Ser Ser Gln Cys Val
1               5                   10                  15

Asn Phe Thr Asn Arg Thr Gln Leu Pro Ser Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Tyr Pro Phe Leu Gly Val Tyr
    130                 135                 140

Tyr His Lys Asn Asn Lys Ser Trp Met Glu Ser Glu Phe Arg Val Tyr
145                 150                 155                 160
```

-continued

```
Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Ser Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Thr Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Lys Gly Phe Asn Cys Tyr Phe Pro Leu Gln Ser Tyr Gly
                485                 490                 495

Phe Gln Pro Thr Tyr Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
```

-continued

```
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu Tyr Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005
```

Thr Gln Gln Leu Ile Arg Ala Ala Glu Ile Arg Ala Ser Ala Asn
1010 1015 1020

Leu Ala Ala Ile Lys Met Ser Glu Cys Val Leu Gly Gln Ser Lys
1025 1030 1035

Arg Val Asp Phe Cys Gly Lys Gly Tyr His Leu Met Ser Phe Pro
1040 1045 1050

Gln Ser Ala Pro His Gly Val Val Phe Leu His Val Thr Tyr Val
1055 1060 1065

Pro Ala Gln Glu Lys Asn Phe Thr Thr Ala Pro Ala Ile Cys His
1070 1075 1080

Asp Gly Lys Ala His Phe Pro Arg Glu Gly Val Phe Val Ser Asn
1085 1090 1095

Gly Thr His Trp Phe Val Thr Gln Arg Asn Phe Tyr Glu Pro Gln
1100 1105 1110

Ile Ile Thr Thr Asp Asn Thr Phe Val Ser Gly Asn Cys Asp Val
1115 1120 1125

Val Ile Gly Ile Val Asn Asn Thr Val Tyr Asp Pro Leu Gln Pro
1130 1135 1140

Glu Leu Asp Ser Phe Lys Glu Glu Leu Asp Lys Tyr Phe Lys Asn
1145 1150 1155

His Thr Ser Pro Asp Val Asp Leu Gly Asp Ile Ser Gly Ile Asn
1160 1165 1170

Ala Ser Val Val Asn Ile Gln Lys Glu Ile Asp Arg Leu Asn Glu
1175 1180 1185

Val Ala Lys Asn Leu Asn Glu Ser Leu Ile Asp Leu Gln Glu Leu
1190 1195 1200

Gly Lys Tyr Glu Gln Tyr Ile Lys Trp Pro Trp Tyr Ile Trp Leu
1205 1210 1215

Gly Phe Ile Ala Gly Leu Ile Ala Ile Val Met Val Thr Ile Met
1220 1225 1230

Leu Cys Cys Met Thr Ser Cys Cys Ser Cys Leu Lys Gly Cys Cys
1235 1240 1245

Ser Cys Gly Ser Cys Cys Lys Phe Asp Glu Asp Asp Ser Glu Pro
1250 1255 1260

Val Leu Lys Gly Val Lys Leu His Tyr Thr
1265 1270

<210> SEQ ID NO 15
<211> LENGTH: 1273
<212> TYPE: PRT
<213> ORGANISM: Artificial Sequence
<220> FEATURE:
<223> OTHER INFORMATION: synthetic construct; SARS Cov-2 S protein variant

<400> SEQUENCE: 15

Met Phe Val Phe Leu Val Leu Leu Pro Leu Val Ser Ile Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp

-continued

```
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Cys Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Arg Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495
```

-continued

```
Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910
```

```
Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 16
<211> LENGTH: 1271
<212> TYPE: PRT
<213> ORGANISM: Artificial Sequence
<220> FEATURE:
<223> OTHER INFORMATION: synthetic construct; SARS Cov-2 S protein variant

<400> SEQUENCE: 16

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile Ser Gly Thr Asn Gly Thr Lys Arg Phe Asp Asn Pro
65                  70                  75                  80

Val Leu Pro Phe Asn Asp Gly Val Tyr Phe Ala Ser Thr Glu Lys Ser
                85                  90                  95

Asn Ile Ile Arg Gly Trp Ile Phe Gly Thr Thr Leu Asp Ser Lys Thr
            100                 105                 110

Gln Ser Leu Leu Ile Val Asn Asn Ala Thr Asn Val Val Ile Lys Val
        115                 120                 125

Cys Glu Phe Gln Phe Cys Asn Asp Pro Phe Leu Gly Val Tyr Tyr His
    130                 135                 140

Lys Asn Asn Lys Ser Trp Met Glu Ser Glu Phe Arg Val Tyr Ser Ser
145                 150                 155                 160

Ala Asn Asn Cys Thr Phe Glu Tyr Val Ser Gln Pro Phe Leu Met Asp
                165                 170                 175

Leu Glu Gly Lys Gln Gly Asn Phe Lys Asn Leu Arg Glu Phe Val Phe
            180                 185                 190

Lys Asn Ile Asp Gly Tyr Phe Lys Ile Tyr Ser Lys His Thr Pro Ile
        195                 200                 205

Asn Leu Val Arg Asp Leu Pro Gln Gly Phe Ser Ala Leu Glu Pro Leu
    210                 215                 220

Val Asp Leu Pro Ile Gly Ile Asn Ile Thr Arg Phe Gln Thr Leu Leu
225                 230                 235                 240

Ala Leu His Arg Ser Tyr Leu Thr Pro Gly Asp Ser Ser Ser Gly Trp
                245                 250                 255

Thr Ala Gly Ala Ala Ala Tyr Tyr Val Gly Tyr Leu Gln Pro Arg Thr
            260                 265                 270

Phe Leu Leu Lys Tyr Asn Glu Asn Gly Thr Ile Thr Asp Ala Val Asp
        275                 280                 285

Cys Ala Leu Asp Pro Leu Ser Glu Thr Lys Cys Thr Leu Lys Ser Phe
    290                 295                 300

Thr Val Glu Lys Gly Ile Tyr Gln Thr Ser Asn Phe Arg Val Gln Pro
305                 310                 315                 320

Thr Glu Ser Ile Val Arg Phe Pro Asn Ile Thr Asn Leu Cys Pro Phe
                325                 330                 335

Gly Glu Val Phe Asn Ala Thr Arg Phe Ala Ser Val Tyr Ala Trp Asn
            340                 345                 350

Arg Lys Arg Ile Ser Asn Cys Val Ala Asp Tyr Ser Val Leu Tyr Asn
        355                 360                 365

Ser Ala Ser Phe Ser Thr Phe Lys Cys Tyr Gly Val Ser Pro Thr Lys
    370                 375                 380

Leu Asn Asp Leu Cys Phe Thr Asn Val Tyr Ala Asp Ser Phe Val Ile
385                 390                 395                 400

-continued

```
Arg Gly Asp Glu Val Arg Gln Ile Ala Pro Gly Gln Thr Gly Lys Ile
                405                 410                 415

Ala Asp Tyr Asn Tyr Lys Leu Pro Asp Asp Phe Thr Gly Cys Val Ile
            420                 425                 430

Ala Trp Asn Ser Asn Asn Leu Asp Ser Lys Val Gly Gly Asn Tyr Asn
        435                 440                 445

Tyr Leu Phe Arg Leu Phe Arg Lys Ser Asn Leu Lys Pro Phe Glu Arg
    450                 455                 460

Asp Ile Ser Thr Glu Ile Tyr Gln Ala Gly Ser Thr Pro Cys Asn Gly
465                 470                 475                 480

Val Glu Gly Phe Asn Cys Tyr Phe Pro Leu Gln Ser Tyr Gly Phe Gln
                485                 490                 495

Pro Thr Asn Gly Val Gly Tyr Gln Pro Tyr Arg Val Val Val Leu Ser
            500                 505                 510

Phe Glu Leu Leu His Ala Pro Ala Thr Val Cys Gly Pro Lys Lys Ser
        515                 520                 525

Thr Asn Leu Val Lys Asn Lys Cys Val Asn Phe Asn Phe Asn Gly Leu
    530                 535                 540

Thr Gly Thr Gly Val Leu Thr Glu Ser Asn Lys Lys Phe Leu Pro Phe
545                 550                 555                 560

Gln Gln Phe Gly Arg Asp Ile Ala Asp Thr Thr Asp Ala Val Arg Asp
                565                 570                 575

Pro Gln Thr Leu Glu Ile Leu Asp Ile Thr Pro Cys Ser Phe Gly Gly
            580                 585                 590

Val Ser Val Ile Thr Pro Gly Thr Asn Thr Ser Asn Gln Val Ala Val
        595                 600                 605

Leu Tyr Gln Asp Val Asn Cys Thr Glu Val Pro Val Ala Ile His Ala
    610                 615                 620

Asp Gln Leu Thr Pro Thr Trp Arg Val Tyr Ser Thr Gly Ser Asn Val
625                 630                 635                 640

Phe Gln Thr Arg Ala Gly Cys Leu Ile Gly Ala Glu His Val Asn Asn
                645                 650                 655

Ser Tyr Glu Cys Asp Ile Pro Ile Gly Ala Gly Ile Cys Ala Ser Tyr
            660                 665                 670

Gln Thr Gln Thr Asn Ser Pro Arg Arg Ala Arg Ser Val Ala Ser Gln
        675                 680                 685

Ser Ile Val Ala Tyr Thr Met Ser Leu Gly Ala Glu Asn Ser Val Ala
    690                 695                 700

Tyr Ser Asn Asn Ser Ile Ala Ile Pro Thr Asn Phe Thr Ile Ser Val
705                 710                 715                 720

Thr Thr Glu Ile Leu Pro Val Ser Met Thr Lys Thr Ser Val Asp Cys
                725                 730                 735

Thr Met Tyr Ile Cys Gly Asp Ser Thr Glu Cys Ser Asn Leu Leu Leu
            740                 745                 750

Gln Tyr Gly Ser Phe Cys Thr Gln Leu Asn Arg Ala Leu Thr Gly Ile
        755                 760                 765

Ala Val Glu Gln Asp Lys Asn Thr Gln Glu Val Phe Ala Gln Val Lys
    770                 775                 780

Gln Ile Tyr Lys Thr Pro Pro Ile Lys Asp Phe Gly Gly Phe Asn Phe
785                 790                 795                 800

Ser Gln Ile Leu Pro Asp Pro Ser Lys Pro Ser Lys Arg Ser Phe Ile
                805                 810                 815

Glu Asp Leu Leu Phe Asn Lys Val Thr Leu Ala Asp Ala Gly Phe Ile
```

-continued

```
        820                 825                 830

Lys Gln Tyr Gly Asp Cys Leu Gly Asp Ile Ala Ala Arg Asp Leu Ile
    835                 840                 845

Cys Ala Gln Lys Phe Asn Gly Leu Thr Val Leu Pro Pro Leu Leu Thr
    850                 855                 860

Asp Glu Met Ile Ala Gln Tyr Thr Ser Ala Leu Leu Ala Gly Thr Ile
865                 870                 875                 880

Thr Ser Gly Trp Thr Phe Gly Ala Gly Ala Ala Leu Gln Ile Pro Phe
                885                 890                 895

Ala Met Gln Met Ala Tyr Arg Phe Asn Gly Ile Gly Val Thr Gln Asn
            900                 905                 910

Val Leu Tyr Glu Asn Gln Lys Leu Ile Ala Asn Gln Phe Asn Ser Ala
        915                 920                 925

Ile Gly Lys Ile Gln Asp Ser Leu Ser Ser Thr Ala Ser Ala Leu Gly
    930                 935                 940

Lys Leu Gln Asp Val Val Asn Gln Asn Ala Gln Ala Leu Asn Thr Leu
945                 950                 955                 960

Val Lys Gln Leu Ser Ser Asn Phe Gly Ala Ile Ser Ser Val Leu Asn
                965                 970                 975

Asp Ile Leu Ser Arg Leu Asp Lys Val Glu Ala Glu Val Gln Ile Asp
            980                 985                 990

Arg Leu Ile Thr Gly Arg Leu Gln  Ser Leu Gln Thr Tyr  Val Thr Gln
        995                 1000                1005

Gln Leu  Ile Arg Ala Ala Glu  Ile Arg Ala Ser Ala  Asn Leu Ala
    1010                1015                1020

Ala Thr  Lys Met Ser Glu Cys  Val Leu Gly Gln Ser  Lys Arg Val
    1025                1030                1035

Asp Phe  Cys Gly Lys Gly Tyr  His Leu Met Ser Phe  Pro Gln Ser
    1040                1045                1050

Ala Pro  His Gly Val Val Phe  Leu His Val Thr Tyr  Val Pro Ala
    1055                1060                1065

Gln Glu  Lys Asn Phe Thr Thr  Ala Pro Ala Ile Cys  His Asp Gly
    1070                1075                1080

Lys Ala  His Phe Pro Arg Glu  Gly Val Phe Val Ser  Asn Gly Thr
    1085                1090                1095

His Trp  Phe Val Thr Gln Arg  Asn Phe Tyr Glu Pro  Gln Ile Ile
    1100                1105                1110

Thr Thr  Asp Asn Thr Phe Val  Ser Gly Asn Cys Asp  Val Val Ile
    1115                1120                1125

Gly Ile  Val Asn Asn Thr Val  Tyr Asp Pro Leu Gln  Pro Glu Leu
    1130                1135                1140

Asp Ser  Phe Lys Glu Glu Leu  Asp Lys Tyr Phe Lys  Asn His Thr
    1145                1150                1155

Ser Pro  Asp Val Asp Leu Gly  Asp Ile Ser Gly Ile  Asn Ala Ser
    1160                1165                1170

Val Val  Asn Ile Gln Lys Glu  Ile Asp Arg Leu Asn  Glu Val Ala
    1175                1180                1185

Lys Asn  Leu Asn Glu Ser Leu  Ile Asp Leu Gln Glu  Leu Gly Lys
    1190                1195                1200

Tyr Glu  Gln Tyr Ile Lys Trp  Pro Trp Tyr Ile Trp  Leu Gly Phe
    1205                1210                1215

Ile Ala  Gly Leu Ile Ala Ile  Val Met Val Thr Ile  Met Leu Cys
    1220                1225                1230
```

-continued

Cys Met Thr Ser Cys Cys Ser Cys Leu Lys Gly Cys Cys Ser Cys
1235 1240 1245

Gly Ser Cys Cys Lys Phe Asp Glu Asp Asp Ser Glu Pro Val Leu
1250 1255 1260

Lys Gly Val Lys Leu His Tyr Thr
1265 1270

<210> SEQ ID NO 17
<211> LENGTH: 232
<212> TYPE: PRT
<213> ORGANISM: Artificial Sequence
<220> FEATURE:
<223> OTHER INFORMATION: synthetic construct; IgG1 fragment

<400> SEQUENCE: 17

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Ala Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 18
<211> LENGTH: 233
<212> TYPE: PRT
<213> ORGANISM: Artificial Sequence
<220> FEATURE:
<223> OTHER INFORMATION: synthetic construct; IgG2a fragment

<400> SEQUENCE: 18

Glu Pro Arg Gly Pro Thr Ile Lys Pro Cys Pro Pro Cys Lys Ser Pro
1 5 10 15

Ala Pro Asn Leu Leu Gly Gly Pro Ser Val Phe Ile Phe Pro Pro Lys

```
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Ala Phe Ala Cys Ala Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230


<210> SEQ ID NO 19
<211> LENGTH: 233
<212> TYPE: PRT
<213> ORGANISM: Artificial Sequence
<220> FEATURE:
<223> OTHER INFORMATION: synthetic construct; IgG2a fragment

<400> SEQUENCE: 19

Glu Pro Arg Gly Pro Thr Ile Lys Pro Ser Pro Pro Ser Lys Ser Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Ala Phe Ala Cys Ala Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Pro Glu Glu Glu Met
    130                 135                 140

Thr Lys Lys Gln Val Thr Leu Thr Cys Met Val Thr Asp Phe Met Pro
```

```
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230
```

<210> SEQ ID NO 20
<211> LENGTH: 27
<212> TYPE: PRT
<213> ORGANISM: Artificial Sequence
<220> FEATURE:
<223> OTHER INFORMATION: synthetic construct; foldon sequence

<400> SEQUENCE: 20

```
Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25
```

<210> SEQ ID NO 21
<211> LENGTH: 81
<212> TYPE: DNA
<213> ORGANISM: Artificial Sequence
<220> FEATURE:
<223> OTHER INFORMATION: synthetic construct; foldon sequence

<400> SEQUENCE: 21

```
ggctacatcc ccgaggcccc cagagacggc caggcctacg tgagaaagga cggcgagtgg     60

gtgctgctga gcaccttcct g                                               81
```

<210> SEQ ID NO 22
<211> LENGTH: 32
<212> TYPE: PRT
<213> ORGANISM: Artificial Sequence
<220> FEATURE:
<223> OTHER INFORMATION: synthetic construct; GCN4pII trimerization motif

<400> SEQUENCE: 22

```
Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Val
            20                  25                  30
```

<210> SEQ ID NO 23
<211> LENGTH: 6
<212> TYPE: PRT
<213> ORGANISM: Artificial Sequence
<220> FEATURE:
<223> OTHER INFORMATION: synthetic construct; GS linker

<400> SEQUENCE: 23

```
Gly Ser Gly Ser Gly Ser
1               5
```

<210> SEQ ID NO 24

-continued

```
<211> LENGTH: 14
<212> TYPE: PRT
<213> ORGANISM: Artificial Sequence
<220> FEATURE:
<223> OTHER INFORMATION: synthetic construct; GS linker

<400> SEQUENCE: 24

Gly Ser Gly Gly Gly Gly Ser Gly Gly Gly Gly Ser Gly Ser
1               5                   10


<210> SEQ ID NO 25
<211> LENGTH: 15
<212> TYPE: PRT
<213> ORGANISM: Artificial Sequence
<220> FEATURE:
<223> OTHER INFORMATION: synthetic construct; signal peptide

<400> SEQUENCE: 25

Met Phe Val Phe Leu Val Leu Leu Pro Leu Val Ser Ser Gln Cys
1               5                   10                  15
```

COMPOSITIONS AND METHODS FOR MUCOSAL VACCINATION AGAINST SARS-COV-2

CROSS-REFERENCE TO RELATED APPLICATIONS

This application claims the benefit of U.S. Provisional Patent Application No. 62/981,873, filed on Feb. 26, 2020, which is incorporated by reference herein in its entirety.

STATEMENT REGARDING FEDERALLY SPONSORED RESEARCH

This invention was made with government support under 58-8042-9-024 awarded by the Agricultural Research Service, and R01 AI146063, and R21 AI130712 awarded by the National Institutes of Health. The government has certain rights in the invention.

REFERENCE TO SEQUENCE LISTING

The Sequence Listing submitted Jan. 25, 2024 as a text file named "36429_0026U2_Updated_Sequence_Listing.txt," created on Jan. 16, 2024, and having a size of 124,337 bytes is hereby incorporated by reference pursuant to 37 C.F.R. § 1.52 (e) (5).

BACKGROUND

COVID-19, the disease caused by the virus SARS-COV-2, is extremely infectious and sustainable in the community. The virus spreads mainly through respiratory droplets, possible aerosol, produced when an infected person coughs or sneezes. These droplets or aerosols can land in the mouths or noses of people who are nearby or possibly inhaled into the lungs. The highly contagious nature is probably due to the virus spreading via asymptomatic patients. Although most patients are not severe, the virus can cause acute, highly lethal pneumonia with a 2-10 day incubation period in the elderly or people underlying medical conditions. Although children infected with SARS-COV-2 have less symptoms, they can spread the virus easily to others. The SARS-COV-2 virus infects respiratory epithelial cells through its Spike(S) binding to angiotensin-converting enzyme 2 (ACE2) receptor. Using Spike(S) protein, the SARS-COV-2 virus binds to ACE2 receptor in nasal, bronchial, alveolar, and other epithelial cells. During infection, the S protein is cleaved into S1 and S2 subunits by host proteases. S1 mainly contains the receptor-binding domain (RBD) which allows viruses to directly bind to the ACE2, S2 likely mediates membrane fusion with the help of a protease TMPRSS2 in cells.

The neonatal Fc Receptor (FcRn) plays a crucial role in transporting IgG antibody across the polarized epithelial cells lining the respiratory, intestinal, genital tract and the placenta. FcRn expresses in cell surface or resides within low-pH endosomes. Normally, IgG enters cells via pinocytotic vesicles that fuse with endosomes. IgG which binds to FcRn is transported to the basolateral surface and released into the submucosa. It has been shown that FcRn in dendritic cells (DCs) and macrophages enhances antigen presentation to CD4 T helper, or cross-presentation to CD8 T cells. FcRn in all mammals are structurally and functionally similar.

Presently, most vaccines against respiratory infections are designed for delivery via the muscle or skin but are intended to protect the lung. Parenteral delivery elicits relatively poor immunity in the respiratory tract even though they often induce robust systemic immunity. A partial reason is that parenteral immunization fails to induce strong mucosal antibody and cell-mediated immunity including T and B cells that reside in the lung. Since SARS-COV-2 viruses infect the upper or lower respiratory tract and asymptomatic infections frequently occur, the development of a safe and effective mucosal vaccine to prevent the infection and possibly reinfection in the long term is urgently needed. Ideally, a mucosal vaccine mimics the route of natural viral exposure and engenders beneficial nasal and lung immunity. This goal can be best achieved by direct delivery of the SARS-COV-2 vaccine antigen via the intranasal route.

BRIEF SUMMARY

Described herein are compositions and methods for using the FcRn to deliver SARS-CoV-2 spike antigens to induce protective immunity against SARS-COV-2 virus infection.

Disclosed are peptides comprising a monomeric Fc fragment of an immunoglobulin recognized by a FcRn; SARS-COV-2 antigen; and a trimerization domain. In some aspects, the SARS-COV-2 antigen can be a SARS-COV-2 spike protein. Thus, disclosed are peptides comprising a monomeric Fc fragment of an immunoglobulin recognized by a FcRn; SARS-CoV-2 spike protein; and a trimerization domain.

Disclosed are peptide complexes comprising three of the disclosed peptides. For example, disclosed are peptide complexes comprising three peptides, wherein each of the three peptides comprises a monomeric Fc fragment of an immunoglobulin recognized by a FcRn; SARS-COV-2 antigen; and a trimerization domain.

Disclosed are nucleic acid sequences capable of encoding any of the peptides disclosed herein.

Disclosed are compositions comprising any of the disclosed peptides, peptide complexes, nucleic acid sequences, or vectors. In some instances, disclosed are compositions comprising a monomeric Fc fragment of an immunoglobulin recognized by a FcRn; a SARS-CoV-2 antigen; and a trimerization domain.

Disclosed are methods for eliciting a protective immune response against SARS-CoV-2 comprising administering to a subject an effective amount of a composition comprising a monomeric Fc fragment of an immunoglobulin recognized by a FcRn; a SARS-COV-2 antigen; and a trimerization domain, wherein the administering is to a mucosal epithelium.

Disclosed are methods of treating a subject exposed to SARS-COV-2 or at risk of being exposed to SARS-COV-2 comprising administering to a subject an effective amount of a composition comprising a monomeric Fc fragment of an immunoglobulin recognized by a FcRn; a SARS-COV-2 antigen; and a trimerization domain, wherein the administering is to a mucosal epithelium.

Disclosed are methods of reducing SARS-COV-2 viral titers in a subject infected with SARS-COV-2 comprising administering to a subject an effective amount of a composition comprising a monomeric Fc fragment of an immunoglobulin recognized by a FcRn; a SARS-CoV-2 antigen; and a trimerization domain, wherein the administering is to a mucosal epithelium.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1:
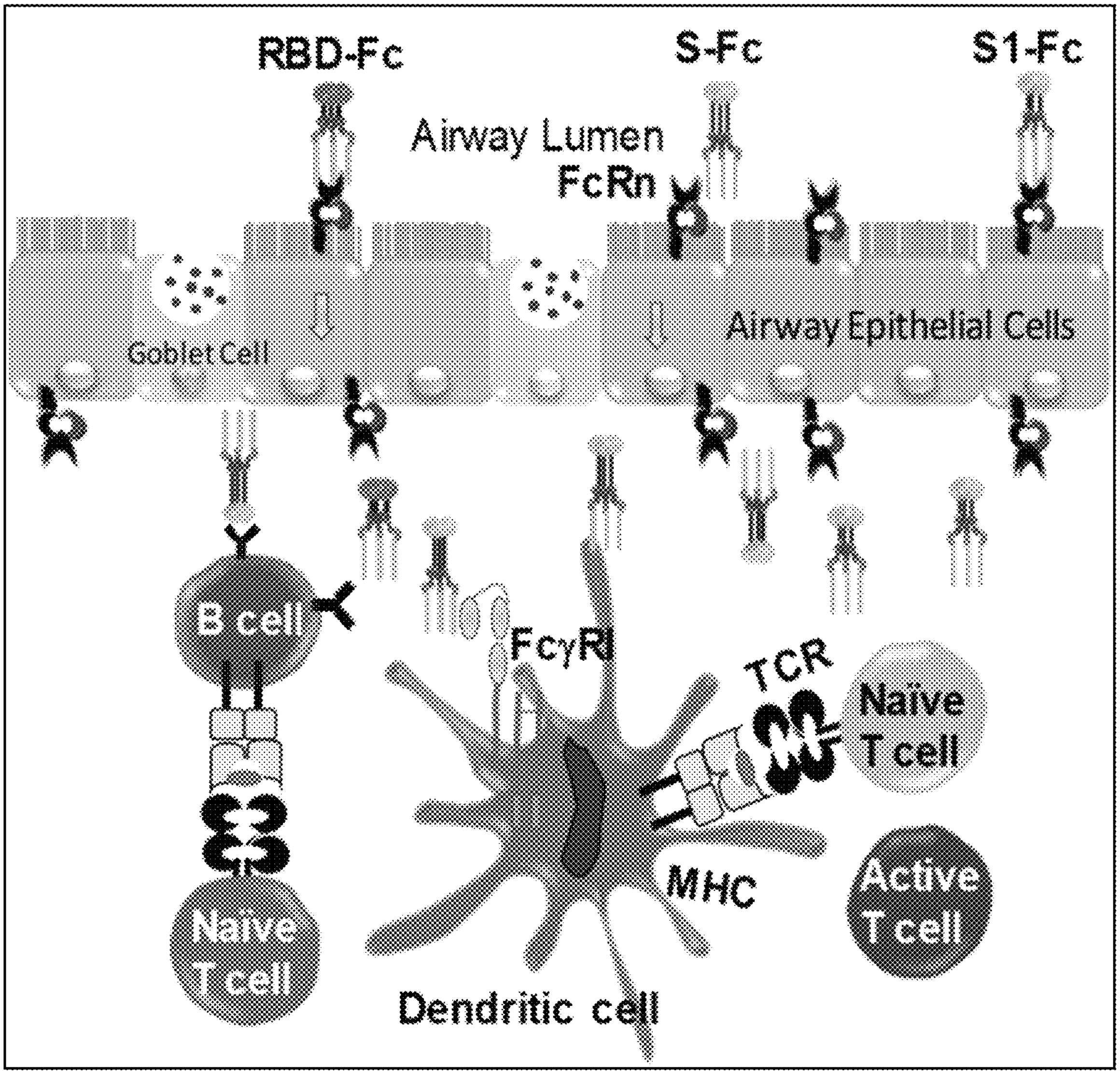
FIG. 1 shows a schematic representing a proposed model of FcRn-mediated transfer of SARS-COV-2 vaccine antigens across a respiratory epithelial barrier and target to mucosal antigen presenting cells (APCs) (e.g. dendritic cells) and B cells.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the amino acids are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a peptide" includes a plurality of such peptides, reference to "the composition" is a reference to one or more compositions and equivalents thereof known to those skilled in the art, and so forth.

As used herein, the term "therapeutically effective amount" means an amount of a therapeutic, prophylactic, and/or diagnostic agent that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition.

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition (e.g. SARS-COV-2 infection). For example, "treating" SARS-COV-2 may refer to inhibiting survival, growth, and/or spread of the virus. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, "subject" refers to the target of administration, e.g. an animal. Thus the subject of the disclosed methods can be a vertebrate, such as a mammal. For example, the subject can be a human. The term does not denote a particular age or sex. Subject can be used interchangeably with "individual" or "patient".

The term 'peptide' refers to a polymer of amino acids and does not refer to a specific length of the product; thus, polypeptides, oligopeptides, and proteins are included within the definition of peptide. This term also does not refer to or exclude post-expression modifications of the peptide, for example, glycosylations, acetylations, phosphorylations and the like. Included within the definition are, for example, peptides containing one or more analogues of an amino acid (including, for example, unnatural amino acids, PNA, etc.), peptides with substituted linkages, as well as other modifications known in the art, both naturally occurring and non-naturally occurring.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

As used herein, "coronavirus" refers to a group of RNA viruses of the subfamily Orthocoronavirinae, in the family Coronaviridae, order Nidovirales, and realm Riboviria. They are enveloped viruses with a positive-sense single-stranded RNA genome and a nucleocapsid of helical symmetry. The genome size of coronaviruses ranges from approximately 26 to 32 kilobases, one of the largest among RNA viruses. They have characteristic club-shaped spikes that project from their surface, which in electron micrographs create an image reminiscent of the solar corona, from which their name derives. In some aspects, the coronavirus is Middle East respiratory syndrome coronavirus (MERS-COV), Human Coronavirus-Erasmus Medical Centre (HCoV-EMC), SARS-COV, or SARS-COV-2.

The term "subject" refers to the target of administration, e.g. an animal. Thus, the subject of the disclosed methods can be a vertebrate, such as a mammal. For example, the subject can be a human. The term does not denote a particular age or sex. Subject can be used interchangeably with "individual" or "patient." For example, the subject of administration can mean the recipient of the alternating electrical field.

By "prevent" is meant to minimize or decrease the chance that a subject will develop a coronavirus infection.

As used herein, the terms "administering" and "administration" refer to any method of providing a therapeutic, such as an antiviral agent or coronavirus therapeutic (e.g., a peptide or peptide complex as disclosed herein), to a subject.

Such methods are well known to those skilled in the art and include, but are not limited to: oral administration, transdermal administration, administration by inhalation, nasal administration, topical administration, intravaginal administration, ophthalmic administration, intramural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In an aspect, the skilled person can determine an efficacious dose, an efficacious schedule, or an efficacious route of administration so as to treat a subject. In some aspects, administering comprises exposing. Thus, in some aspects, exposing a subject to alternating electrical fields means administering alternating electrical fields to the subject.

"Optional" or "optionally" means that the subsequently described event, circumstance, or material may or may not occur or be present, and that the description includes instances where the event, circumstance, or material occurs or is present and instances where it does not occur or is not present.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Coronaviruses

Coronaviruses are a group of RNA viruses that cause diseases in mammals and birds. In humans and birds, they cause respiratory tract infections that can range from mild to lethal. Mild illnesses in humans include some cases of the common cold (which is also caused by other viruses, predominantly rhinoviruses), while more lethal varieties can cause SARS, MERS, and COVID-19. In cows and pigs they cause diarrhea, while in mice they cause hepatitis and encephalomyelitis.

Coronaviruses are members of the subfamily Orthocoronavirinae, in the family Coronaviridae, order Nidovirales, and realm Riboviria. They are enveloped viruses with a positive-sense single-stranded RNA genome and a nucleocapsid of helical symmetry. The genome size of coronaviruses ranges from approximately 26 to 32 kilobases, one of the largest among RNA viruses. They have characteristic club-shaped spikes that project from their surface, which in electron micrographs create an image reminiscent of the solar corona, from which their name derives.

Over the past two decades, emerging pathogenic coronaviruses capable of causing life-threatening disease in humans and animals have been identified, namely severe acute respiratory syndrome coronavirus (SARS-COV) and Middle Eastern respiratory syndrome coronavirus (MERS-COV). In December 2019, the Wuhan Municipal Health Committee (Wuhan, China) identified an outbreak of viral pneumonia cases of unknown cause. Coronavirus RNA was identified in some of these patients. This novel coronavirus has been named SARS-CoV-2, and the disease caused by this virus has been named COVID-19. Currently there are approximately 50 million confirmed cases of COVID-19 and over 1.2 million deaths globally.

Individuals of all ages are at risk for infection and severe disease. However, the probability of serious COVID-19 disease is higher in people aged ≥60 years, those living in a nursing home or long-term care facility, and those with chronic medical conditions. The spectrum of illness can range from asymptomatic infection to severe pneumonia with acute respiratory distress syndrome (ARDS) and death. Although COVID-19 patients can present with many different symptoms the main symptoms are fever, cough or shortness of breath. The abnormalities seen in chest X-rays vary, but bilateral multi-focal opacities are the most common. The abnormalities seen in computed tomography (CT) of the chest also vary, but the most common are bilateral peripheral ground-glass opacities, with areas of consolidation developing later in the clinical course. In the early phase of the disease and in an asymptomatic presentation the imaging of both X-ray and CT can be normal. Virologic testing (i.e., using a molecular diagnostic or antigen test to detect SARS-COV-2) is recommended by the NIH for diagnosing SARS-COV-2 in patients with suspected COVID-19 symptoms.

COVID-19 patients can be grouped into the following groups by illness severity-asymptomatic or presymptomatic, mild, moderate, severe and critical illness, where patients with severe illness are individuals who have respiratory frequency >30 breaths per minute, $SpO2 <94\%$ on room air at sea level, ratio of arterial partial pressure of oxygen to fraction of inspired oxygen (PaO2/FiO2)<300 mmHg, or lung infiltrates >50%. The management of a COVID-19 patient with severe illness includes pulmonary imagining and ECG, if indicated. Laboratory evaluation includes a complete blood count (CBC) with differential and a metabolic profile, including liver and renal function tests. Measurements of inflammatory markers such as C-reactive protein (CRP), D-dimer, and ferritin, while not part of standard care, may have prognostic value.

Although it has been almost a year since the first case of COVID-19 pneumonia, current treatment options are limited and involve the treatment of symptoms, supportive care, isolation, and experimental measures. Therefore, there is an urgent unmet need to develop new therapies for the treatment of COVID-19 and other coronavirus infections.

C. Peptides

1. Peptides Comprising a Trimerization Domain

Disclosed are peptides comprising a monomeric Fc fragment of an immunoglobulin recognized by a FcRn; a coronavirus antigen; and a trimerization domain. In some aspects, the coronavirus antigen can be any coronavirus spike protein, or antigenic fragment thereof. In some aspects, the coronavirus is Middle East respiratory syndrome coronavirus (MERS-COV), Human Coronavirus-Erasmus Medical Centre (HCoV-EMC), SARS-COV, or SARS-COV-2. Thus, in some aspects, the coronavirus spike protein can be a MERS-COV, HCoV-EMC, SARS-CoV, or SARS-COV-2 spike protein, or antigenic fragment thereof.

Disclosed are peptides comprising a monomeric Fc fragment of an immunoglobulin recognized by a FcRn; SARS-COV-2 antigen; and a trimerization domain. In some aspects, the SARS-COV-2 antigen can be a SARS-COV-2 spike protein. Thus, disclosed are peptides comprising a monomeric Fc fragment of an immunoglobulin recognized by a FcRn; SARS-CoV-2 spike protein; and a trimerization domain.

In some instances, the monomeric Fc fragment of an immunoglobulin recognized by a FcRn is conjugated to the amino or carboxy terminal end of a trimerization domain. In some aspects, the SARS-COV-2 antigen is conjugated to the amino or carboxy terminal end of a trimerization domain. In some aspects, the monomeric Fc fragment of an immunoglobulin recognized by a FcRn is conjugated to the C-terminal end of a trimerization domain and the N-terminal end of the trimerization domain is conjugated to the C-terminal end of the SARS-COV-2 antigen. In some instances, the monomeric Fc fragment of an immunoglobulin recognized by a FcRn is conjugated to the amino or carboxy terminal end of a SARS-COV-2 antigen.

As described herein, the disclosed peptides can comprise a monomeric Fc fragment of an immunoglobulin recognized by a FcRn; a coronavirus antigen; and a trimerization domain. In some aspects, the order, from the N-terminus to the C-terminus of the peptide can be 1) coronavirus antigen, trimerization domain, monomeric Fc fragment of an immunoglobulin recognized by a FcRn; 2) monomeric Fc fragment of an immunoglobulin recognized by a FcRn, trimerization domain, coronavirus antigen; or 3) monomeric Fc fragment of an immunoglobulin recognized by a FcRn, coronavirus antigen, trimerization domain.

The conjugation can be direct or indirect. Indirect conjugation can be due to the presence of a linker, for example, a linker can be present in between the SARS-COV-2 antigen and a trimerization domain.

Disclosed are peptides encoded by one or more of the nucleic acid sequences provided herein.

i. Monomeric Fc Fragment

A monomeric Fc fragment of an immunoglobulin recognized by a FcRn, as disclosed herein, can be any Fc fragment that can be recognized by a FcRn. In some aspects, monomeric Fc fragment of an immunoglobulin recognized by a FcRn can comprise only the Fc portion of an immunoglobulin.

The disclosed monomeric Fc fragments of an immunoglobulin recognized by a FcRn are altered or mutated in order to make them monomeric. The monomeric Fc fragments of an immunoglobulin recognized by a FcRn cannot form dimers as found in an antibody. In some instances the monomeric Fc fragment of an immunoglobulin comprises a mutation in the Fc region of an immunoglobulin recognized by FcRn sequence that results in the prevention of dimer formation. In some aspects, the monomeric Fc fragment of an immunoglobulin recognized by a FcRn comprises at least one mutation in a cysteine residue responsible for dimer formation. For example, mutations can be at one or more of positions 226 and 229 of the full length sequence of the wild type sequence of human IgG1. In some aspects, the Cys at positions 226 and 229 of full length human wild type IgG1 can be mutated to Ser in order to prevent dimer formation. In some aspects, the cysteine mutations to serine can be found at positions 11 and 14 of a sequence comprising only the hinge region, CH2 and CH3 domains of wild type IgG. For example, the cysteine mutations to serine can be found at positions 11 and 14 of SEQ ID NO: 7. In some aspects, positions 11 and 14 of SEQ ID NO:7 are located in the hinge region of monomeric Fc fragments of an immunoglobulin recognized by a FcRn.

In some instances, corresponding mutations can be made in other IgG Fc fragments and Fc fragments from other isotypes in order to mutate the cysteine residues responsible for dimer formation. In some instances, other mutations can be made throughout the Fc fragment of an immunoglobulin recognized by a FcRn so long as the FcRn binding region is not affected.

In some aspects, the C1q binding site can be ablated in the monomeric Fc fragment. This can be effective to help avoid clearance of the Fc fragments via the complement pathway and thus allowing the disclosed peptides comprising a monomeric Fc fragment to remain in a subject and provide their therapeutic effect. In some aspects, C1q is known to bind to the CH2 domain of an immunoglobulin, particularly IgG. In some aspects, substituting the lysine at position 322 can ablate or eliminate the complement C1q binding site. For example, replacing Lys322 of full length human IgG with an Ala residue can ablate or eliminate the complement C1q binding site. In some aspects, replacing one or more of Glu318, Lys320, and Lys322 of full length mouse IgG with an Ala residue can ablate or eliminate the complement C1q binding site. In some aspects, ablating C1q binding to the disclosed monomeric Fc fragments comprises mutation position 107 of a monomeric Fc fragment of an immunoglobulin recognized by a FcRn. For example, a mutation of lysine to alanine shown at position 107 of SEQ ID NO:7 can ablate C1q binding to a human monomeric Fc fragment of an immunoglobulin recognized by a FcRn.

In some aspects, the FcRn binding sites are known to be His310 and His433 or His310/Gln311 (HQ) and His433/Asn434 (HN) of full length wild type IgG. The region of the Fc-fragment of IgG that binds to the FcRn receptor in humans has been described based upon X-ray crystallography (Burmaister, W. P. et al., Nature, 1994; 372:379-378; incorporated by reference in its entirety herein). The major contact area of Fc with the FcRn receptor is near the junction of the CH2 and CH3 domains. Potential contacts are residues 248, 250-257, 272, 285, 288, 290-291, 308-311 and 314 in CH2 and 385-387, 428 and 433-436 in CH3. In some aspects, no mutations would be present in the FcRn binding sites. Given the foregoing information, those of ordinary skill in the art will readily recognize that the monomeric Fc fragment of IgG can be modified according to well-recognized procedures such as site-directed mutagenesis and the like to yield modified monomeric Fc fragments or portions thereof that will be bound by the FcRn receptor. Such modifications include modifications remote from the FcRn contact sites as well as modifications within the contact sites that preserve or even enhance binding.

In some aspects, the monomeric Fc fragment of an immunoglobulin recognized by a FcRn can be derived from any isotype that binds FcRn. The Fc-fragment should be chosen from an immunoglobulin known to bind the FcRn in the mucosa of the subject receiving the antigen-Fc vaccine. Immunoglobulin subclasses recognized by FcRn in different epithelial mucosa of animal subjects are known to a person in the art and can be found in Ober, R. J. et al, 2001, Int. Immunol. 13, 1551-9, incorporated by reference in its entirety herein. In some aspects, the monomeric Fc fragment of an immunoglobulin recognized by a FcRn is derived from a mammalian immunoglobulin. For example, the monomeric Fc fragment of an immunoglobulin recognized by a FcRn can be a human immunoglobulin sequence.

In some aspects, the amino acid sequence of a monomeric Fc fragment of a human IgG1 can be

```
                                   (SEQ ID NO: 7)
EPKSCDKTHTsPPsPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCaVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

or a variant thereof. In some aspects, the variant can a sequence 50%, 55%, 65%, 70%, 75%, 80%, 90%, 95%, 96%, 97%, 98%, or 99% identical to the sequence of SEQ ID NO: 7. The two cysteine to serine mutations are shown at positions 11 and 14. A lysine to alanine mutation is shown at position 107. The cysteine mutations allow for the Fc fragment to remain monomeric and not dimerize with another Fc fragment. The lysine to alanine mutation ablates C1q binding to the Fc fragment.

In some aspects, the amino acid sequence of a monomeric Fc fragment of a mouse IgG2a can be (SEQ ID NO: 19)

EPRGPTIKP<u>S</u>PP<u>S</u>K<u>S</u>PAPNLLGGPSVFIFPPKIKDVLMISLSPIVTCVV

VDVSEDDPDVQISWFVNNVEVHTAQTQTHREDYNSTLRVVSALPIQHQD

WMSGKAFACAVNNKDLPAPIERTISKPKGSVRAPQVYVLPPPEEEMTKK

QVTLTCMVTDFMPEDIYVEWTNNGKTELNYKNTEPVLDSDGSYFMYSKL

RVEKKNWVERNSYSCSVVHEGLHNHHTTKSFSRTPGK or a sequence 50%, 55%, 65%, 70%, 75%, 80%, 90%, 95%, 96%, 97%, 98%, or 99% identical to the sequence of (SEQ ID NO:19). The bold underlined amino acids represent a mutation from cysteine to serine to generate a single chain Fc.

In some aspects, the monomeric Fc fragment of an immunoglobulin recognized by a FcRn comprises a full length Fc region of an immunoglobulin. In some aspects, the monomeric Fc fragment of an immunoglobulin recognized by a FcRn comprises at least the CH2 and CH3 domains of a Fc region of an immunoglobulin. For example, the monomeric Fc fragment of an immunoglobulin recognized by a FcRn comprises one or more of a full length CH2 and CH3 domain of IgG. In some aspects, the monomeric Fc fragment of an immunoglobulin recognized by a FcRn comprises at least a portion of the one or more CH2 and CH3 domains so long as the portions of the one or more CH2 and CH3 domains retains the ability to be recognized by FcRn.

In some instances, the monomeric Fc fragment of an immunoglobulin recognized by a FcRn is conjugated to the amino or carboxy terminal end of SARS-COV-2 antigen. For example, the SARS-COV-2 antigen can be the spike protein or a fragment thereof. In some instances, the monomeric Fc fragment of an immunoglobulin recognized by a FcRn is conjugated to the amino or carboxy terminal end of a trimerization domain. For example, the trimerization domain can be foldon. The conjugation can be direct or indirect. Indirect conjugation can be due to the presence of a linker in between the SARS-COV-2 antigen or trimerization domain and the monomeric Fc fragment of an immunoglobulin recognized by a FcRn. Indirect conjugation can be due to the presence of another peptide in between the SARS-CoV-2 antigen or trimerization domain and the monomeric Fc fragment of an immunoglobulin recognized by a FcRn.

In some aspects, the monomeric Fc fragment of an immunoglobulin recognized by a FcRn can be derived from IgG. In some aspects, the IgG can be any IgG subtype. For example, the monomeric Fc fragment of an immunoglobulin recognized by a FcRn can be derived from IgG1, IgG2, IgG3, or IgG4.

ii. Trimerization Domain

The disclosed peptides have a trimerization domain.

The SARS-COV-2 S protein naturally exists as a trimer. Thus, disclosed herein are trimerization domains that allow the disclosed peptides, comprising one or more of the SARS-COV-2 S proteins, to trimerize. For example, three of the disclosed peptides can trimerize to form a peptide complex as disclosed herein.

In some instances, the trimerization domain is a T4 bacteriophage fibritin trimerization domain. For example, the T4 bacteriophage fibritin trimerization domain can be foldon which is present at the C-terminus of T4 bacteriophage fibritin. In some instances, the wild type amino acid sequence of foldon is GYIPEAPRDGQAYVRKDGEWVLLSTFL (SEQ ID NO: 20). In some instances, the amino acid sequence of foldon is 50%, 55%, 65%, 70%, 75%, 80%, 90%, 95%, 96%, 97%, 98%, or 99% identical to the wild type foldon sequence. In some aspects, the nucleic acid sequence of foldon can be represented by the sequence

```
GGCTACATCCCCGAGGCCCCCAGAGACGGCCAGGCCTACGTGAGAAAGGA

CGGCGAGTGGGTGCTGCTGAGCACCTTCCTG. (SEQ ID NO: 21)
```

In some instances, the trimerization domain can be, but is not limited to the transcription factor GCN4pII trimerization motif (MKQIEDKIEEILSKIYHIENEIARIKKLIGEV; SEQ ID NO:22), or human collagen XV trimerization domain. In some instances, the trimerization domain can be an amino acid sequence that is 50%, 55%, 65%, 70%, 75%, 80%, 90%, 95%, 96%, 97%, 98%, or 99% identical to transcription factor GCN4pII trimerization motif or human collagen XV trimerization domain.

In some aspects, the trimerization domain is between the monomeric Fc fragment recognized by FcRn and the SARS-COV-2 antigen. In some aspects, the trimerization domain is on the C-terminal end of the SARS-COV-2 S protein. In some aspects, the trimerization domain is on the N-terminal end of the monomeric Fc fragment recognized by FcRn.

iii. Coronavirus Antigen

In some aspects, the disclosed peptides can comprise a monomeric Fc fragment recognized by FcRn, a trimerization domain, and a coronavirus antigen. In some aspects, a coronavirus antigen can be any region of a coronavirus that can generate an immune response. In some aspects, a coronavirus antigen can be all or a portion of the coronavirus spike(S) protein. In some aspects, the coronavirus S protein is the soluble portion of the coronavirus S protein. For example, the transmembrane domain and cytoplasmic domain are not present in the soluble portion of the coronavirus S protein. In some aspects, the coronavirus is Middle East respiratory syndrome coronavirus (MERS-COV), Human Coronavirus-Erasmus Medical Centre (HCoV-EMC), SARS-COV, or SARS-COV-2. Thus, in some aspects, the coronavirus spike protein can be a MERS-COV, HCoV-EMC, SARS-COV, or SARS-COV-2 spike protein, or antigenic fragment thereof.

In some aspects, the disclosed peptides can comprise a monomeric Fc fragment recognized by FcRn, a trimerization domain, and a SARS-COV-2 antigen. In some aspects, a SARS-COV-2 antigen can be any region of SARS-COV-2 that can generate an immune response. In some aspects, a SARS-COV-2 antigen can be all or a portion of the SARS-COV-2 S protein. In some aspects, the SARS-COV-2 S protein is the soluble portion of the SARS-COV-2 S protein. For example, the transmembrane domain and cytoplasmic domain are not present in the soluble portion of the SARS-COV-2 S protein.

In some aspects, a SARS-COV-2 S protein can be derived from wild type SARS-CoV-2 or from a variant strain, such as, but not limited to, the variants of D614G (originally found in China/Germany), B.1.1.7 or 201/501Y.V1 (originally found in the United Kingdom), B.1.351 or 20H/501.V2 (originally found in South Africa), P.1 or 20J/501Y V3 (originally found in Japan/Brazil), 20C/S: 452R (originally found in California), and Cluster 5 Variant (originally found in Denmark).

In some aspects, the soluble portion of the SARS-COV-2 S protein is amino acids 1-1213 of the full length wild type S protein. Specifically, the soluble portion of the SARS-COV-2 S protein comprises the sequence (SEQ ID NO: 8)

MFVFLVLLPLVSSQCVNLTTRTQLPPAYTNSFTRGVYYPDKVFRSSVLHSTQDLFLPFFS

NVTWFHAIHVSGTNGTKRFDNPVLPFNDGVYFASTEKSNIIRGWIFGTTLDSKTQSLLIV

NNATNVVIKVCEFQFCNDPFLGVYYHKNNKSWMESEFRVYSSANNCTFEYVSQPFLMD

LEGKQGNFKNLREFVFKNIDGYFKIYSKHTPINLVRDLPQGFSALEPLVDLPIGINITRFQ

TLLALHRSYLTPGDSSSGWTAGAAAYYVGYLQPRTFLLKYNENGTITDAVDCALDPLS

ETKCTLKSFTVEKGIYQTSNFRVQPTESIVRFPNITNLCPFGEVFNATRFASVYAWNR

KRISNCVADYSVLYNSASFSTFKCYGVSPTKLNDLCFTNVYADSFVIRGDEVRQIAP

GQTGKIADYNYKLPDDFTGCVIAWNSNNLDSKVGGNYNYLYRLFRKSNLKPFERD

ISTEIYQAGSTPCNGVEGFNCYFPLQSYCFQPTNGVGYQPYRVVVLSFELLHAPAT

VCGFKKSTNLVKNKCVNFNFNGLTGTGVLTESNKKFLPFQQFGRDIADTTDAVRDPQ

TLEILDITPCSFGGVSVITPGTNTSNQVAVLYQDVNCTEVPVAIHADQLTPTWRVYSTGS

NVFQTRAGCLIGAEHVNINSYECDIPIGAGICASYQTQTNSPRRAASVASQSHAYTMSLG

AENSVAYSNNSIAIPTNFTISVTTEILPVSMTKTSVDCTMYICGDSTECSNLLLQYGSFCT

QLNRALTGIAVEQDKNTQEVFAQVKQIYKTPPIKDFGGFNFSQILPDPSKPSKASFIEDLL

FNKVTLADAGFIKQYGDCLGDIAARDLICAQKFNGLTVLPPLLTDEMIAQYTSALLAGTI

TSGWTFGAGAALQIPFAMQMAYRFNGIGVTQNVLYENQKLIANQFNSAIGKIQDSLSST

ASALGKLQDVVNQNAQALNTLVKQLSSNFGAISSVLNDILSRLDPPEAEVQIDRLITGRL

QSLQTYVTQQLIRAAEIRASANLAATKIVISECVLGQSKRVDFCGKGYHLMSFPQSAPHG

VVFLHVTYVPAQEKNFTTAPAICHDGKAHFPREGVFVSNGTHWFVTQRNFYEPQIITTD

NTFVSGNCDVVIGIVNNTVYDPLQPELDSFKEELDKYFKNHTSPDVDLGDISGINASVVN

IQKEIDRLNEVAKNLNESLIDLQELGKYEQYIKWP or a variant thereof. In some aspects, the variant can be a sequence 50%, 55%, 65%, 70%, 75%, 80%, 90%, 95%, 96%, 97%, 98%, or 99% identical to the sequence of SEQ ID NO:8. The underlined sequence represents a native signal peptide of S protein. The bold shaded sequence represents the RBD of S1. The bold underline sequence represents the mutated S1/S2 cleavage site (R685A in italics, no change in S686). The bold letter and bold underline sequence represents a mutation at the S2' cleavage site (R816A in italics, no change in S817). The bold, italics, and shaded sequence represents K986P and V987P mutations which allow the S protein to keep the Pre-fusion conformation.

In some aspects, the SARS-COV-2 S protein is the soluble portion of the D614G variant S protein. Specifically, the S protein of the D614G variant can comprise the sequence (SEQ ID NO: 11)

MFVFLVLLPLVSSQCVNLTTRTQLPPAYTNSFTRGVYYPDKVFRSSVLHS
TQDLFLPFFSNVTWFHAIHVSGTNGTKRFDNPVLPFNDGVYFASTEKSNI
IRGWIFGTTLDSKTQSLLIVNNATNVVIKVCEFQFCNDPFLGVYYHKNNK
SWMESEFRVYSSANNCTFEYVSQPFLMDLEGKQGNFKNLREFVFKNIDGY
FKIYSKHTPINLVRDLPQGFSALEPLVDLPIGINITRFQTLLALHRSYLT
PGDSSSGWTAGAAAYYVGYLQPRTFLLKYNENGTITDAVDCALDPLSETK
CTLKSFTVEKGIYQTSNFRVQPTESIVRFPNITNLCPFGEVFNATRFASV
YAWNRKRISNCVADYSVLYNSASFSTFKCYGVSPTKLNDLCFTNVYADSF
VIRGDEVRQIAPGQTGKIADYNYKLPDDFTGCVIAWNSNNLDSKVGGNYN
YLYRLFRKSNLKPFERDISTEIYQAGSTPCNGVEGFNCYFPLQSYGFQPT
NGVGYQPYRVVVLSFELLHAPATVCGPKKSTNLVKNKCVNFNFNGLTGTG
VLTESNKKFLPFQQFGRDIADTTDAVRDPQTLEILDITPCSFGGVSVITP
GTNTSNQVAVLYQgVNCTEVPVAIHADQLTPTWRVYSTGSNVFQTRAGCL
IGAEHVNNSYECDIPIGAGICASYQTQTNSPRRARSVASQSIIAYTMSLG
AENSVAYSNNSIAIPTNFTISVTTEILPVSMTKTSVDCTMYICGDSTECS
NLLLQYGSFCTQLNRALTGIAVEQDKNTQEVFAQVKQIYKTPPIKDFGGF
NFSQILPDPSKPSKRSFIEDLLFNKVTLADAGFIKQYGDCLGDIAARDLI
CAQKFNGLTVLPPLLTDEMIAQYTSALLAGTITSGWTFGAGAALQIPFAM
QMAYRFNGIGVTQNVLYENQKLIANQFNSAIGKIQDSLSSTASALGKLQD
VVNQNAQALNTLVKQLSSNFGAISSVLNDILSRLDKVEAEVQIDRLITGR
LQSLQTYVTQQLIRAAEIRASANLAATKMSECVLGQSKRVDFCGKGYHLM
SFPQSAPHGVVFLHVTYVPAQEKNFTTAPAICHDGKAHFPREGVFVSNGT
HWFVTQRNFYEPQIITTDNTFVSGNCDVVIGIVNNTVYDPLQPELDSFKE
ELDKYFKNHTSPDVDLGDISGINASVVNIQKEIDRLNEVAKNLNESLIDL
QELGKYEQYIKWPWYIWLGFIAGLIAIVMVTIMLCCMTSCCSCLKGCCSC
GSCCKFDEDDSEPVLKGVKLHYT (with the mutation of D614G shown in lowercase) or a variant thereof. In some aspects, the variant can be a sequence 50%, 55%, 65%, 70%, 75%, 80%, 90%, 95%, 96%, 97%, 98%, or 99% identical to the sequence of SEQ ID NO: 11. Amino acids 1-1213 of SEQ ID NO:11 represent the soluble portion of the protein. Thus, amino acids 1214-1273 (shown here in underline) represent the transmembrane and cytoplasmic tail of SEQ ID NO:11.

In some aspects, the SARS-COV-2 S protein is the soluble portion of the B.1.1.7 variant S protein. In some aspects, the B.1.1.7 variant S protein comprises deletions at amino acids 69, 70, and 144 and the following substitutions: N501Y, A570D, D614G, P681H, T716I, S982A, D1118H (numbers are based on position prior to the deletion of amino acids 69, 70, and 144). Specifically, the S protein of the B.1.1.7 variant can comprise the sequence (SEQ ID NO: 12)

MFVFLVLLPLVSSQCVNLTTRTQLPPAYTNSFTRGVYYPDKVFRSSVLHS
TQDLFLPFFSNVTVVFHAISGTNGTKRFDNPVLPFNDGVYFASTEKSNII
RGWIFGTTLDSKTQSLLIVNNATNVVIKVCEFQFCNDPFLGVYHKNNKSW
MESEFRVYSSANNCTFEYVSQPFLMDLEGKQGNFKNLREFVFKNIDGYFK
IYSKHTPINLVRDLPQGFSALEPLVDLPIGINITRFQTLLALHRSYLTPG
DSSSGWTAGAAAYYVGYLQPRTFLLKYNENGTITDAVDCALDPLSETKCT
LKSFTVEKGIYQTSNFRVQPTESIVRFPNITNLCPFGEVFNATRFASVYA
WNRKRISNCVADYSVLYNSASFSTFKCYGVSPTKLNDLCFTNVYADSFVI
RGDEVRQIAPGQTGKIADYNYKLPDDFTGCVIAWNSNNLDSKVGGNYNYL
YRLFRKSNLKPFERDISTEIYQAGSTPCNGVEGFNCYFPLQSYGFQPTyG
VGYQPYRVVVLSFELLHAPATVCGPKKSTNLVKNKCVNFNFNGLTGTGVL
TESNKKFLPFQQFGRDIdDTTDAVRDPQTLEILDITPCSFGGVSVITPGT
NTSNQVAVLYQgVNCTEVPVAIHADQLTPTWRVYSTGSNVFQTRAGCLIG
AEHVNNSYECDIPIGAGICASYQTQTNShRRARSVASQSIIAYTMSLGAE
NSVAYSNNSIAIPINFTISVTTEILPVSMTKTSVDCTMYICGDSTECSNL
LLQYGSFCTQLNRALTGIAVEQDKNTQEVFAQVKQIYKTPPIKDFGGFNF
SQILPDPSKPSKRSFIEDLLFNKVTLADAGFIKQYGDCLGDIAARDLICA
QKFNGLTVLPPLLTDEMIAQYTSALLAGTITSGWTFGAGAALQIPFAMQM
AYRFNGIGVTQNVLYENQKLIANQFNSAIGKIQDSLSSTASALGKLQDVV
NQNAQALNTLVKQLSSNFGAISSVLNDILARLDKVEAEVQIDRLITGRLQ
SLQTYVTQQLIRAAEIRASANLAATKMSECVLGQSKRVDFCGKGYHLMSF
PQSAPHGVVFLHVTYVPAQEKNFTTAPAICHDGKAHFPREGVFVSNGTHW
FVTQRNFYEPQIITTHNTFVSGNCDVVIGIVNNTVYDPLQPELDSFKEEL
DKYFKNHTSPDVDLGDISGINASVVNIQKEIDRLNEVAKNLNESLIDLQE
LGKYEQYIKWPWYIWLGFIAGLIAIVMVTIMLCCMTSCCSCLKGCCSCGS
CCKFDEDDSEPVLKGVKLHYT (substitutions shown in lowercase) or a variant thereof. In some aspects, the variant can be a sequence 50%, 55%, 65%, 70%, 75%, 80%, 90%, 95%, 96%, 97%, 98%, or 99% identical to the sequence of SEQ ID NO: 12. Amino acids 1-1210 of SEQ ID NO: 12 represent the soluble portion of the protein. Thus, amino acids 1211-1270 (shown here in underline) represent the transmembrane and cytoplasmic tail of SEQ ID NO: 12.

In some aspects, the SARS-COV-2 S protein is the soluble portion of the B.1.351 variant S protein. In some aspects, the B.1.351 variant S protein comprises the following substitutions D80A, D215G, K417N, A701V, N501Y, E484K. Specifically, the S protein of the B.1.351 variant can comprise the sequence (SEQ ID NO: 13)

MFVFLVLLPLVSSQCVNLTTRTQLPPAYTNSFTRGVYYPDKVFRSSVLHS
TQDLFLPFFSNVTWFHAIHVSGTNGTKRFaNPVLPFNDGVYFASTEKSNI

-continued

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRgLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGoIADYNYKLPDDFTGCVIAWNSNNLDSKVGGNYN

YLYRLFRKSNLKPFERDISTEIYQAGSTPCNGVkGFNCYFPLQSYGFQPT yGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQdVNCTEVPVAIHADQLTPTWRVYSTGSNVFQTRAGCL

IGAEHVNNSYECDIPIGAGICASYQTQTNSPRRARSVASQSIIAYTMSLG vENSVAYSNNSIAIPTNFTISVTTEILPVSMTKTSVDCTMVICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGT

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYT (substitutions shown in lowercase) or a variant thereof. In some aspects, the variant can be a sequence 50%, 55%, 65%, 70%, 75%, 80%, 90%, 95%, 96%, 97%, 98%, or 99% identical to the sequence of SEQ ID NO:13. Amino acids 1-1213 of SEQ ID NO: 13 represent the soluble portion of the protein. Thus, amino acids 1214-1273 (shown here in underline) represent the transmembrane and cytoplasmic tail of SEQ ID NO:13.

In some aspects, the SARS-COV-2 S protein is the soluble portion of the P.1 variant S protein. In some aspects, the P.1 variant S protein comprises the following substitutions L18F, T20N, P26S, D138Y, R190S, K417T, E484K, N501Y, H655Y, T1027I. Specifically, the S protein of the P.1 variant can comprise the sequence (SEQ ID NO: 14)

MFVFLVLLPLVSSQCVNfTnRTQLPsAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNyPFLGVYYHKNNK

SWMESEFRVYSSANNCTFEYVSQPFLMDLEGKQGNFKNLsEFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

-continued

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGtIADYNYKLPDDFTGCVIAWNSNNLDSKVGGNYN

YLYRLFRKSNLKPFERDISTEIYQAGSTPCNGVkGFNCYFPLQSYGFQPT yGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQdVNCTEVPVAIHADQLTPTWRVYSTGSNVFQTRAGCL

IGAEyVNNSYECDIPIGAGICASYQTQTNSPRRARSVASQSIIAYTMSLG

AENSVAYSNNSIAIPTNFTISVTTEILPVSMTKTSVDCTMYICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAAEIRASANLAAlKMSECVLGQSKRVDFCGKGYHLM

SFPQSAPHGVVFLHVTYVPAQEKNFTTAPAICHDGKAHFPREGVFVSNGT

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYT (substitutions shown in lowercase) or a variant thereof. In some aspects, the variant can be a sequence 50%, 55%, 65%, 70%, 75%, 80%, 90%, 95%, 96%, 97%, 98%, or 99% identical to the sequence of SEQ ID NO:14. Amino acids 1-1213 of SEQ ID NO: 14 represent the soluble portion of the protein. Thus, amino acids 1214-1273 (shown here in underline) represent the transmembrane and cytoplasmic tail of SEQ ID NO: 14.

In some aspects, the SARS-COV-2 S protein is the soluble portion of the 20C/S: 452R variant S protein. In some aspects, the 20C/S: 452R variant S protein comprises the following substitutions S13I, W152C, L452R. Specifically, the S protein of the 20C/S: 452R variant can comprise the sequence (SEQ ID NO: 15)

MFVFLVLLPLVSlQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

ScMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YrYRLFRKSNLKPFERDISTEIYQAGSTPCNGVEGFNCYFPLQSYGFQPT

-continued

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSLG

AENSVAYSNNSIAIPTNFTISVTTEILPVSMTKTSVDCTMYICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGT

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYT (substitutions shown in lowercase) or a variant thereof. In some aspects, the variant can be a sequence 50%, 55%, 65%, 70%, 75%, 80%, 90%, 95%, 96%, 97%, 98%, or 99% identical to the sequence of SEQ ID NO:15. Amino acids 1-1213 of SEQ ID NO: 15 represent the soluble portion of the protein. Thus, amino acids 1214-1273 (shown here in underline) represent the transmembrane and cytoplasmic tail of SEQ ID NO: 15.

In some aspects, the SARS-COV-2 S protein is the soluble portion of the cluster 5 variant S protein. In some aspects, the cluster 5 variant S protein comprises deletions at amino acids 69, 70 and the following substitutions U453F, 1692V, and M1229I. Specifically, the S protein of the cluster 5 variant can comprise the sequence (SEQ ID NO: 16)

MFVFLVLLPLVSSQCVNLTTRTQLPPAYTNSFTRGVYYPDKVFRSSVLHS

TQDLFLPFFSNVTWFHAISGTNGTKRFDNPVLPFNDGVYFASTEKSNIIR

GWIFGTTLDSKTQSLLIVNNATNVVIKVCEFQFCNDPFLGVYYHKNNKSW

MESEFRVYSSANNCTFEYVSQPFLMDLEGKQGNFKNLREFVFKNIDGYFK

IYSKHTPINLVRDLPQGFSALEPLVDLPIGINITRFQTLLALHRSYLTPG

DSSSGWTAGAAAYYVGYLQPRTFLLKYNENGTITDAVDCALDPLSETKCT

LKSFTVEKGIYQTSNFRVQPTESIVRFPNITNLCPFGEVFNATRFASVYA

WNRKRISNCVADYSVLYNSASFSTFKCYGVSPTKLNDLCFTNVYADSFVI

RGDEVRQIAPGQTGKIADYNYKLPDDFTGCVIAWNSNNLDSKVGGNYNYL fRLFRKSNLKPFERDISTEIYQAGSTPCNGVEGFNCYFPLQSYGFQPTNG

VGYQPYRVVVLSFELLHAPATVCGPKKSTNLVKNKCVNFNFNGLTGTGVL

TESNKKFLPFQQFGRDIADTTDAVRDPQTLEILDITPCSFGGVSVITPGT

NTSNQVAVLYQDVNCTEVPVAIHADQLTPTWRVYSTGSNVFQTRAGCLIG

AEHVNNSYECDIPIGAGICASYQTQTNSPRRARSVASQSIvAYTMSLGAE

-continued

NSVAYSNNSIAIPTNFTISVTTEILPVSMTKTSVDCTMYICGDSTECSNL

LLQYGSFCTQLNRALTGIAVEQDKNTQEVFAQVKQIYKTPPIKDFGGFNF

SQILPDPSKPSKRSFIEDLLFNKVTLADAGFIKQYGDCLGDIAARDLICA

QKFNGLTVLPPLLTDEMIAQYTSALLAGTITSGWTFGAGAALQIPFAMQM

AYRFNGIGVTQNVLYENQKLIANQFNSAIGKIQDSLSSTASALGKLQDVV

NQNAQALNTLVKQLSSNFGAISSVLNDILSRLDKVEAEVQIDRLITGRLQ

SLQTYVTQQLIRAAEIRASANLAATKMSECVLGQSKRVDFCGKGYHLMSF

PQSAPHGVVFLHVTYVPAQEKNFTTAPAICHDGKAHFPREGVFVSNGTHW

FVTQRNFYEPQIITTDNTFVSGNCDVVIGIVNNTVYDPLQPELDSFKEEL

DKYFKNHTSPDVDLGDISGINASVVNIQKEIDRLNEVAKNLNESLIDLQE

LGKYEQYIKWPWYIWLGFIAGLIAIVMVTIMLCCMTSCCSCLKGCCSCGS

CCKFDEDDSEPVLKGVKLHYT (substitutions shown in lowercase) or a variant thereof. In some aspects, the variant can be a sequence 50%, 55%, 65%, 70%, 75%, 80%, 90%, 95%, 96%, 97%, 98%, or 99% identical to the sequence of SEQ ID NO:16. Amino acids 1-1210 of SEQ ID NO: 16 represent the soluble portion of the protein. Thus, amino acids 1214-1270 (shown here in underline) represent the transmembrane and cytoplasmic tail of SEQ ID NO: 16.

In some aspects, the SARS-COV-2 S protein can be cleaved into S1 and S2 subunits by proteases. In some aspects, S1 comprises the receptor-binding domain (RBD) which allows viruses to directly bind to the ACE2 receptor. In some aspects, S2 can mediate membrane fusion, with the help of a protease, in cells. In some aspects, the SARS-COV-2 S protein ("S protein") is the full length soluble S protein, the S1 subunit, the S2 subunit, or the RBD. In some aspects, the SARS-COV-2 S protein is a portion of full length soluble S protein, the S1 subunit, the S2 subunit, or the RBD. In some aspects, the SARS-COV-2 S protein is a variant of a wild type sequence and thus, is 50, 55, 60, 65, 70, 75, 80, 85, 90, 95, 96, 97, 98, 99, or 100% identical to the wild type full length S protein, the S1 subunit, the S2 subunit, or the RBD. In some aspects, a variant SARS-COV-2 S protein can comprise a modified amino acid or a non-naturally occurring amino acid.

In some aspects, the complete wild type amino acid sequence of SARS-COV-2 can be found in Genbank as accession number MN908947. The S protein is nucleic acids 21563-25384 of accession number MN908947.

In some aspects, the S protein is the full length S protein. Because the S protein can be cleaved by proteases, in some aspects, the disclosed SARS-COV-2 S protein can be altered or mutated to remove the cleavage sites and produce a non-cleavable S protein. In some aspects, the mutations that remove the cleavage site are R685A and R816A of the full length wild type S protein. For example, the cleavage sites of R685A and R816A are at positions 685 and 816, respectively, of SEQ ID NO:8.

In some aspects, the S protein can be further altered or mutated so that the S protein retains its prefusion state. In some aspects, mutations that maintain the S protein in a prefusion state can be K986P and V987P.

iv. Linkers

Disclosed are peptides comprising a monomeric Fc fragment of an immunoglobulin recognized by FcRn; a SARS- COV-2 antigen; and a trimerization domain, wherein the peptide further comprises one or more linkers.

In some instances, at least one of the one or more linkers is on the N-terminus end of the monomeric Fc fragment of an immunoglobulin recognized by a FcRn. In some instances, at least one of the one or more linkers is on the C-terminus end of the monomeric Fc fragment of an immunoglobulin recognized by a FcRn.

In some instances, at least one of the one or more linkers is located between the SARS-COV-2 antigen and the monomeric Fc fragment of an immunoglobulin recognized by a FcRn. In some instances, at least one of the one or more linkers is located between the trimerization domain and the monomeric Fc fragment of an immunoglobulin recognized by a FcRn. In some instances, at least one of the one or more linkers is located between the trimerization domain and the SARS-COV-2 antigen.

In some instances, the one or more linkers are small, nonpolar, amino acid linkers. For example, the linker can be a GS-linker. The number of glycine, serine, and glycine/serine repeats can vary in the one or more linkers. Examples of GS linkers can be GSGSGS (SEQ ID NO: 23) and GSGGGGGGGGSGS (SEQ ID NO:24).

v. Additional Elements

In some aspects, the disclosed peptides comprise a signal peptide. In some aspects, a signal peptide is any short peptide (about 10-30 amino acids) that help translocate the peptide to the cell membrane. In some aspects, the signal peptide is present on the N-terminal end of the SARS-COV-2 antigen. In some aspects, the signal peptide is derived from the coronavirus antigen. In some aspects, the signal peptide is derived from the SARS-COV-2 antigen. For example, the native signal peptide found on SARS-COV-2 S protein can be present in the disclosed peptides. In some aspects, the native signal peptide can comprise the amino acid sequence of MFVFLVLLPLVSSQC (SEQ ID NO:25) from SARS-COV-2 S protein. In some aspects, a signal peptide can comprise one or more of the sequences present in Table 1.

TABLE 1

Exemplary signal peptide sequences.

| Signal Sequence Name | Sequence | SEQ ID NO: |
|---|---|---|
| Human OSM | MGVLLTQRTLLSLVLALLFPSMASM | 19 |
| VSV-G | MKCLLYLAFLFIGVNC | 20 |
| Mouse Ig Kappa | METDTLLLWVLLLWVPGSTGD | 21 |
| Human IgG2 H | MGWSCIILFLVATATGVHS | 22 |
| BM40 | MRAWIFFLLCLAGRALA | 23 |
| Secrecon | MWWRLWWLLLLLLLLWPMVWA | 24 |
| Human IgKVIII | MDMRVPAQLLGLLLLWLRGARC | 25 |
| CD33 | MPLLLLLPLLWAGALA | 26 |
| tPA | MDAMKRGLCCVLLLCGAVFVSPS | 27 |
| Human Chymotrypsinogen | MAFLWLLSCWALLGTTFG | 28 |
| Human trypsinogen-2 | MNLLLILTFVAAAVA | 29 |

TABLE 1-continued

Exemplary signal peptide sequences.

| Signal Sequence Name | Sequence | SEQ ID NO: |
|---|---|---|
| Human IL-2 | MYRMQLLSCIALSLALVTNS | 30 |
| Gaussia luc | MGVKVLFALICIAVAEA | 31 |
| Albumin(HSA) | MKWVTFISLLFSSAYS | 32 |
| Influenza Haemagglutinin | MKTIIALSYIFCLVLG | 33 |
| Human insulin | MALWMRLLPLLALLALWGPDPAAA | 34 |
| Silkworm Fibroin LC | MKPIFLVLLVVTSAYA | 35 |
| Human CD5 | MPMGSLQPLATLYLLGMLVASCLG | 36 |

In some instances, the disclosed peptides can further comprise cleavage sites or tag sequences.

In some instances, a cleavage site can be present in the disclosed peptides. Cleavage sites can allow for cleavage of the monomeric Fc fragment of an immunoglobulin recognized by FcRn away from the SARS-COV-2 antigen. In some instances, a cleavage site can be recognized by a protease or a chemical compound. In some instances, a cleavage site can be a site recognized by, but not limited to, enterokinase, pepsin, factor Xa, tobacco etch virus protease, or thrombin.

In some instances, a tag sequence can be present in the disclosed peptides. In some instances, a tag sequence can be a detection label/label sequence or a purification tag. As used herein, a detection label or label sequence is any molecule that can be associated with a nucleic acid or peptide, directly or indirectly, and which results in a measurable, detectable signal, either directly or indirectly. Many such labels for incorporation into nucleic acids or coupling to nucleic acids or peptides are known to those of skill in the art. Examples of detection labels can be, but are not limited to, radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, OR and Research Organics, Cleveland, Ohio.

In some instances, a label sequence can be, but is not limited to, an isotope marker, colorimetric biosensors, or fluorescent labels. For example, fluorescent markers can be, but are not limited to, green fluorescent protein (GFP) or rhodamine fluorescent protein (RFP). Other label sequences can include biotin, streptavidin, horseradish peroxidase, or luciferase.

In some instances, a tag sequence can be a purification tag. In some instances, a purification tag can be, but is not limited to, histidine, glutathione-S-transferase, albumin-binding protein, FLAG epitope, galactose-binding protein, myc, or hemagglutinin.

In some aspects, the compositions or peptides disclosed herein can further comprise an adjuvant. In some aspects, the adjuvant is immunostimulatory oligonucleotides containing unmethylated CpG dinucleotides ("CpG"). CpGs are known in the art as being adjuvants when administered by both systemic and mucosal routes (WO 96/02555, EP 468520, Davis et al., J. Immunol, 1998, 160 (2): 870-876, McCluskie and Davis, J. Immunol., 1998, 161 (9): 4463-6). CpG is an abbreviation for cytosineguanosinc dinucicotide motifs present in DNA. Historically, it was observed that the DNA fraction of BCG could exert an anti-tumour effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated in a publication by Krieg, 1995, Nature 374, p. 546. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in the present invention.

vi. Example Peptides

Disclosed are peptides comprising a monomeric Fc fragment of an immunoglobulin recognized by a FcRn; a SARS-COV-2 soluble S protein; and a trimerization domain. For example, disclosed are peptides comprising the amino acid sequence of (SEQ ID NO: 1)

MFVFLVLLPLVSSQCVNLTTRTQLPPAYTNSFTRGVYYPDKVFRSSVLHSTQDLFLPFFS

NVTWFHAIHVSGTNGTKRFDNPVLPFNDGVYFASTEKSNIIRGWIFGTTLDSKTQSLLIV

NNATNVVIKVCEFQFCNDPFLGVYYHKNNKSWMESEFRVYSSANNCTFEYVSQPFLMD

LEGKQGNFKNLREFVFKNIDGYFKIYSKHTPINLVRDLPQGFSALEPLVDLPIGINITRFQ

TLLALHRSYLTPGDSSSGWTAGAAAYYVGYLQPRTFLLKYNENGTITDAVDCALDPLS

ETKCTLKSFTVEKGIYQTSNFRVQPTESIVRFPNITNLCPFGEVFNATRFASVYAWNRKRISNCVADYSVLYNSASFS

TFKCYGVSPTKLNDLCFTNVYADSFVIRGDEVRQIAPGQTGKIADYNYKLPDDFTGCVIAWNSNNLDSKVGGNYNYLYRLFRKS

NLKPFERDISTEIYQAGSTPCNGVEGFNCYFPLQSYGFQPTNGVGYQPYRVVVLSFELLHAPATVCGPKKSTNLVKNKCVNFN

FNGLTGTGVLTESNKKFLPFQQFGRDIADTTDAVRDPQTLEILDITPCSFGGVSVITPGTN

TSNQVAVLYQDVNCTEVPVAIHADQLTPTWRVYSTGSNVFQTRAGCLIGAEHVNNSYE

CDIPIGAGICASYQTQTNSPRRAASVASQSIIAYTMSLGAENSVAYSNNSIAIPTNFTISVT

TEILPVSMTKTSVDCTMYICGDSTECSNLLLQYGSFCTQLNRALTGIAVEQDKNTQEVF

AQVKQIYKTPPIKDFGGFNFSQILPDPSKPSKASFIEDLLFNKVTLADAGFIKQYGDCLGD

IAARDLICAQKFNGLTVLPPLLTDEMIAQYTSALLAGTITSGWTFGAGAALQIPFAMQM

AYRFNGIGVTQNVLYENQKLIANQFNSAIGKIQDSLSSTASALGKLQDVVNQNAQALNT

LVKQLSSNFGAISSVLNDILSRLDppEAEVQIDRLITGRLQSLQTYVTQQLIRAAEIRASAN

LAATKMSECVLGQSKRVDFCGKGYHLMSFPQSAPHGVVFLHVTYVPAQEKNFTTAPAI

CHDGKAHFPREGVFVSNGTHWFVTQRNFYEPQIITTDNTFVSGNCDVVIGIVNNTVYDP

LQPELDSFKEELDKYFKNHTSPDVDLGDISGINASVVNIQKEIDRLNEVAKNLNESLIDL

QELGKYEQYIKWPGSGSGSRSLVPRGSPgsgyipeaprdgoayvrkdgewvllstflgGSGGGGSGGG

GSGSEPKSCDKTHTsPPsPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCaV

SNKALPAPIEKTISKAKGQPREPQVYTLPPSRDELTKNQVSLTCLVKGFYPSDIAVE

-continued

WESNGQPENNYKTTPPVLDSDGSFFLYSKLTVDKSRWQQGNVFSCSVMHEALHNH

YTQKSLSLSPGK or a variant thereof. In some aspects, the variant can a sequence 50%, 55%, 65%, 70%, 75%, 80%, 90%, 95%, 96%, 97%, 98%, or 99% identical to the sequence of SEQ ID NO:1. The underlined sequence represents a native signal peptide of S protein. The bold subscript sequence represents the RBD of S1. The bold underline sequence represents the mutated S1/S2 cleavage site (R685A of S protein in italics, no change in S686 of S protein). The bold letter and bold underline sequence represents a mutation at the S2' cleavage site (R816A of S protein in italics, no change in S817 of S protein). The bold, italics, and subscript sequence represents K986P and V987P mutations (of the S protein) which allow the S protein to keep the Pre-fusion conformation. The dotted underline sequence represents a 6GS (glycine-serine) linker. The bold lowercase letters represents the foldon domain from T4 fibrin. The dotted underline, italicized sequence represents a 14GS (glycine-serine) linker. The bold sequence is human IgG1. The dotted underline lowercase sequence S represents a cysteine to serine mutation (C226S of human IgG1, Ser at position 1283 of SEQ ID NO:1) in human IgG1 to produce a monomer human IgG1. The dotted underline lowercase sequence S represents a cysteine to serine mutation (C229S of human IgG1, Ser at position 1286 of SEQ ID NO:1) in human IgG1 to produce a monomer human IgG1. The italicized, underlined lowercase sequence represents a mutation preventing complement binding (K322A of human IgG1, Ala at position 1379 of SEQ ID NO:1) in human IgG1. Amino acids 16 to 1213 represent the SARS-Cov-2 spike protein. Amino acids 1229 to 1257 represent the foldon domain of T4 fibrin. Amino acids 1273 to 1504 represent a monomeric Fc IgG1 fragment.

Disclosed are peptides comprising a monomeric Fc fragment of an immunoglobulin recognized by a FcRn; a SARS-COV-2 S1 protein; and a trimerization domain. For example, disclosed are peptides comprising the amino acid sequence of (SEQ ID NO: 3)

MFVFLVLLPLVSSQCVNLTTRTQLPPAYTNSFTRGVYYPDKVFRSSVLHSTQDLFLPFFS

NVTWFHAIHVSGTNGTKRFDNPVLPFNDGVYFASTEKSNIIRGWIFGTTLDSKTQSLLIV

NNATNVVIKVCEFQFCNDPFLGVYYHKNNKSWMESEFRVYSSANNCTFEYVSQPFLMD

LEGKQGNFKNLREFVFKNIDGYFKIYSKHTPINLVRDLPQGFSALEPLVDLPIGINITRFQ

TLLALHRSYLTPGDSSSGWTAGAAAYYVGYLQPRTFLLKYNENGTITDAVDCALDPLS

ETKCTLKSFTVEKGIYQTSNF*RVQPTESIVRFPNITNLCPFGEVFNATRFASVYAWNRKRISNCVADYSVLYNSASFS*

*TFKCYGVSPTKLNDLCFTNVYADSFMRGDEVRQIAPGQTGKIADYNYKLPDDFTGCVIAWNSNNLDSKVGGNYNYLYRLFRKS*

*NLKPFERDISTEIYQAGSTPCNGVEGFNCYFPLQSYGFQPTNGVGYQPYRVVVLSFELLHAPATVCGPKKSTNLVKNKCVNF*N

FNGLTGTGVLTESNKKFLPFQQFGRDIADTTDAVRDPQTLEILDITPCSFGGVSVITPGTN

TSNQVAVLYQDVNCTEVPVAIHADQLTPTWRVYSTGSNVFQTRAGCLIGAEHVNNSYE

CDIPIGAGICASYQTQTNSPRR*A*GSGSGSRSLVPRGSPgsgyipeaprdgoayvrkdgewvllstflg

*GSGGGGSGGGGSGS*EPKSCDKTHTsPPsPAPELLGGPSVFLFPPKPKDTLMISRTPEVTCV

VVDVSHEDPEVKFNWYVDGVEVHNAKTKPREEQYNSTYRVVSVLTVLHQDWLNGKE

YKC*a*VSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEALHNH

YTQKSLSLSPGK or a variant thereof. In some aspects, the variant can a sequence 50%, 55%, 65%, 70%, 75%, 80%, 90%, 95%, 96%, 97%, 98%, or 99% identical to the sequence of SEQ ID NO:3. The underlined sequence represents a native signal peptide of S protein. The bold subscript sequence represents the RBD of S1. The bold underline sequence represents the mutated S1/S2 cleavage site (R685A in italics). The dotted underline sequence represents a 6GS (glycine-serine) linker. The bold lowercase represents the foldon domain from T4 fibrin. The dotted underline, italicized sequence represents a 14GS (glycine-serine) linker. The bold sequence is human IgG1. The dotted underline lowercase sequence S represents a cysteine to serine mutation (C226S of human IgG1, Ser at position 755 of SEQ ID NO:3) in human IgG1 to produce a monomer human IgG1. The dotted underline lowercase sequence S represents a cysteine to serine mutation (C229S of human IgG1, Ser at position 758 of SEQ ID NO: 3) in human IgG1 to produce a monomer human IgG1. The italicized, underlined lowercase sequence represents a mutation preventing complement binding (K322A of human IgG1, Ala at position 851 of SEQ ID NO:3) in human IgG1. Amino acids 16 to 685 represent the SARS-Cov-2 S1 protein. Amino acids 701 to 729 represent the foldon domain of T4 fibrin. Amino acids 745 to 976 represent a monomeric Fc IgG1 fragment.

Disclosed are peptides comprising a monomeric Fc fragment of an immunoglobulin recognized by a FcRn; a SARS-COV-2 RBD protein; and a trimerization domain. For example, disclosed are peptides comprising the amino acid sequence of (SEQ ID NO: 5)

MFVFLVLLPLVSSQCVRVQPTESIVRFPNITNLCPFGEVFNATRFASVYAWNRKRISNCVADYSVLYNSASFSTFKCYG

VSPTKLNDLCFTNYTADSFVIRGDEVRQIAPGQTGKIADYNYKLPDDFTGCVIAWNSNNLDSKVGGNYNYLYRLFRKSNLKPFE

RDISTEIYQAGSTPCNGVEGFNCYFPLQSYGFQPTNGVGYQPYRVWLSFELLHAPATVCGPKKSTNLVKNKCVNFGSGSGS

RSLVPRGSPgsgyipeaprdgoayvrkdgewvllstflgGSGGGGSGGGGSGSEPKSCDKTHTsPPsP

APELLGGPSVFLFPPKPKDTLMISRTPEVTCVVVDVSHEDPEVKFNWYVDGVEVHN

AKTKPREEQYNSTYRVVSVLTVLHQDWLNGKEYKCaVSNKALPAPIEKTISKAKG

QPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK or a variant thereof. In some aspects, the variant can a sequence 50%, 55%, 65%, 70%, 75%, 80%, 90%, 95%, 96%, 97%, 98%, or 99% identical to the sequence of SEQ ID NO:5. The underlined sequence represents a native signal peptide of S protein. The bold subscript sequence represents the RBD of S1. The dotted underline sequence represents a 6GS (glycine-serine) linker. The bold lowercase represents the foldon domain from T4 fibrin. The dotted underline, italicized sequence represents a 14GS (glycine-serine) linker. The bold sequence is human IgG1. The dotted underline lowercase sequence S represents a cysteine to serine mutation (C226S of human IgG1, Ser at position 309 of SEQ ID NO:5) in human IgG1 to produce a monomer human IgG1. The dotted underline lowercase sequence S represents a cysteine to serine mutation (C229S of human IgG1, Ser at position 312 of SEQ ID NO:5) in human IgG1 to produce a monomer human IgG1. The italicized, underlined lowercase sequence represents a mutation preventing complement binding (K322A of human IgG1, Ala at position 405 of SEQ ID NO: 5) in human IgG1. Amino acids 17 to 239 represent the SARS-Cov-2 RBD protein. Amino acids 255 to 283 represent the foldon domain of T4 fibrin. Amino acids 299 to 530 represent a monomeric Fc IgG1 fragment.

2. Peptides without a Trimerization Domain

Disclosed are peptides comprising a Fc fragment of an immunoglobulin recognized by a FcRn and a coronavirus antigen. In some aspects, the coronavirus antigen can be any coronavirus spike protein, or antigenic fragment thereof. In some aspects, the coronavirus is Middle East respiratory syndrome coronavirus (MERS-COV), Human Coronavirus-Erasmus Medical Centre (HCoV-EMC), SARS-COV, or SARS-COV-2. Thus, in some aspects, the coronavirus spike protein can be a MERS-COV, HCoV-EMC, SARS-COV, or SARS-COV-2 spike protein, or antigenic fragment thereof. In some aspects, the peptides do not comprise a trimerization domain.

Disclosed are peptides comprising a Fc fragment of an immunoglobulin recognized by a FcRn and a SARS-COV-2 antigen. In some aspects, the SARS-COV-2 antigen can be a SARS-COV-2 spike protein. Thus, disclosed are peptides comprising a Fc fragment of an immunoglobulin recognized by a FcRn and a SARS-COV-2 spike protein. In some aspects, the peptides do not comprise a trimerization domain.

Disclosed are peptides comprising a Fc fragment of an immunoglobulin recognized by a FcRn and a SARS-COV-2 RBD protein. Thus, disclosed are peptides comprising a Fc fragment of an immunoglobulin recognized by a FcRn and a SARS-COV-2 RBD protein.

In some instances, the Fc fragment of an immunoglobulin recognized by a FcRn is conjugated to the amino or carboxy terminal end of a coronavirus antigen. The conjugation can be direct or indirect. Indirect conjugation can be due to the presence of a linker, for example, a linker can be present in between the coronavirus antigen and the Fc fragment of an immunoglobulin recognized by a FcRn. In some aspects, the peptides do not comprise a trimerization domain.

Disclosed are peptides encoded by one or more of the nucleic acid sequences provided herein.

i. Fc Fragment

A Fc fragment of an immunoglobulin recognized by a FcRn, as disclosed herein, can be any Fc fragment that can be recognized by a FcRn and is capable of forming a dimeric structure. In some aspects, a Fc fragment of an immunoglobulin recognized by a FcRn can comprise only the Fc portion of an immunoglobulin.

In some aspects, unlike the monomeric Fc fragment of an immunoglobulin recognized by a FcRn, the Fc fragment of an immunoglobulin recognized by a FcRn capable of forming a dimeric structure retains the cysteine residues responsible for dimer formation in native IgG.

For example, positions 226 and 229 of the full length sequence of the wild type sequence of human IgG1 are not mutated and thus retain the ability for dimer formation. In some aspects, positions 11 and 14 of a sequence comprising only the hinge region, CH2 and CH3 domains of wild type IgG are not mutated. For example, the cysteine residues at positions 11 and 14 of SEQ ID NO:17 are not mutated. In some aspects, positions 11 and 14 of SEQ ID NO: 7 are located in the hinge region of Fc fragments of an immunoglobulin recognized by a FcRn that retain the ability to form dimers.

In some aspects, the C1q binding site can be ablated in the Fc fragment that retains the ability for dimer formation. This can be effective to help avoid clearance of the Fc fragments via the complement pathway and thus allowing the disclosed peptides comprising a Fc fragment and coronavirus antigen to remain in a subject and provide its therapeutic effect. In some aspects, C1q is known to bind to the CH2 domain of an immunoglobulin, particularly IgG. In some aspects, substituting the lysine at position 322 of wild type human IgG can ablate or eliminate the complement C1q binding site. For example, replacing Lys322 of full length human IgG with an Ala residue can ablate or eliminate the complement C1q binding site. In some aspects, replacing one or more of Glu318, Lys320, and Lys322 of full length mouse IgG with an Ala residue can ablate or eliminate the complement C1q binding site. In some aspects, ablating C1q binding to the disclosed monomeric Fc fragments comprises mutation position 107 of a Fc fragment of an immunoglobulin recognized by a FcRn that retains the ability for dimer formation. For example, a mutation of lysine to alanine shown at position 107 of SEQ ID NO: 17 can ablate C1q binding to a human Fc fragment of an immunoglobulin recognized by a FcRn.

In some aspects, the FcRn binding sites are known to be His310 and His433 or His310/Gln311 (HQ) and His433/Asn434 (HN) of full length wild type IgG. The region of the Fc-fragment of IgG that binds to the FcRn receptor in humans has been described based upon X-ray crystallography (Burmaister, W. P. et al., Nature, 1994; 372:379-378; incorporated by reference in its entirety herein). The major contact area of Fc with the FcRn receptor is near the junction of the CH2 and CH3 domains. Potential contacts are residues 248, 250-257, 272, 285, 288, 290-291, 308-311 and 314 in CH2 and 385-387, 428 and 433-436 in CH3 of wild type IgG. In some aspects, no mutations would be present in the FcRn binding sites. Given the foregoing information, those of ordinary skill in the art will readily recognize that the monomeric Fc fragment of IgG can be modified according to well-recognized procedures such as site-directed mutagenesis and the like to yield modified monomeric Fc fragments or portions thereof that will be bound by the FcRn receptor. Such modifications include modifications remote from the FcRn contact sites as well as modifications within the contact sites that preserve or even enhance binding.

In some aspects, the Fc fragment of an immunoglobulin recognized by a FcRn that retains the ability for dimer formation can be derived from any isotype that binds FcRn. The Fc-fragment should be chosen from an immunoglobulin known to bind the FcRn in the mucosa of the subject receiving the antigen-Fc vaccine. Immunoglobulin subclasses recognized by FcRn in different epithelial mucosa of animal subjects are known to a person in the art and can be found in Ober, R. J. et al, 2001, Int. Immunol. 13, 1551-9, incorporated by reference in its entirety herein. In some aspects, the Fc fragment of an immunoglobulin recognized by a FcRn is derived from a mammalian immunoglobulin. For example, the Fc fragment of an immunoglobulin recognized by a FcRn can be a human immunoglobulin sequence.

In some aspects, the amino acid sequence of a Fc fragment of a human IgG1 that retains the ability for dimer formation can be (SEQ ID NO: 17)

```
EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW
```

-continued

```
LNGKEYKCaVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

or a variant thereof. In some aspects, the variant can a sequence 50%, 55%, 65%, 70%, 75%, 80%, 90%, 95%, 96%, 97%, 98%, or 99% identical to the sequence of SEQ ID NO: 17. The two cysteine residues at positions 11 and 14 help retain the ability for dimer formation. A lysine to alanine mutation is shown at position 107. The lysine to alanine mutation ablates C1q binding to the Fc fragment.

In some aspects, the amino acid sequence of a Fc fragment of an immunoglobulin recognized by a FcRn that retains the ability for dimer formation of a mouse IgG2a can be (SEQ ID NO: 18)

```
EPRGPTIKPCPPCKSPAPNLLGGPSVFIFPPKIKDVLMISLSPIVTCVV

VDVSEDDPDVQISWFVNNVEVHTAQTQTHREDYNSTLRVVSALPIQHQD

WMSGKAFACAVNNKDLPAPIERTISKPKGSVRAPQVYVLPPPEEEMTKK

QVTLTCMVTDFMPEDIYVEWTNNGKTELNYKNTEPVLDSDGSYFMYSKL

RVEKKNWVERNSYSCSVVHEGLHNHHTTKSFSRTPGK
```

or a sequence 50%, 55%, 65%, 70%, 75%, 80%, 90%, 95%, 96%, 97%, 98%, or 99% identical to the sequence of (SEQ ID NO:18).

In some aspects, the Fc fragment of an immunoglobulin recognized by a FcRn that retains the ability for dimer formation comprises a full length Fc region of an immunoglobulin. In some aspects, the monomeric Fc fragment of an immunoglobulin recognized by a FcRn comprises at least the CH2 and CH3 domains of a Fc region of an immunoglobulin. For example, the monomeric Fc fragment of an immunoglobulin recognized by a FcRn comprises one or more of a full length CH2 and CH3 domain of IgG. In some aspects, the monomeric Fc fragment of an immunoglobulin recognized by a FcRn comprises at least a portion of the one or more CH2 and CH3 domains so long as the portions of the one or more CH2 and CH3 domains retains the ability to be recognized by FcRn.

In some aspects, the monomeric Fc fragment of an immunoglobulin recognized by a FcRn is conjugated to the amino or carboxy terminal end of a SARS-COV-2 antigen. For example, the SARS-COV-2 antigen can be the spike protein or a fragment thereof, such as RBD. The conjugation can be direct or indirect. Indirect conjugation can be due to the presence of a linker in between the SARS-COV-2 antigen and the Fc fragment of an immunoglobulin recognized by a FcRn. Indirect conjugation can be due to the presence of another peptide in between the SARS-COV-2 antigen and the Fc fragment of an immunoglobulin recognized by a FcRn.

In some aspects, the Fc fragment of an immunoglobulin recognized by a FcRn that retains the ability for dimerization can be derived from IgG. In some aspects, the IgG can be any IgG subtype. For example, the monomeric Fc fragment of an immunoglobulin recognized by a FcRn can be derived from IgG1, IgG2, IgG3, or IgG4.

ii. Coronavirus Antigen

In some aspects, the disclosed peptides can comprise a Fc fragment of an immunoglobulin recognized by a FcRn and a coronavirus antigen. In some aspects, a coronavirus antigen can be any region of a coronavirus that can generate an immune response. In some aspects, a coronavirus antigen can be all or a portion of the coronavirus spike(S) protein. In some aspects, the coronavirus S protein is the soluble portion of the coronavirus S protein. For example, the transmembrane domain and cytoplasmic domain are not present in the soluble portion of the coronavirus S protein. In some aspects, the coronavirus is Middle East respiratory syndrome coronavirus (MERS-COV), Human Coronavirus-Erasmus Medical Centre (HCoV-EMC), SARS-COV, or SARS-COV-2. Thus, in some aspects, the coronavirus spike protein can be a MERS-COV, HCoV-EMC, SARS-COV, or SARS-COV-2 spike protein, or antigenic fragment thereof.

In some aspects, the disclosed peptides can comprise a Fc fragment of an immunoglobulin recognized by a FcRn and a SARS-COV-2 antigen. In some aspects, a SARS-COV-2 antigen can be any region of SARS-COV-2 that can generate an immune response. In some aspects, a SARS-COV-2 antigen can be all or a portion of the SARS-COV-2 S protein. In some aspects, the SARS-COV-2 S protein is the soluble portion of the SARS-COV-2 S protein. For example, the transmembrane domain and cytoplasmic domain are not present in the soluble portion of the SARS-COV-2 S protein.

In some aspects, a SARS-COV-2 S protein can be derived from wild type SARS-CoV-2 or from a variant strain, such as, but not limited to, the variants of D614G (originally found in China/Germany), B.1.1.7 or 201/501Y.V1 (originally found in the United Kingdom), B.1.351 or 20H/501.V2 (originally found in South Africa), P.1 or 20J/501Y.V3 (originally found in Japan/Brazil), 20C/S: 452R (originally found in California), and Cluster 5 Variant (originally found in Denmark).

In some aspects, the soluble portion of the SARS-COV-2 S protein is amino acids 1-1213 of the full length wild type S protein. Specifically, the soluble portion of the SARS-COV-2 S protein comprises the sequence (SEQ ID NO: 8)

MFVFLVLLPLVSSQCVNLTTRTQLPPAYTNSFTRGVYYPDKVFRSSVLH

STQDLFLPFFSNVTWFHAIHVSGTNGTKRFDNPVLPFNDGVYFASTEKS

NIIRGWIFGTTLDSKTQSLLIVNNATNVVIKVCEFQFCNDPFLGVYYHK

NNKSWMESEFRVYSSANNCTFEYVSQPFLMDLEGKQGNFKNLREFVFKN

IDGYFKIYSKHTPINLVRDLPQGFSALEPLVDLPIGINITRFQTLLALH

RSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVEN

ATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNL

DSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDIT

PCSFGGVSVITPGTNTSNQVAVLYQDVNCTEVPVAIHADQLTPTWRVYS

TGSNVFQTRAGCLIGAEHVNNSYECDIPIGAGICASYQTQTNSPRRAAS

VASQSIIAYTMSLGAENSVAYSNNSIAIPTNFTISVTTEILPVSMTKTS

VDCTMYICGDSTECSNLLLQYGSFCTQLNRALTGIAVEQDKNTQEVFAQ

VKQIYKTPPIKDFGGFNFSQILPDPSKPSKASFIEDLLFNKVTLADAGF

-continued

IKQYGDCLGDIAARDLICAQKFNGLTVLPPLLTDEMIAQYTSALLAGTI

TSGWTFGAGAALQIPFAMQMAYRFNGIGVTQNVLYENQKLIANQFNSAI

GKIQDSLSSTASALGKLQDVVNQNAQALNTLVKQLSSNFGAISSVLNDI

LSRLDPPEAEVQIDRLITGRLQSLQTYVTQQLIRAAEIRASANLAATKM

SECVLGQSKRVDFCGKGYHLMSFPQSAPHGVVFLHVTYVPAQEKNFTTA

PAICHDGKAHFPREGVFVSNGTHWFVTQRNFYEPQIITTDNTFVSGNCD

VVIGIVNNTVYDPLQPELDSFKEELDKYFKNHTSPDVDLGDISGINASV

VNIQKEIDRLNEVAKNLNESLIDLQELGKYEQYIKWP or a variant thereof. In some aspects, the variant can be a sequence 50%, 55%, 65%, 70%, 75%, 80%, 90%, 95%, 96%, 97%, 98%, or 99% identical to the sequence of SEQ ID NO:8. The bold sequence represents the RBD of S1.

In some aspects, the SARS-COV-2 S protein is the soluble portion of the D614G variant S protein. Specifically, the S protein of the D614G variant can comprise the sequence of SEQ ID NO:11 (with the mutation of D614G shown in lowercase) or a variant thereof. In some aspects, the variant can be a sequence 50%, 55%, 65%, 70%, 75%, 80%, 90%, 95%, 96%, 97%, 98%, or 99% identical to the sequence of SEQ ID NO:11. In some aspects, the SARS-COV-2 S protein is the RBD portion of the D614G variant S protein.

In some aspects, the SARS-COV-2 S protein is the soluble portion of the B. 1.1.7 variant S protein. Specifically, the S protein of the B.1.1.7 variant can comprise the sequence of SEQ ID NO:12 or a variant thereof. In some aspects, the variant can be a sequence 50%, 55%, 65%, 70%, 75%, 80%, 90%, 95%, 96%, 97%, 98%, or 99% identical to the sequence of SEQ ID NO: 12. In some aspects, the SARS-COV-2 S protein is the RBD portion of the B.1.1.7 variant S protein.

In some aspects, the SARS-COV-2 S protein is the soluble portion of the B.1.351 variant S protein. Specifically, the S protein of the B.1.351 variant can comprise the sequence of SEQ ID NO: 13 or a variant thereof. In some aspects, the variant can be a sequence 50%, 55%, 65%, 70%, 75%, 80%, 90%, 95%, 96%, 97%, 98%, or 99% identical to the sequence of SEQ ID NO:13. In some aspects, the SARS-COV-2 S protein is the RBD portion of the B.1.351 variant S protein.

In some aspects, the SARS-COV-2 S protein is the soluble portion of the P.1 variant S protein. Specifically, the S protein of the P.1 variant can comprise the sequence of SEQ ID NO:14 or a variant thereof. In some aspects, the variant can be a sequence 50%, 55%, 65%, 70%, 75%, 80%, 90%, 95%, 96%, 97%, 98%, or 99% identical to the sequence of SEQ ID NO: 14. In some aspects, the SARS-COV-2 S protein is the RBD portion of the P.1 variant S protein.

In some aspects, the SARS-COV-2 S protein is the soluble portion of the 20C/S: 452R variant S protein. Specifically, the S protein of the 20C/S: 452R variant can comprise the sequence of SEQ ID NO:15 or a variant thereof. In some aspects, the variant can be a sequence 50%, 55%, 65%, 70%, 75%, 80%, 90%, 95%, 96%, 97%, 98%, or 99% identical to the sequence of SEQ ID NO:15. In some aspects, the SARS-COV-2 S protein is the RBD portion of the 20C/S: 452R variant S protein.

In some aspects, the SARS-COV-2 S protein is the soluble portion of the cluster 5 variant S protein. Specifically, the S protein of the cluster 5 variant can comprise the sequence of SEQ ID NO: 16 or a variant thereof. In some aspects, the variant can be a sequence 50%, 55%, 65%, 70%, 75%, 80%, 90%, 95%, 96%, 97%, 98%, or 99% identical to the sequence of SEQ ID NO:16. In some aspects, the SARS-COV-2 S protein is the RBD portion of the cluster 5 variant S protein.

In some aspects, the SARS-COV-2 S protein can be cleaved into S1 and S2 subunits by proteases. In some aspects, S1 comprises the receptor-binding domain (RBD) which allows viruses to directly bind to the ACE2 receptor. In some aspects, S2 can mediate membrane fusion, with the help of a protease, in cells. In some aspects, the SARS-COV-2 S protein ("S protein") is the full length soluble S protein, the S1 subunit, the S2 subunit, or the RBD. In some aspects, the SARS-COV-2 S protein is a portion of full length soluble S protein, the S1 subunit, the S2 subunit, or the RBD. In some aspects, the SARS-COV-2 S protein is a variant of a wild type sequence and thus, is 50, 55, 60, 65, 70, 75, 80, 85, 90, 95, 96, 97, 98, 99, or 100% identical to the wild type full length S protein, the S1 subunit, the S2 subunit, or the RBD. In some aspects, a variant SARS-COV-2 S protein can comprise a modified amino acid or a non-naturally occurring amino acid.

In some aspects, the complete wild type amino acid sequence of SARS-COV-2 can be found in Genbank as accession number MN908947. The S protein is nucleic acids 21563-25384 of accession number MN908947.

In some aspects, the S protein is the full length S protein. Because the S protein can be cleaved by proteases, in some aspects, the disclosed SARS-COV-2 S protein can be altered or mutated to remove the cleavage sites and produce a non-cleavable S protein. In some aspects, the mutations that remove the cleavage site are R685A and R816A of the full length wild type S protein. For example, the cleavage sites of R685A and R816A are at positions 685 and 816, respectively, of SEQ ID NO:8.

In some aspects, the S protein can be further altered or mutated so that the S protein retains its prefusion state. In some aspects, mutations that maintain the S protein in a prefusion state can be K986P and V987P.

iii. Linkers

Disclosed are peptides comprising a Fc fragment of an immunoglobulin recognized by FcRn that retains the ability for dimer formation and a SARS-COV-2 antigen, wherein the peptide further comprises one or more linkers.

In some instances, at least one of the one or more linkers is on the N-terminus end of the Fc fragment of an immunoglobulin recognized by a FcRn. In some instances, at least one of the one or more linkers is on the C-terminus end of the Fc fragment of an immunoglobulin recognized by a FcRn.

In some instances, at least one of the one or more linkers is located between the SARS-COV-2 antigen and the Fc fragment of an immunoglobulin recognized by a FcRn.

In some instances, the one or more linkers are small, nonpolar, amino acid linkers. For example, the linker can be a GS-linker. The number of glycine, serine, and glycine/serine repeats can vary in the one or more linkers. Examples of GS linkers can be GSGSGS (SEQ ID NO: 23) and GSGGGGSGGGGSGS (SEQ ID NO:24).

iv. Additional Elements

In some aspects, the disclosed peptides comprise a signal peptide. In some aspects, a signal peptide is any short peptide (about 10-30 amino acids) that help translocate the peptide to the cell membrane. In some aspects, the signal peptide is present on the N-terminal end of the SARS-COV-2 antigen (e.g. RBD protein). In some aspects, the signal peptide is derived from the coronavirus antigen. In some aspects, the signal peptide is derived from the SARS-COV-2 antigen. For example, the native signal peptide found on SARS-COV-2 S protein can be present in the disclosed peptides. In some aspects, the native signal peptide can comprise the amino acid sequence of MFVFLVLLPLVSSQC (SEQ ID NO:25) from SARS-COV-2 S protein. In some aspects, a signal peptide can comprise one or more of the sequences present in Table 1.

In some aspects, the peptides disclosed herein can further comprise an adjuvant. In some aspects, the adjuvant is immunostimulatory oligonucleotides containing unmethylated CpG dinucleotides ("CpG"). CpGs are known in the art as being adjuvants when administered by both systemic and mucosal routes (WO 96/02555, EP 468520, Davis et al., J. Immunol, 1998, 160 (2): 870-876, McCluskie and Davis, J. Immunol., 1998, 161 (9): 4463-6). CpG is an abbreviation for cytosineguanosinc dinucicotide motifs present in DNA. Historically, it was observed that the DNA fraction of BCG could exert an anti-tumour effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated in a publication by Krieg, 1995, Nature 374, p. 546. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in the present invention.

D. Peptide Complexes

Disclosed are peptide complexes comprising three of the disclosed peptides. For example, disclosed are peptide complexes comprising three peptides, wherein each of the three peptides comprises a monomeric Fc fragment of an immunoglobulin recognized by a FcRn; a coronavirus antigen; and a trimerization domain.

Also disclosed are peptide complexes comprising three peptides, wherein each of the three peptides comprises a monomeric Fc fragment of an immunoglobulin recognized by a FcRn; SARS-COV-2 antigen; and a trimerization domain.

In some aspects, the peptide complexes are formed when the trimerization domain of the disclosed peptides causes trimerization. Thus, the three peptides can oligomerize at the trimerization domain.

In some aspects, disclosed are peptide complexes comprising three monomeric Fc fragments of an immunoglobulin recognized by a FcRn; three SARS-COV-2 antigens; and three trimerization domains.

In some aspects, three of the disclosed peptides trimerize forming a peptide complex wherein each of the three peptides is oriented in the same direction. For example, the peptides trimerize with all of the monomeric Fc fragments of an immunoglobulin recognized by a FcRn on one end of the peptide complex and all of the SARS-COV-2 antigens on the other end of the peptide complex.

In some aspects, each peptide of the peptide complex can comprise a different coronavirus antigen. For example, in some aspects, each peptide of the peptide complex can comprise a different SARS-COV-2 spike protein fragment.

In another aspect, one or more of the peptides comprises an adjuvant instead of a coronavirus antigen. For example, two peptides of the peptide complex can comprise one of the disclosed peptides and the third peptide can be a peptide comprising a monomeric Fc fragment, a trimerization domain, and an adjuvant.

E. Nucleic Acid Sequences

As this specification discusses various peptide sequences it is understood that the nucleic acids that can encode those peptides are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the peptides. Thus, while each particular nucleic acid sequence may not be written out herein, it is understood that each and every sequence is in fact disclosed and described herein through the disclosed peptides.

Disclosed are nucleic acid sequences capable of encoding any of the peptides disclosed herein. Further disclosed are nucleic acid constructs comprising the nucleic acid sequences capable of encoding any of the peptides disclosed herein.

Disclosed are vectors comprising a nucleic acid sequence capable of encoding peptides comprising a monomeric Fc fragment of an immunoglobulin recognized by a FcRn; a SARS-COV-2 antigen; and a trimerization domain. In some instances, the peptide can be any of the peptides disclosed herein.

In some instances, the disclosed vectors can further comprise a nucleic acid sequence capable of encoding a tag (e.g. label or purification tag). In some aspects, the label can be any peptide or protein that is encoded for by a nucleic acid. For example, the labeling moiety can be, but is not limited to, GST, myc, His, or GFP.

In some instances, the labeling moiety can be operably linked to the nucleic acid sequence capable of encoding the peptides comprising a monomeric Fc fragment of an immunoglobulin recognized by a FcRn; a SARS-COV-2 antigen; and a trimerization domain. Thus, the labeling moiety and the peptide can be transcribed together.

In addition to a nucleic acid sequence capable of encoding the disclosed peptides, the disclosed vectors can carry regulatory sequences that control the expression of the disclosed peptides in a host cell. It will be appreciated by those skilled in the art that the design of the vector, including the selection of regulatory sequences can depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods of expressing polypeptides in bacterial cells or fungal cells, e.g., yeast cells, are also well known in the art.

In some instances, the disclosed vectors further comprise a promoter operably linked to the nucleic acid sequence capable of encoding the disclosed peptides. In some instances, the promoter can be an inducible promoter. In some instances, the promoter can be a cell-specific promoter. The nucleic acid sequence capable of encoding the disclosed peptides can be functionally linked to a promoter. By "functionally linked" is meant such that the promoter can promote expression of the nucleic acid sequence, thus having appropriate orientation of the promoter relative to the nucleic acid sequence.

In some instances, the nucleic acid sequence of a monomeric Fc fragment of a human IgG1 can be (SEQ ID NO: 9)

```
GAGCCTAAGTCCTGCGACAAGACCCACACAAGCCCACCATCTCCAGCTCCTGAGCT
GCTGGGAGGACCAAGCGTGTTCCTGTTTCCTCCAAAGCCTAAGGATACACTGATGA
TCTCTCGGACCCCAGAGGTGACATGCGTGGTGGTGGACGTGTCCCACGAGGACCCC
GAGGTGAAGTTTAACTGGTACGTGGACGGCGTGGAGGTGCATAATGCTAAGACCAA
GCCAAGGGAGGAGCAGTATAACAGCACATACCGGGTGGTGTCTGTGCTGACCGTGC
TGCATCAGGATTGGCTGAACGGCAAGGAATACAAGTGCGCTGTGAGCAATAAGGCC
CTGCCAGCTCCCATCGAGAAGACAATCTCTAAGGCCAAGGGCCAGCCTAGAGAGCC
ACAGGTGTATACCCTGCCACCTTCCCGCGACGAGCTGACCAAGAATCAGGTGAGCC
TGACATGTCTGGTGAAGGGCTTCTACCCTAGCGATATCGCTGTGGAGTGGGAGTCTA
ACGGCCAGCCAGAGAACAATTATAAGACCACACCACCCGTGCTGGACTCCGATGGC
AGCTTCTTTCTGTACAGCAAGCTGACAGTGGACAAGTCTCGGTGGCAGCAGGGCAA
CGTGTTCTCCTGCTCCGTGATGCATGAGGCCCTGCACAACCATTACACCCAGAAGAG
CCTGTCTCTGTCCCCTGGCAAGtga
```

or a variant thereof. In some aspects, the variant can a sequence 50%, 55%, 65%, 70%, 75%, 80%, 90%, 95%, 96%, 97%, 98%, or 99% identical to the sequence of SEQ ID NO:9. The dotted underline sequence AGC represents a cysteine to serine mutation (C226S in full length human IgG1) to produce a monomer human IgG1. The dotted underline sequence TCT represents a cysteine to serine mutation (C229S in full length human IgG1) to produce a monomer human IgG1. The italicized, underlined sequence represents a mutation preventing complement binding (K322A in full length human IgG1). The lowercase sequence represents a stop codon.

In some instances, the nucleic acid sequence of a monomeric Fc fragment of a mouse IgG2a can be (SEQ ID NO: 10)

GAGCCCAGAGGGCCCACAATCAAGCCCTCTCCTCCATCCAAATCCCCAGCACCTAA

CCTCTTGGGTGGACCATCCGTCTTCATCTTCCCTCCAAAGATCAAGGATGTACTCAT

GATCTCCCTGAGCCCCATAGTCACATGTGTGGTGGTGGATGTGAGCGAGGATGACC

CAGATGTCCAGATCAGCTGGTTTGTGAACAACGTGGAAGTACACACAGCTCAGACA

CAAACCCATAGAGAGGATTACAACAGTACTCTCCGGGTGGTCAGTGCCCTCCCCAT

CCAGCACCAGGACTGGATGAGTGGCAAGGCGTTCGCATGCGCGGTCAACAACAAA

GACCTCCCAGCGCCCATCGAGAGAACCATCTCAAAACCCAAAGGGTCAGTAAGAGC

TCCACAGGTATATGTCTTGCCTCCACCAGAAGAAGAGATGACTAAGAAACAGGTCA

CTCTGACCTGCATGGTCACAGACTTCATGCCTGAAGACATTTACGTGGAGTGGACCA

ACAACGGGAAAACAGAGCTAAACTACAAGAACACTGAACCAGTCCTGGACTCTGAT

GGTTCTTACTTCATGTACAGCAAGCTGAGAGTGGAAAAGAAGAACTGGGTGGAAAG

AAATAGCTACTCCTGTTCAGTGGTCCACGAGGGTCTGCACAATCACCACACGACTA

AGAGCTTCTCCCGGACTCCGGGTAAA or a sequence 50%, 55%, 65%, 70%, 75%, 80%, 90%, 95%, 96%, 97%, 98%, or 99% identical to the sequence of SEQ ID NO: 10. The bold underlined nucleic acids represent a mutation that encodes serine instead of cysteine to generate a single chain Fc.

In some aspects, disclosed are nucleic acid sequences comprising a monomeric Fc fragment of an immunoglobulin recognized by a FcRn sequence; a SARS-COV-2 soluble S protein sequence; and a trimerization domain sequence. For example, disclosed are nucleic acid sequences comprising the sequence of (SEQ ID NO: 2)

*GGTACC*gccaccATGTTCGTGTTTCTGGTGCTGCTGCCACTGGTGTCCAGCCAGTGCGT

GAACCTGACCACAAGAACCCAGCTGCCCCCTGCCTATACCAATTCTTTCACAAGAG

GCGTGTACTATCCAGACAAGGTGTTTCGCTCTTCCGTGCTGCACAGCACACAGGATC

TGTTTCTGCCCTTCTTTTCTAACGTGACCTGGTTCCACGCCATCCACGTGTCCGGCAC

CAATGGCACAAAGAGGTTCGACAATCCTGTGCTGCCCTTCAACGATGGCGTGTACTT

CGCTTCTACCGAGAAGTCCAACATCATCCGGGGCTGGATCTTTGGCACCACACTGG

ACAGCAAGACACAGTCTCTGCTGATCGTGAACAATGCCACCAACGTGGTCATCAAG

GTGTGCGAGTTCCAGTTTTGTAATGATCCTTTCCTGGGCGTGTACTATCATAAGAAC

AATAAGTCCTGGATGGAGAGCGAGTTTCGCGTGTATAGCTCTGCTAACAATTGTAC

ATTTGAGTACGTGAGCCAGCCATTCCTGATGGACCTGGAGGGCAAGCAGGGCAATT

TCAAGAACCTGAGAGAGTTCGTGTTTAAGAATATCGATGGCTACTTCAAGATCTAC

AGCAAGCACACCCCTATCAACCTGGTGCGCGACCTGCCACAGGGCTTCTCTGCCCTG

GAGCCTCTGGTGGATCTGCCAATCGGCATCAACATCACCAGGTTTCAGACACTGCTG

GCTCTGCATCGGTCTTACCTGACACCTGGCGACTCCAGCTCTGGATGGACCGCTGGA

-continued

GCTGCTGCTTACTATGTGGGCTATCTGCAGCCAAGAACCTTCCTGCTGAAGTACAAC

GAGAATGGCACCATCACAGACGCCGTGGATTGCGCTCTGGATCCACTGTCCGAGAC

CAAGTGTACACTGAAGAGCTTTACCGTGGAGAAGGGCATCTATCAGACATCCAATT

TC*AGAGTGCAGCCCACCGAGAGCATCGTGCGCTTTCCAAATATCACAAACCTGTGCCCCTTTGGCGAGGTGTTCAACGC*

*CACCCGCTTCGCTTCCGTGTACGCCTGGAATAGAAAGCGCATCTCCAACTGCGTGGCTGACTATAGCGTGCTGTACAACT*

*CCGCCAGCTTCTCTACCTTTAAGTGCTATGGCGTGTCCCCCACAAAGCTGAATGACCTGTGCTTTACCAACGTGTACGCC*

*GATAGCTTCGTGATCAGAGGCGACGAGGTGCGCCAGATCGCTCCAGGACAGACAGGCAAGATCGCCGACTACAATTATA*

*AGCTGCCTGACGATTTCACCGGCTGCGTGATCGCTTGGAACTCCAACAATCTGGATAGCAAAGTGGGCGGCAACTACAAT*

*TATCTGTACAGGCTGTTTCGGAAGAGCAATCTGAAGCCTTTCGAGAGGGACATCTCTACAGAGATCTACCAGGCCGGCTC*

*CACCCCATGCAATGGCGTGGAGGGCTTTAACTGTTATTTCCCCCTGCAGTCTTACGGCTTCCAGCCTACCAACGGCGTGG*

*GCTATCAGCCATACCGGGTGGTGGTGCTGTCTTTTGAGCTGCTGCACGCTCCAGCTACAGTGTGCGGACCTAAGAAGTCC*

*ACCAATCTGGTGAAGAACAAGTGCGTGAACTTC*AACTTCAACGGACTGACCGGCACAGGCGTGCTG

ACCGAGAGCAACAAGAAGTTCCTGCCCTTTCAGCAGTTCGGCAGGGACATCGCTGA

TACCACAGACGCCGTGCGGGACCCACAGACCCTGGAGATCCTGGATATCACACCCT

GCTCTTTCGGCGGCGTGTCCGTGATCACACCTGGCACCAATACATCTAACCAGGTGG

CCGTGCTGTATCAGGACGTGAATTGTACCGAGGTGCCTGTGGCCATCCACGCTGATC

AGCTGACCCCAACATGGAGGGTGTACAGCACCGGCTCTAACGTGTTTCAGACACGG

GCTGGATGTCTGATCGGAGCTGAGCATGTGAACAATTCCTATGAGTGCGACATCCC

CATCGGCGCTGGCATCTGTGCCAGCTACCAGACCCAGACAAACAGCCCTAGGAGGG

CT*GCTTCT*GTGGCTTCCCAGAGCATCATCGCCTATACCATGTCCCTGGGCGCTGAGA

ATAGCGTGGCCTACTCCAACAATAGCATCGCTATCCCAACCAACTTCACAATCTCCG

TGACCACAGAGATCCTGCCCGTGAGCATGACCAAGACATCTGTGGACTGCACAATG

TATATCTGTGGCGATTCTACCGAGTGCTCCAACCTGCTGCTGCAGTACGGCAGCTTT

TGTACCCAGCTGAATAGGGCTCTGACAGGCATCGCCGTGGAGCAGGATAAGAACAC

ACAGGAGGTGTTCGCCCAGGTGAAGCAGATCTACAAGACCCCACCCATCAAGGACT

TTGGCGGCTTCAACTTCTCCCAGATCCTGCCTGATCCATCTAAGCCCTCCAAG*GCTA*

GCTTTATCGAGGACCTGCTGTTCAACAAGGTGACCCTGGCTGATGCCGGCTTCATCA

AGCAGTATGGCGATTGCCTGGGCGACATCGCTGCCAGGGACCTGATCTGTGCTCAG

AAGTTTAATGGCCTGACCGTGCTGCCTCCACTGCTGACAGATGAGATGATCGCCCA

GTACACATCTGCCCTGCTGGCTGGCACCATCACATCCGGATGGACCTTCGGCGCTGG

AGCTGCCCTGCAGATCCCTTTTGCTATGCAGATGGCCTATCGGTTCAACGGCATCGG

CGTGACCCAGAATGTGCTGTACGAGAACCAGAAGCTGATCGCTAATCAGTTTAACT

CCGCCATCGGCAAGATCCAGGACTCTCTGTCCAGCACAGCTTCCGCCCTGGGCAAG

CTGCAGGATGTGGTGAATCAGAACGCTCAGGCCCTGAATACCCTGGTGAAGCAGCT

GTCTTCCAACTTCGGCGCTATCAGCTCTGTGCTGAATGATATCCTGAGCAGACTGGA

C*CCACCT*GAGGCTGAGGTGCAGATCGACAGGCTGATCACAGGCCGGCTGCAGAGCCTG

-continued

```
CAGACCTACGTGACACAGCAGCTGATCAGAGCTGCCGAGATCCGCGCTTCTGCCAA

CCTGGCTGCCACCAAGATGTCTGAGTGCGTGCTGGGCCAGTCCAAGCGCGTGGACT

TTTGTGGCAAGGGCTATCACCTGATGAGCTTCCCCCAGTCTGCTCCTCACGGCGTGG

TGTTTCTGCATGTGACCTACGTGCCCGCCCAGGAGAAGAACTTCACCACAGCTCCTG

CCATCTGCCACGATGGCAAGGCCCATTTTCCCAGAGAGGGCGTGTTCGTGTCTAACG

GCACCCATTGGTTTGTGACACAGCGCAATTTCTACGAGCCTCAGATCATCACCACAG

ACAATACCTTCGTGTCCGGCAACTGTGACGTGGTCATCGGCATCGTGAACAATACC

GTGTATGATCCCCTGCAGCCTGAGCTGGACTCTTTTAAGGAGGAGCTGGATAAGTA

CTTCAAGAATCACACCTCCCCAGACGTGGATCTGGGCGACATCTCCGGCATCAATG

CTAGCGTGGTGAACATCCAGAAGGAGATCGACAGGCTGAACGAGGTGGCCAAGAA

TCTGAACGAGTCTCTGATCGATCTGCAGGAGCTGGGCAAGTATGAGCAGTACATCA

AGTGGCCAGGATCTGGATCCGGCAGCAGGTCTCTGGTGCCACGGGGCTCTCCAggatccggatatatcc

cagaggctcccagagacggacaggcttacgtgcgcaaggatggcgagtgggtgctgctgtccaccttcctgGGCGGCTCTGGA

GGAGGAGGATCCGGAGGAGGAGGATCCGGCAGCGAGCCTAAGTCCTGCGACAAGA

CCCACACAAGCCCACCATCTCCAGCTCCTGAGCTGCTGGGAGGACCAAGCGTG

TTCCTGTTTCCTCCAAAGCCTAAGGATACACTGATGATCTCTCGGACCCCAGAG

GTGACATGCGTGGTGGTGGACGTGTCCCACGAGGACCCCGAGGTGAAGTTTAA

CTGGTACGTGGACGGCGTGGAGGTGCATAATGCTAAGACCAAGCCAAGGGAG

GAGCAGTATAACAGCACATACCGGGTGGTGTCTGTGCTGACCGTGCTGCATCA

GGATTGGCTGAACGGCAAGGAATACAAGTGCGCTGTGAGCAATAAGGCCCTGC

CAGCTCCCATCGAGAAGACAATCTCTAAGGCCAAGGGCCAGCCTAGAGAGCCA

CAGGTGTATACCCTGCCACCTTCCCGCGACGAGCTGACCAAGAATCAGGTGAG

CCTGACATGTCTGGTGAAGGGCTTCTACCCTAGCGATATCGCTGTGGAGTGGG

AGTCTAACGGCCAGCCAGAGAACAATTATAAGACCACACCACCCGTGCTGGAC

TCCGATGGCAGCTTCTTTCTGTACAGCAAGCTGACAGTGGACAAGTCTCGGTG

GCAGCAGGGCAACGTGTTCTCCTGCTCCGTGATGCATGAGGCCCTGCACAACC

ATTACACCCAGAAGAGCCTGTCTCTGTCCCCTGGCAAGtgaCTCGAG
```

or a variant thereof. In some aspects, the variant can a sequence 50%, 55%, 65%, 70%, 75%, 80%, 90%, 95%, 96%, 97%, 98%, or 99% identical to the sequence of SEQ ID NO:2. The double underlined sequence represents a KpnI cloning site. The bold, lowercase letter sequence represents a Kozak sequence. The underlined sequence represents a native signal peptide of S protein. The bold subscript sequence represents the RBD of S1. The bold underline sequence represents the mutated S1/S2 cleavage site (R685A in italics, no change in S686). The bold letter and bold underline sequence represents a mutation at the S2' cleavage site (R816A in italics, no change in S817). The bold, italics, and subscript sequence represents K986P and V987P mutations which allow the S protein to keep the Pre-fusion conformation. The dotted underline and subscript sequence represents a 6GS (glycine-serine) linker. The lowercase letters represents the foldon domain from T4 fibrin. The dotted underline, italicized sequence represents a 14GS (glycine-serine) linker. The bold sequence is human IgG1. The dotted underline sequence AGC represents a cysteine to serine mutation (C226S of full length human IgG1, C11S of the Fc fragment disclosed herein) in human IgG1 to produce a monomer human IgG1. The dotted underline sequence TCT represents a cysteine to serine mutation (C229S of full length human IgG1, C14S of the Fc fragment disclosed herein) in human IgG1 to produce a monomer human IgG1. The italicized, underlined sequence represents a mutation preventing complement binding (K322A of full length human IgG1, K107A of the Fc fragment disclosed herein) in human IgG1. The bold lowercase sequence represents a stop codon in IgG1. The squiggly underline represents an XhoI cloning site. Nucleic acids 58 to 3594 represent the SARS-Cov-2 spike protein. Nucleic acids 3697-3783 represent the foldon domain of T4 fibrin. Nucleic acids 3829-4527 represent a monomeric Fc IgG1 fragment.

In some aspects, disclosed are nucleic acid sequences comprising a monomeric Fc fragment of an immunoglobulin recognized by a FcRn sequence; a SARS-COV-2 S1 protein sequence; and a trimerization domain sequence. For example, disclosed are nucleic acid sequences comprising the sequence of (SEQ ID NO: 4)

*GGTACC*gccaccATGTTCGTGTTTCTGGTGCTGCTGCCACTGGTGTCCAGCCAGTGCGT

GAACCTGACCACAAGAACCCAGCTGCCCCCTGCCTATACCAATTCTTTCACAAGAG

GCGTGTACTATCCAGACAAGGTGTTTCGCTCTTCCGTGCTGCACAGCACACAGGATC

TGTTTCTGCCCTTCTTTTCTAACGTGACCTGGTTCCACGCCATCCACGTGTCCGGCAC

CAATGGCACAAAGAGGTTCGACAATCCTGTGCTGCCCTTCAACGATGGCGTGTACTT

CGCTTCTACCGAGAAGTCCAACATCATCCGGGGCTGGATCTTTGGCACCACACTGG

ACAGCAAGACACAGTCTCTGCTGATCGTGAACAATGCCACCAACGTGGTCATCAAG

GTGTGCGAGTTCCAGTTTTGTAATGATCCTTTCCTGGGCGTGTACTATCATAAGAAC

AATAAGTCCTGGATGGAGAGCGAGTTTCGCGTGTATAGCTCTGCTAACAATTGTAC

ATTTGAGTACGTGAGCCAGCCATTCCTGATGGACCTGGAGGGCAAGCAGGGCAATT

TCAAGAACCTGAGAGAGTTCGTGTTTAAGAATATCGATGGCTACTTCAAGATCTAC

AGCAAGCACACCCCTATCAACCTGGTGCGCGACCTGCCACAGGGCTTCTCTGCCCTG

GAGCCTCTGGTGGATCTGCCAATCGGCATCAACATCACCAGGTTTCAGACACTGCTG

GCTCTGCATCGGTCTTACCTGACACCTGGCGACTCCAGCTCTGGATGGACCGCTGGA

GCTGCTGCTTACTATGTGGGCTATCTGCAGCCAAGAACCTTCCTGCTGAAGTACAAC

GAGAATGGCACCATCACAGACGCCGTGGATTGCGCTCTGGATCCACTGTCCGAGAC

CAAGTGTACACTGAAGAGCTTTACCGTGGAGAAGGGCATCTATCAGACATCCAATT

TC*AGAGTGCAGCCCACCGCGCGCATCGTGGCTTTCCAAATATCAAACCTGTGCCCTTTGGCGAGGTGTTCAACGC*

*CACCCGCTTCGCTTCCGTGTACGCCTGGAATAGAAAGCGCATCTCCAACTGCGTGGCTGACTATAGCGTGCTGTACAACT*

*CCGCCAGCTTCTCTCTACCTTTAAGTGCTATGGCGTGTCCCCCACAAAGCTGAATGACCTGTGCTTTACCAACGTGTACGCC*

*GATAGCTTCGTGATCAGAGGCGACGAGGTGCGCCAGATCGCTCCAGGACAGACAGGCAAGATCGCCGACTACAATTATA*

*AGCTGCCTGACGATTTCACCGGCTGCGTGATCGCTTGGAACTCCAACAATCGGATAGCAAAGTGGGCAACTACAAT*

*TATCTGTACAGGCTGTTTCGGAAGAGCAATCTGAAGCCTTTCGAGAGGGACATCTCTACAGAGATCTACCAGGCCGGCTC*

*CACCCCATGCAATGGCGTGGAGGGCTTTACTGTTATTTCCCCCTGCAGTCTTACGGCTTCCAGCCTACCAACGGCGTGG*

*GCTATCAGCCATACCGGGTGGTGGTGCTGCTTTTGAGCTGCTGCACGCTCCAGCTACAGTGTGCGGACCTAAGAAGTCC*

*ACCAATCTGGTGAAGAACAAGTGCGTGAACTTC*AACTTCAACGGACTGACCGGCACAGGCGTGCTG

ACCGAGAGCAACAAGAAGTTCCTGCCCTTTCAGCAGTTCGGCAGGGACATCGCTGA

TACCACAGACGCCGTGCGGGACCCACAGACCCTGGAGATCCTGGATATCACACCCT

GCTCTTTCGGCGGCGTGTCCGTGATCACACCTGGCACCAATACATCTAACCAGGTGG

CCGTGCTGTATCAGGACGTGAATTGTACCGAGGTGCCTGTGGCCATCCACGCTGATC

AGCTGACCCCCAACATGGAGGGTGTACAGCACCGGCTCTAACGTGTTTCAGACACGG

GCTGGATGTCTGATCGGAGCTGAGCATGTGAACAATTCCTATGAGTGCGACATCCC

CATCGGCGCTGGCATCTGTGCCAGCTACCAGACCCAGACAAACAGCCCTAGGAGGG

-continued

CTGCTGGATCTGGATCCGGCAGCAGGTCTCTGGTGCCACGGGGCTCTCCAggatccggatatatcccagag gctcccagagacggacaggcttacgtgcgcaaggatggcgagtgggtgctgctgtccaccttcctgGGCGGCTCTGGAGGA

GGAGGATCCGGAGGAGGAGGATCCGGCAGCGAGCCTAAGTCCTGCGACAAGACCC

ACACAAGCCCACCATCTCCAGCTCCTGAGCTGCTGGGAGGACCAAGCGTGTTC

CTGTTTCCTCCAAAGCCTAAGGATACACTGATGATCTCTCGGACCCCAGAGGT

GACATGCGTGGTGGTGGACGTGTCCCACGAGGACCCCGAGGTGAAGTTTAACT

GGTACGTGGACGGCGTGGAGGTGCATAATGCTAAGACCAAGCCAAGGGAGGA

GCAGTATAACAGCACATACCGGGTGGTGTCTGTGCTGACCGTGCTGCATCAGG

ATTGGCTGAACGGCAAGGAATACAAGTGCGCTGTGAGCAATAAGGCCCTGCCA

GCTCCCATCGAGAAGACAATCTCTAAGGCCAAGGGCCAGCCTAGAGAGCCACA

GGTGTATACCCTGCCACCTTCCCGCGACGAGCTGACCAAGAATCAGGTGAGCC

TGACATGTCTGGTGAAGGGCTTCTACCCTAGCGATATCGCTGTGGAGTGGGAG

TCTAACGGCCAGCCAGAGAACAATTATAAGACCACACCACCCGTGCTGGACTC

CGATGGCAGCTTCTTTCTGTACAGCAAGCTGACAGTGGACAAGTCTCGGTGGC

AGCAGGGCAACGTGTTCTCCTGCTCCGTGATGCATGAGGCCCTGCACAACCAT

TACACCCAGAAGAGCCTGTCTCTGTCCCCTGGCAAGtgaCTCGAG or a variant sequence 50%, 55%, 65%, 70%, 75%, 80%, 90%, 95%, 96%, 97%, 98%, or 99% identical to the sequence of SEQ ID NO:4. The double underlined sequence represents a KpnI cloning site. The bold, lowercase letter sequence represents a Kozak sequence. The underlined sequence represents a native signal peptide of S protein. The bold subscript sequence represents the RBD of S1. The italics and bold underline sequence represents the mutated S1/S2 cleavage site (R685A of S protein in italics). The dotted underline sequence represents a 6GS (glycine-serine) linker. The lowercase letters represents the foldon domain from T4 fibrin. The dotted underline, italicized sequence represents a 14GS (glycine-serine) linker. The bold sequence is human IgG1. The dotted underline sequence AGC represents a cysteine to serine mutation (C226S of full length human IgG1, C11S of the Fc fragment disclosed herein) in human IgG1 to produce a monomer human IgG1. The dotted underline sequence TCT represents a cysteine to serine mutation (C229S of full length human IgG1, C14S of the Fc fragment disclosed herein) in human IgG1 to produce a monomer human IgG1. The italicized, underlined sequence represents a mutation preventing complement binding (K322A of full length human IgG1, K107A of the Fc fragment disclosed herein) in human IgG1. The bold lowercase sequence represents a stop codon in IgG1. The squiggly underline represents an XhoI cloning site. Nucleic acids 58 to 2067 represent the SARS-Cov-2 S1 protein sequence. Nucleic acids 2113 to 2199 represent the foldon domain of T4 fibrin. Nucleic acids 2245 to 2943 represent a monomeric Fc IgG1 fragment.

In some aspects, disclosed are nucleic acid sequences comprising a monomeric Fc fragment of an immunoglobulin recognized by a FcRn sequence; a SARS-COV-2 RBD protein sequence; and a trimerization domain sequence. For example, disclosed are nucleic acid sequences comprising the sequence of (SEQ ID NO: 6)

GGTACCgccaccATGTTCGTGTTTCTGGTGCTGCTGCCACTGGTGTCCAGCCAGTGCGT

GAGAGTGCAGCCCACCGAGAGCATCGTGCGCTTTCCAAATATCACAAACCTGTGCCCCTTT

GGCGAGGTGTTCAACGCCACCCGCTTCGCTTCCGTGTACGCCTGGAATAGAAAGCGCATCTCCAACTGCGTGGCTGACTA

TAGCGTGCTGTACAACTCCGCCAGCTTCTCTACCTTTAAGTGCTATGGCGTGTCCCCCACAAAGCTGAATGACCTGTGCTT

TACCAACGTGTACGCCGATAGCTTCGTGATCAGAGGCGACGAGGTGCGCCAGATCGCTCCAGGACAGACAGGCAAGATC

GCCGACTACAATTATAAGCTGCCTGACGATTTCACCGGCTGCGTGATCGCTTGGAACTCCAACAATCTGGATAGCAAAGT

-continued

*GGGCGGCAACTACAATTATCTGTACAGGCTGTTTCGGAAGAGCAATCTGAAGCCTTTCGAGAGGGACATCTCTACAGAGA*

*TCTACCAGGCCGGCTCCACCCCATGCAATGGCGTGGAGGGCTTTAACTGTTATTTCCCCCTGCAGTCTTACGGCTTCCAG*

*CCTACCAACGGCGTGGGCTATCAGCCATACCGGGTGGTGGTGCTGTCTTTTGAGCTGCTGCACGCTCCAGCTACAGTGTG*

*CGGACCTAAGAAGTCCACCAATCTGCTGAAGAACAAGTGCGTGAACTT*CGGATCTGGATCCGGCAGCAGG

TCTCTGGTGCCACGGGGCTCTCCAggatccggatatatcccagaggctcccagagacggacaggcttacgtgcgca aggatggcgagtgggtgctgctgtccaccttcctgGGC*GGCTCTGGAGGAGGAGGATCQGGAGGAGGAGG*

*ATCCGGCAGC*GAGCCTAAGTCCTGCGACAAGACCCACACAAGCCCACCATCTCC

AGCTCCTGAGCTGCTGGGAGGACCAAGCGTGTTCCTGTTTCCTCCAAAGCCTA

AGGATACACTGATGATCTCTCGGACCCCAGAGGTGACATGCGTGGTGGTGGAC

GTGTCCCACGAGGACCCCGAGGTGAAGTTTAACTGGTACGTGGACGGCGTGG

AGGTGCATAATGCTAAGACCAAGCCAAGGGAGGAGCAGTATAACAGCACATAC

CGGGTGGTGTCTGTGCTGACCGTGCTGCATCAGGATTGGCTGAACGGCAAGGA

**ATACAAGTGC*GCT*GTGAGCAATAAGGCCCTGCCAGCTCCCATCGAGAAGACAA**

TCTCTAAGGCCAAGGGCCAGCCTAGAGAGCCACAGGTGTATACCCTGCCACCT

TCCCGCGACGAGCTGACCAAGAATCAGGTGAGCCTGACATGTCTGGTGAAGGG

CTTCTACCCTAGCGATATCGCTGTGGAGTGGGAGTCTAACGGCCAGCCAGAGA

ACAATTATAAGACCACACCACCCGTGCTGGACTCCGATGGCAGCTTCTTTCTGT

ACAGCAAGCTGACAGTGGACAAGTCTCGGTGGCAGCAGGGCAACGTGTTCTCC

TGCTCCGTGATGCATGAGGCCCTGCACAACCATTACACCCAGAAGAGCCTGTC

TCTGTCCCCTGGCAAGtga*CTCGAG* or a variant sequence 50%, 55%, 65%, 70%, 75%, 80%, 90%, 95%, 96%, 97%, 98%, or 99% identical to the sequence of SEQ ID NO: 6.

The double underlined sequence represents a KpnI cloning site. The bold, lowercase sequence represents a Kozak sequence. The underlined sequence represents a native signal peptide of S protein. The bold double underline sequence represents the RBD of S1.

The dotted underline sequence represents a 6GS (glycine-serine) linker. The lowercase letters represents the foldon domain from T4 fibrin. The dotted underline, italicized sequence represents a 14GS (glycine-serine) linker. The bold sequence is human IgG1. The dotted underline sequence AGC represents a cysteine to serine mutation (C226S of full length human IgG1, C11S of the Fc fragment disclosed herein) in human IgG1 to produce a monomer human IgG1. The dotted underline sequence TCT represents a cysteine to serine mutation (C229S of full length human IgG1, C14S of the Fc fragment disclosed herein) in human IgG1 to produce a monomer human IgG1. The italicized, underlined sequence represents a mutation preventing complement binding (K322A of full length human IgG1, K107A of the Fc fragment disclosed herein) in human IgG1. The bold lowercase sequence represents a stop codon in IgG1. The squiggly underline represents an XhoI cloning site. Nucleic acids 61 to 729 represent the SARS-Cov-2 RBD protein sequence. Nucleic acids 775 to 861 represent the foldon domain of T4 fibrin. Nucleic acids 907 to 1605 represent a monomeric Fc IgG1 fragment.

F. Compositions

Disclosed are compositions comprising any of the disclosed peptides, peptide complexes, nucleic acid sequences, or vectors. In some instances, disclosed are compositions comprising a monomeric Fc fragment of an immunoglobulin recognized by a FcRn; a coronavirus antigen; and a trimerization domain. Also disclosed are compositions comprising a monomeric Fc fragment of an immunoglobulin recognized by a FcRn; a SARS-COV-2 antigen; and a trimerization domain.

In some instances, the composition can be a vaccine.

In some instances, the compositions can further comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. Examples of pharmaceutically acceptable carriers include dimyristoylphosphatidyl (DMPC), phosphate buffered saline or a multivesicular liposome. For example, PG: PC: Cholesterol: peptide or PC: peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

In order to enhance the solubility and/or the stability of the disclosed peptides in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also, co-solvents such as alcohols may improve the solubility and/or the stability of the compounds according to the invention in pharmaceutical compositions.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

Because of the ease in administration, oral administration can be used, and tablets and capsules represent the most advantageous oral dosage unit forms in which case solid pharmaceutical carriers are obviously employed. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the compositions of the present invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The disclosed peptides can be formulated and/or administered in or with a pharmaceutically acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug (e.g. peptide) in biodegradable polymers such as polylactide-polyglycolide, poly (orthoesters) and poly (anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

Thus, the compositions disclosed herein can comprise lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subject's lung cells. Regarding liposomes, see, e.g., Brigham et al. Am. J. Resp. Cell. Mol. Biol. 1:95 100 (1989); Felgner et al. Proc. Natl. Acad. Sci USA 84:7413 7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In some instances, disclosed are pharmaceutical compositions comprising any of the disclosed peptides, peptide complexes, nucleic acid sequences or vectors described herein, or a pharmaceutically acceptable salt or solvate thereof, and a pharmaceutically acceptable carrier, buffer, or diluent. In various aspects, the peptide of the pharmaceutical composition is encapsulated in a delivery vehicle. In a further aspect, the delivery vehicle is a liposome, a microcapsule, or a nanoparticle. In a still further aspect, the delivery vehicle is PEG-ylated.

In the methods described herein, delivery of the compositions to cells can be via a variety of mechanisms. As defined above, disclosed herein are compositions comprising any one or more of the peptides described herein and can also include a carrier such as a pharmaceutically acceptable carrier. For example, disclosed are pharmaceutical compositions, comprising the peptides disclosed herein, and a pharmaceutically acceptable carrier. In one aspect, disclosed are pharmaceutical compositions comprising the disclosed peptides, peptide complexes, nucleic acid sequences or vectors. That is, a pharmaceutical composition can be provided comprising a therapeutically effective amount of at least one disclosed peptide or at least one product of a disclosed method and a pharmaceutically acceptable carrier.

In certain aspects, the disclosed pharmaceutical compositions comprise the disclosed peptides (including pharmaceutically acceptable salt(s) thereof) as an active ingredient, a pharmaceutically acceptable carrier, and, optionally, other therapeutic ingredients or adjuvants. The instant compositions include those suitable for nasal, oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In practice, the peptides described herein, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The peptides, peptide complexes, nucleic acid sequences, or vectors described herein, or pharmaceutically acceptable salts thereof, can also be included in pharmaceutical compositions in combination with one or more other therapeutically active compounds.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. Typically, the final injectable form should be sterile and should be effectively fluid for easy syringability. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot on, as an ointment.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a disclosed peptide, and/or pharmaceutically acceptable salts thereof, can also be prepared in powder or liquid concentrate form.

The exact dosage and frequency of administration depends on the particular disclosed peptide, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compositions.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

G. Methods

Disclosed are methods for eliciting a protective immune response against coronavirus, methods of treating or preventing coronavirus infection and methods of reducing coronavirus viral titers in a subject infected with coronavirus. Each of these methods comprise administering an effective amount of a composition comprising any of the peptides, peptide complexes, nucleic acids or vectors disclosed herein. As an example, each of these methods is further described below with regards to the coronavirus being SARS-COV-2 and using the specific coronavirus antigen, a SARS-COV-2 S antigen.

Disclosed are methods for eliciting a protective immune response against SARS-CoV-2 comprising administering to a subject an effective amount of a composition comprising any of the peptides, peptide complexes, nucleic acids or vectors disclosed herein.

Disclosed are methods for eliciting a protective immune response against SARS-CoV-2 comprising administering to a subject an effective amount of a composition comprising a monomeric Fc fragment of an immunoglobulin recognized by a FcRn; a SARS-COV-2 antigen; and a trimerization domain, wherein the administering is to a mucosal epithelium.

Disclosed are methods for eliciting a protective immune response against SARS-CoV-2 comprising administering to a subject an effective amount of a composition comprising a peptide complex, wherein the peptide complex comprises three peptides forming a trimer, wherein each of the three peptides comprises a monomeric Fc fragment of an immunoglobulin recognized by a FcRn; a SARS-COV-2 antigen; and a trimerization domain, wherein the administering is to a mucosal epithelium.

Disclosed are methods of treating or preventing SARS-COV-2 infection in a subject. Disclosed are methods of treating a subject exposed to SARS-COV-2 or at risk of being exposed to SARS-COV-2 comprising administering to a subject an effective amount of a composition comprising any of the peptides, peptide complexes, nucleic acids or vectors disclosed herein.

Disclosed are methods of treating a subject exposed to SARS-COV-2 or at risk of being exposed to SARS-COV-2 comprising administering to the subject an effective amount of a composition comprising a peptide complex, wherein the peptide complex comprises three peptides forming a trimer, wherein each of the three peptides comprises a monomeric Fc fragment of an immunoglobulin recognized by a FcRn; a SARS-COV-2 antigen; and a trimerization domain, wherein the administering is to a mucosal epithelium.

Disclosed are methods of treating a subject exposed to SARS-COV-2 or at risk of being exposed to SARS-COV-2 comprising administering to a subject an effective amount of a composition comprising a monomeric Fc fragment of an immunoglobulin recognized by a FcRn; a SARS-COV-2 antigen; and a trimerization domain, wherein the administering is to a mucosal epithelium. A subject at risk of being exposed to SARS-COV-2 can be a first responder, a health-care worker, a teacher, or anyone knowingly or unknowingly coming in contact with a person infected with SARS-COV-2. In some aspects, treating a subject at risk of being exposed to SARS-COV-2 can result in preventing SARS-COV-2 infection. In some aspects, treating a subject at risk of being exposed to SARS-COV-2 can result in preventing serious symptoms or side-effects of a SARS-COV-2 infection, such as but not limited to, pneumonia, organ failure, cytokine storm, or death.

Disclosed are methods of reducing SARS-COV-2 viral titers in a subject infected with SARS-COV-2 comprising administering to a subject an effective amount of a composition comprising any of the peptides, peptide complexes, nucleic acids or vectors disclosed herein. Disclosed are methods of reducing SARS-COV-2 viral titers in a subject infected with SARS-CoV-2 comprising administering to a subject an effective amount of a composition comprising a monomeric Fc fragment of an immunoglobulin recognized by a FcRn; a SARS-COV-2 antigen; and a trimerization domain, wherein the administering is to a mucosal epithelium.

Disclosed are methods of treating a subject at risk for infection with coronavirus comprising administering an effective amount of a composition comprising any of the peptides, peptide complexes, nucleic acids or vectors disclosed herein.

Disclosed are methods of preventing the spread of coronavirus from a subject infected with a coronavirus to a non-infected subject comprising administering an effective amount of a composition comprising any of the peptides, peptide complexes, nucleic acids or vectors disclosed herein.

Disclosed are methods of preventing coronavirus infection in a subject comprising: administering an effective amount of a composition comprising any of the peptides, peptide complexes, nucleic acids or vectors disclosed herein.

Disclosed herein are methods of reducing coronavirus copy number per cell comprising administering an effective amount of a composition comprising any of the peptides, peptide complexes, nucleic acids or vectors disclosed herein.

In some instances, the mucosal epithelium is selected from the group consisting of: lungs, intestines, trachea, colon, nasal tissue, and vaginal tissue. In some aspects, administering is to a mucosal epithelium is a direct or indirect administration of the disclosed peptides, peptide complexes, nucleic acid sequences or vectors to one or more of the mucosal epithelium described herein.

In some instances, administering is intranasal administering. In some instances, any form of administering that allows for delivery to a mucosal epithelium can be used.

In some instances, an adjuvant is further administered with the composition. In some instances, an adjuvant can be formulated with the peptide into the disclosed compositions. In some instances, the disclosed compositions or peptides can further comprise an adjuvant. Thus, the adjuvant can be administered simultaneously with the peptide. In some instances, the adjuvant is separate from the disclosed compositions and therefore can be administered simultaneously with the composition or separate from the composition. The adjuvant can be, for example, but is not limited to, CpG, MPL, poly [di (sodium carboxylatoethylphenoxy) phosphazene] (PCEP), poly [di (sodium carboxylatophenoxy) phosphazene] (PCPP), the Cholera Toxin-Derived CTA1-DD, Flagellin, IDR1002, α-Galactosylceramide, or saponins. The term "adjuvant" is intended to include any substance which is incorporated into or administered simultaneously with the peptides of the invention and which nonspecifically potentiates the immune response in the subject. Adjuvants include aluminum compounds, e.g., gels, aluminum hydroxide and aluminum phosphate, and Freund's complete or incomplete adjuvant (in which the fusion protein is incorporated in the aqueous phase of a stabilized water in paraffin oil emulsion). The paraffin oil may be replaced with different types of oils, e.g., squalene or peanut oil. Other materials with adjuvant properties include, flagellin, BCG (attenuated *Mycobacterium tuberculosis*), calcium phosphate, levamisole, isoprinosine, polyanions (e.g., poly A: U) leutinan, pertussis toxin, cholera toxin, lipid A, saponins and peptides, e.g. muramyl dipeptide. dimethyl dioctadecyl-ammonium bromide (DDA); monophosphoryl lipid A (MPL); LTK63, lipophilic quaternary ammonium salt-DDA, Trehalose dimycolate and synthetic derivatives, DDA-MPL, DDA-TDM, DDA-TDB, IC-31, aluminum salts, aluminum hydroxyide, aluminum phosphate, potassium aluminum phosphate, Montanide ISA-51, ISA-720, microparticles, immunostimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles including calcium phosphate nanoparticles, combination of soybean oil, emulsifying agents, and ethanol to form a nanoemulsion; AS04, ZADAXIN, or combinations thereof. Rare earth salts, e.g., lanthanum and cerium, may also be used as adjuvants. The amount of adjuvants depends on the subject and the particular peptide used and can be readily determined by one skilled in the art without undue experimentation.

In some aspects, eliciting a protective immune response comprises eliciting neutralizing antibodies. In some aspects, eliciting a protective immune response comprises activating T cells and B cells. In some aspects, the activated T cells and B cells provide a cellular and humoral response, respectively.

In some aspects, an effective amount is that amount of the disclosed peptides, peptide complexes or compositions that will alone, or together with further doses, stimulate an immune response as desired. This may involve the stimulation of a humoral antibody response resulting in an increase in antibody titer in serum, improved mucosal immunity, a clonal expansion of cytotoxic T lymphocytes or tolerance to an antigen, including a self-antigen. It is believed that doses ranging from 1 nanogram/kilogram to 100 milligrams/kilogram, depending upon the mode of administration, will be effective. In some aspects, the preferred range is believed to be between about 500 nanograms and 500 micrograms/kilogram, and most preferably between 1 microgram and 100 micrograms/kilogram. The absolute amount will depend upon a variety of factors, including the peptide, peptide complex, or composition selected, the immune modulation desired, whether the administration is in a single or multiple doses, and individual patient parameters including age, physical condition, size and weight. These factors are well known to those of ordinary skill in the art and can be addressed with no more than routine experimentation.

H. Combination Therapy

Any of the disclosed methods described herein can be performed in combination with one or more of the known standards of care for coronavirus infection. Thus, in some aspects, the methods comprising administering one or more of the disclosed peptide complexes, peptides, compositions or nucleic acids can be combined with an antibody, or antibody cocktail, nanobody, antiviral small molecules, macromolecules of sulfated polysaccharides, and polypeptides. Frequent targets are the viral spike protein, the host angiotensin converting enzyme 2, the host transmembrane protease serine 2, and clathrin-mediated endocytosis. For example, disclosed methods of using TTFields can be performed in combination with one or more of remdesivir (Veklury), Nafamostat, Avigan (favilavir), bamlanivimab, Olumiant and Baricinix (baricitinib), hydroxychloroquine/chloroquine, Casirivimab and imdevimab (formerly REGN-COV2), PTC299, Leronlimab (PRO 140), Bamlanivimab (LY-CoV555), Lenzilumab, Ivermectin, RLF-100 (aviptadil), Metformin (Glucophage, Glumetza, Riomet), AT-527, Actemra (tocilizumab), Niclocide (niclosamide), Convalescent plasma, Pepcid (famotidine), Kaletra (lopinavir-ritonavir), Remicade (infliximab), AZD7442, AZD7442, CT-P59, Heparin (UF and LMW), VIR-7831 (GSK4182136), JS016, Kevzara (sarilumab), SACCOVID (CD24Fc), Humira (adalimumab), COVI-GUARD (STI-1499), Dexamethasone (Dextenza, Ozurdex, others), PB1046, Galidesivir, Bucillamine, PF-00835321 (PF-07304814), Eliquis (Apixaban), Takhzyro (lanadelumab), Hydrocortisone, Ilaris (canakinumab), Colchicine (Mitigare, Colcrys), BLD-2660, Avigan (favilavir/avifavir), Rhu-pGSN (gelsolin), MK-4482, TXA127, LAM-002A (apilimod dimesylate), DNL758 (SAR443122), INOpulse, ABX464, AdMSCs, Losmapimod, Mavrilimumab, or Calquence (acalabrutinib), quinoline-based antimalarials ((hydroxy)-chloroquine and others), RAAS modifiers (captopril, losartan, and others), statins (atorvastatin and simvastatin), guanidino-based serine protease inhibitors (camostat and nafamostat), antibacterials (macrolides, clindamycin, and doxycycline), antiparasitics (ivermectin and niclosamide), cardiovascular drugs (amiodarone, verapamil, and tranexamic acid), antipsychotics (chlorpromazine), antivirals (umifenovir and oseltamivir), DPP-4 inhibitors (linagliptin), JAK inhibitors (baricitinib and others), sulfated glycosaminoglycans (UFH and LMWHs) and polypeptides such as the enzymes DAS181 and rhACE2. They also include the viral spike protein-targeting monoclonal antibodies REGN10933 and REGN10987.

In some aspects, the additional therapeutic agents are selected based on the disease or symptom to be treated. A description of the various classes of suitable pharmacological agents and drugs may be found in Goodman and Gilman, The Pharmacological Basis of Therapeutics, (11th Ed., McGraw-Hill Publishing Co.) (2005). In some aspects, an additional therapeutic agent can be CpG which helps overcome any possible immune tolerance. In some aspects, an additional therapeutic agent can be an anti-viral or any known SARS-COV-2 therapeutic.

In some aspects, an additional therapeutic agent can be MPL (Monophosphoryl Lipid A) or C-di-GMP (Cyclic diguanylate monophosphate, CpG). In some aspects, an additional therapeutic agent can be a toll-like receptor (TLR) agonist, which represent different adjuvants, CpG and MPL are examples.

In some aspects, supplementary immune potentiating agents, such as cytokines, can be delivered in conjunction with the disclosed peptide complexes, peptides and nucleic acids of the invention. The cytokines contemplated are those that will enhance the beneficial effects that result from administering the peptide complexes, peptides and nucleic acids according to the invention. Cytokines are factors that support the growth and maturation of cells, including lymphocytes. It is believed that the addition of cytokines will augment cytokine activity stimulated in vivo by carrying out the methods of the invention. The preferred cytokines are interleukin (IL)-1, IL-2, gamma-interferon and tumor necrosis factor α. Other useful cytokines are believed to be IL-3, IL-4, IL-5, IL-6, IL-7, IL-8, IL-9, IL-10, IL-11, IL-12, IL-13, erythropoietin, leukemia inhibitory factor, oncostatin-M, ciliary neurotrophic factor, growth hormone, prolactin, CD40-ligand, CD27-ligand, CD30-ligand, alpha-interferon, beta-interferon, and tumor necrosis factor β. Other cytokines known to modulate T-cell activity in a manner likely to be useful according to the invention are colony stimulating factors and growth factors including granulocyte and/or macrophage stimulating factors (GM-CSF, G-CSF and CSF-1) and platelet derived, epidermal, insulin-like, transforming and fibroblast growth factors. The selection of the particular cytokines will depend upon the particular modulation of the immune system that is desired. The activity of cytokines on particular cell types is known to those of ordinary skill in the art.

I. Kits

The compositions and materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing the disclosed peptides, the kit comprising monomeric Fc fragment of an immunoglobulin recognized by a.FcRn and a SARS-COV-2 antigen. The kits also can contain vectors.

Examples

FcRn mediates the transfer of IgG across polarized respiratory epithelial cells and prolongs IgG half-life. Described herein is the use of the FcRn to deliver SARS-COV-2 spike antigens to induce protective immunity against SARS-COV-2 virus infection. Intranasal immunization (i.n.) with the trimeric spike proteins that target to FcRn plus a mucosal adjuvant conferred significant protection against lethal virus challenge in human ACE2 transgenic mice. The results demonstrate that FcRn can effectively deliver trimeric spike antigens in the respiratory tract and elicit potent protection against lethal SARS-COV-2 infection. Therefore, FcRn-mediated respiratory immunization can efficiently induce protective respiratory immunity to SARS-COV-2 infection and COVID-19 disease (FIG. 1).

1. Importance of Developing a Nasal Spray Vaccine Against SARS-COV-2 Infection and Transmission Currently, nucleic acid-, viral vector-, and subunit-based vaccines, are in progress or on the market. However, there is still a need to develop a COVID-19 vaccine inducing a high degree of mucosal immunity to block viral spread. The strategy disclosed herein is based on the following: 1) By exploiting a natural IgG transfer pathway, we proved the concept that FcRn-targeted intranasal immunization of mice with trimeric influenza HA-Fc protein induced both local and systemic immune responses and protected mice from infection. We reason that FcRn mucosal delivery could also enhance mucosal uptake of Fc-fused SARS-COV-2 S antigens through intranasal delivery. After epithelial transport, S antigens efficiently bind to Fcγ receptors on dendritic cells. 2). The property of FcRn in protecting IgG from degradation could similarly extend the half-life of S-Fc antigens. This would allow professional antigen presenting cells (APCs), dendritic cell, macrophages, and B cells to sample and present S antigens for a long time in APCs that enhance T cell activation. 3). The full-length proteins S, S1, or RBD in SARS-COV-2 have been proposed as major vaccine antigens because they induce neutralizing antibodies that prevent host cell attachment and infection by virus. 4). We have produced a trimeric form of SARS-COV-2 S-Fc, S1-Fc, RBD-Fc antigens, the mice intranasally immunized with trimeric S-Fc, S1-Fc or RBD-Fc antigens developed specific neutralizing antibodies. 5). FcRn-mediated IgG transport is well-conserved across species, human FcRn is expected to transport SARS-COV-2 antigens in humans.

2. Developing an Effective Mucosal Vaccine Against SARS-COV-2.

SARS-COV-2 seems more contagious for quickly and easily spreading among people. The virus can spread via droplets or aerosol from the infected individuals with or without symptoms. Given the main cause of patient death is pneumonia, therefore achieving an effective and long-lasting immunity in the respiratory tract would better prevent or control the SARS-COV-2 spread and infection in the community. However, to elicit resident memory T and B cells in the lung, vaccine antigens must be delivered into the lungs. It has been shown that FcRn mucosal delivery can induce potent protection from influenza infection. FcRn can similarly deliver SARS-COV-2 S antigens across the respiratory barrier, thus inducing protective respiratory immunity to SARS-COV-2 viruses. It is expected that mucosal immunity can prevent nasal infection or shedding of the virus. FcRn-targeted delivery represents an important path for developing a mucosal vaccine against SARS-COV-2.

3. Developing a Safe SARS-COV-2 Mucosal Vaccine in the Young or Elderly Population.

Elderly people are most likely to develop severe forms of COVID-19, however, achieving immune protection by a vaccine may be challenging in the elderly. Also, although infected children have less symptoms, the immunization of the young population would reduce viral transmission. Since vaccine preparation mainly contains Spike proteins, FcRn mucosal delivery would mitigate the risk and develop an effective and safe immunity in both young and elderly. Overall, FcRn-targeted mucosal vaccination can help control the COVID-19 pandemic but not only preventing the disease severity in individuals, but also stopping viral infection and spread among people.

4. Expression of SARS-COV-2 S, S1, or RBD Antigen that is Fused to Human IgG 1 Fc.

The rationale for using human IgG1 is consistent with the fact that it has the highest affinity for activating FcγRI, but the lowest affinity for inhibitory FcγRIIB. Because IgG Fc normally forms a disulfide-bonded dimer, a monomeric Fc was created by substituting cysteines 226 and 229 of human IgG1 with serine to eliminate the disulfide bonds. In IgG Fc, the complement C1q-binding motif was eliminated (K322A) (FIG. 2), allowing production of a non-lytic vaccine antigen.

Figure 2:
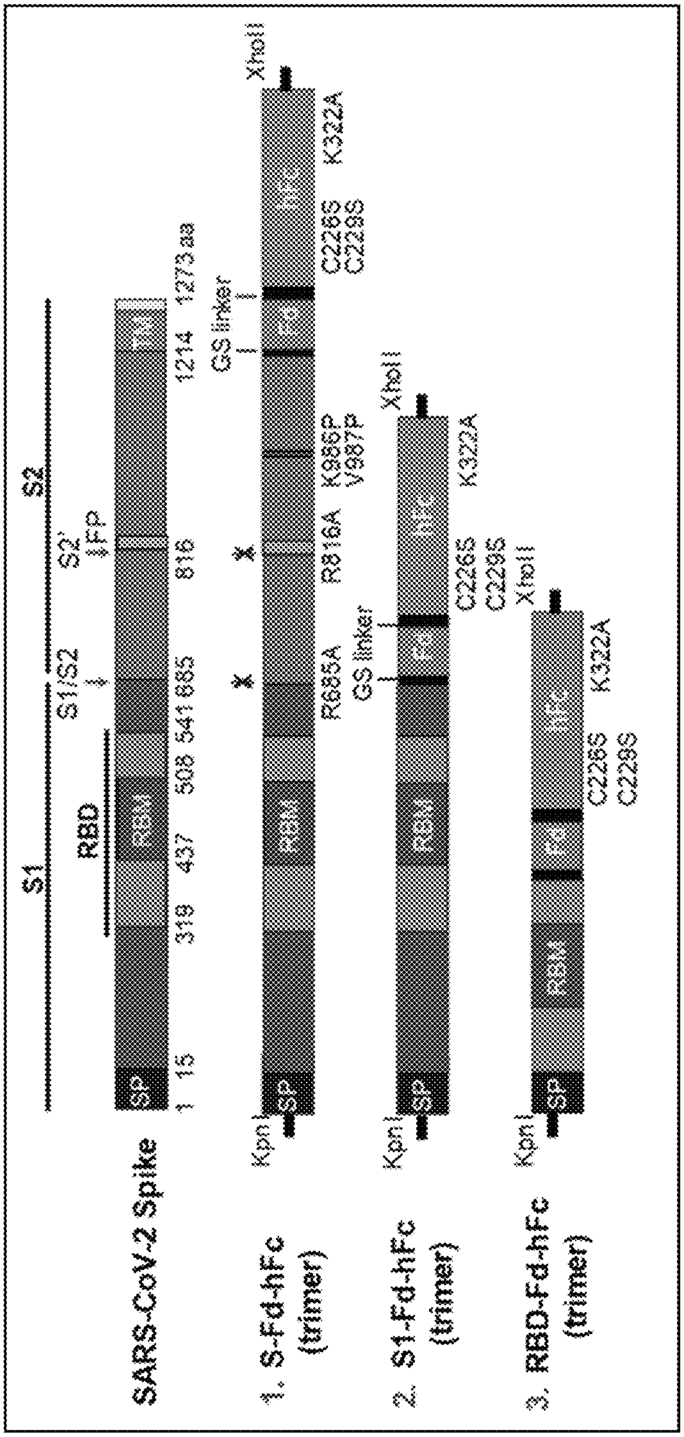
FIG. 2 shows a schematic illustration of the fusion of S, S1, RBD, the foldon, and Fcγ cDNA to create a trimeric S-Fc fusion gene. S, Spike; SP, signal peptide; RBD, receptor binding domain; FP, fusion peptide; TM, transmembrane domain. Fd; Foldon domain, cleavage site; R816A, mutation at S2' cleavage site; K986P/V987P, mutation keeping pre-fusion structure; C226S/C229S, mutation for a monomer hIgG1; K322A, mutation.

The entire amino acid (aa) sequence of the SARS-COV-2 was retrieved from Genbank (MN908947). the S gene of SARS-COV-2. The S gene was cloned into eukaryotic expression plasmid pcDNA3 to generate the envelope recombinant plasmids pcDNA3-S(FIG. 2). During SARS-COV-2 infection, the S precursor is cleaved into S1 and S2. To produce a non-cleavable S protein, mutagenesis was performed at the cleavage site (R685A/R816A) of the S gene to keep the S protein in pre-cleavage conformation. The maintenance of a native conformational structure of SARS-COV-2 Spike antigen in a prefusion state would be critical for maximizing the immunogenicity induced by intranasal vaccination. To maintain the S protein in a prefusion state, two mutations (K986P and V987P) were introduced.

Figure 3:
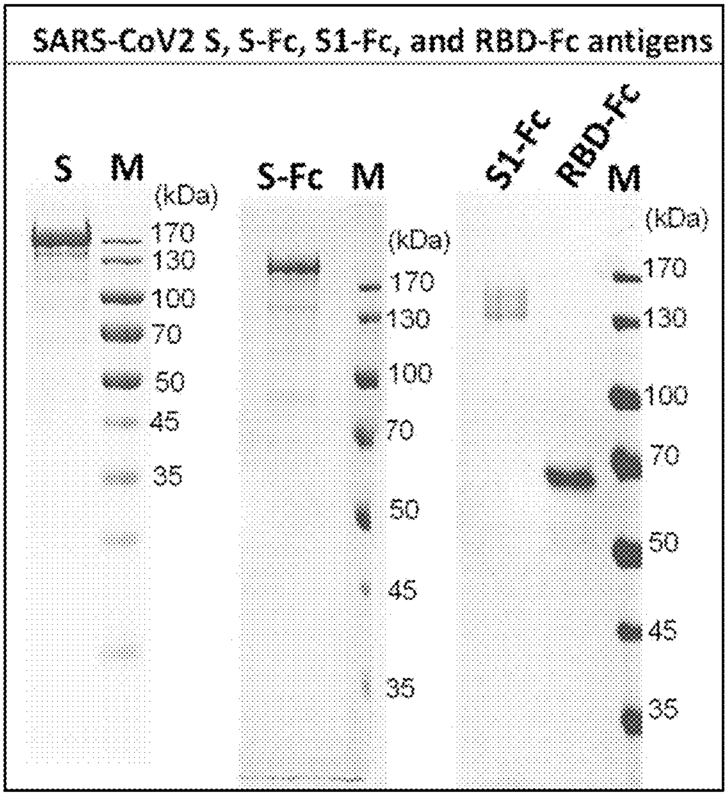
FIG. 3 shows a protein gel demonstrating the production of SARS-COV-2 S, S-Fc, S1-Fc, and RBD-Fc fusion proteins. CHO or 293T cells were transfected with plasmids encoding S, S-Fc/wt, S1-Fc/wt, or RBD-Fc/wt. The stable cell lines were selected and cloned. The proteins in supernatants were purified with anti-His beads for S antigen or Protein A/G-agarose beads. The purified proteins were detected by Commassie blue.

The SARS-COV-2 S protein naturally exists as a trimer. To facilitate the trimerization of S protein, a foldon domain from T4 bacteriophage fibritin protein was engineered to the C-terminus of S (residues 15-1214), S1 (residues 15-672), and RBD (residues 319-540) genes. As described above, the monomeric human IgG1 Fc/wt was fused in frame with the S-foldon, S1-foldon, and RBD-foldon, generating S-Fc ((FIG. 2, construct #1), S1-Fc (construct #2) and RBD-Fc (construct #3), respectively. In a Coomassie blue staining, the S, S-Fc, S1-Fc, and RBD-Fc proteins were secreted from 293T or CHO cells (FIG. 3). In a Western blot, the secreted S-Fc/wt, S1-Fc/wt, RBD-Fc/wt proteins were monomers under non-reducing conditions. This confirmed that removal of the disulfide bonds eliminated Fc dimerization. To determine whether S-Fc protein binds to FcRn, it was tested whether S-Fc interacts with Protein A because of the IgG Fc binding sites for both FcRn and Protein A overlap. The S-Fc interacted with Protein A strongly indicating that S-Fc proteins maintain the structure required to interact with FcRn.

5. Intranasal Immunization of Mouse with S-Fc, S1-Fc or RBD-Fc Induced S-Specific Antibody Immune Responses.

Figure 4:
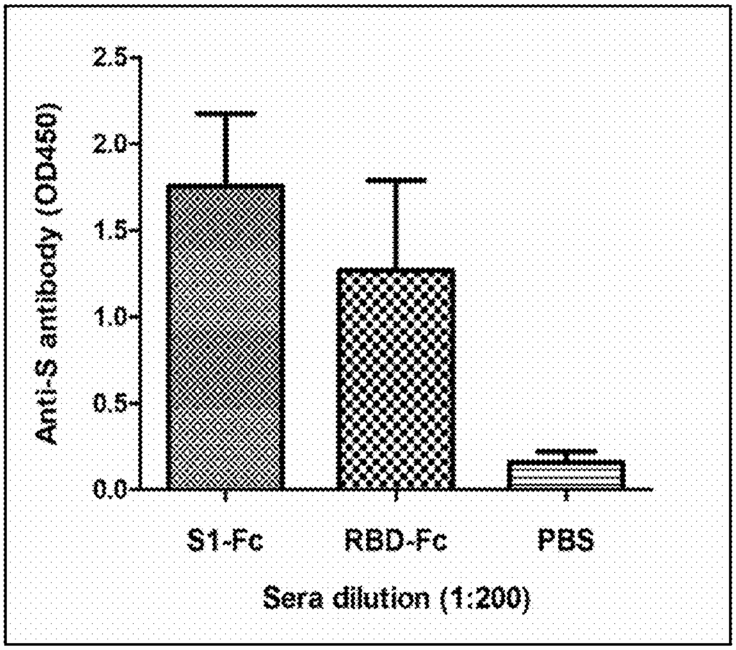
FIG. 4 shows that intranasal immunization of mice with S-Fc, S1-Fc or RBD-Fc induced S-specific antibody immune responses. Top panel: Intranasal delivery of both S1-Fc or RBD-Fc antigens induces Spike-specific antibody immune responses. Five μg of purified spike S1-Fc, RBD-Fc, or PBS in combination with 10 μg of CpG were intranasally (i.n.) administered into mouse (n=5). Spike-specific antibody titers in sera were measured 14 days after boost by ELISA. The data represent mean±S.E.M. Bottom panel: SARS-COV-2 neutralization by serum antibodies. Neutralization assays were performed by incubating SARS-COV-2 pseudoviruses (50 ul) with 1:10 dilution of the pooled mouse sera at 37° C. for 1 hr. After incubation, the 100 μL of the sera-pseudovirus mixture were added to ACE2/293T cells. After 72 hr incubation, luciferase activity was measured using luciferin-containing substrate. Controls included cell-only control, virus without any antibody control. The PBS immunized mice serum as a negative control. The average percentage inhibition (at 1:10 serum dilution) for each group are shown. Data is shown for 5 mice per group.
Figure 4:
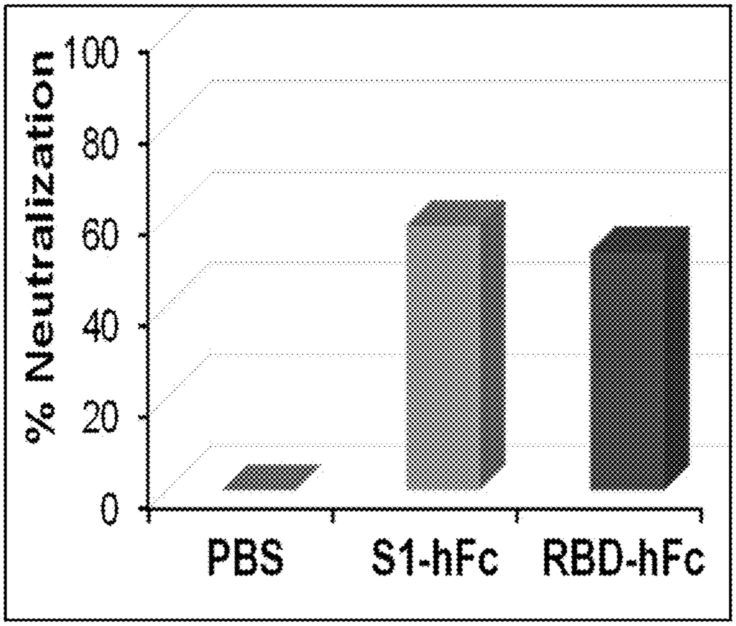

Whether mice intranasally (i.n.) immunized with IgG Fc-fused S1 and RBD proteins can develop antibody immune responses was tested. CpG1826 was co-administrated to overcome possible mucosal tolerance. Briefly, mice were i.n. immunized with 10 μg of affinity-purified S1-Fc, RBD-Fc protein, or PBS in combination with 10 μg CpG, and boosted 2 weeks later with the same dose. Significantly higher titers of total IgG in sera, measured by ELISA, were detected in the S1-Fc or RBD-Fc immunized mice when compared with PBS-immunized mice (FIG. 4, left panel).

SARS-COV-2 neutralization was measured using SARS-COV-2-FBLuc in a single-cycle pseudovirus neutralization assay in ACE2/293T cells. Pseudovirions were produced by cotransfection Lenti-X 293T cells with pMLV-gag-pol, pFBluc, and pcDNA 3.1 SARS-COV-2 S (BEI Resources) using Lipofectamine 3000. The supernatant was harvested at 72 hr after transfection. For the neutralization assay, 50 μl of SARS-COV-2 S pseudovirions was preincubated with an equal volume of medium, containing serum at varying dilutions at room temperature for 1 hour; then, virus-antibody mixtures were added to ACE2/293T cells. Cells were lysed 72 hour later, and luciferase activity was measured using luciferin-containing substrate. The average percent inhibitions by mouse intranasal vaccination are shown in FIG. 4 (right panel). Control sera (control) did not neutralize SARS-COV-2 in this assay. Sera generated by S1 and RBD showed 50 to 60% virus neutralization after vaccination.

Figure 5:
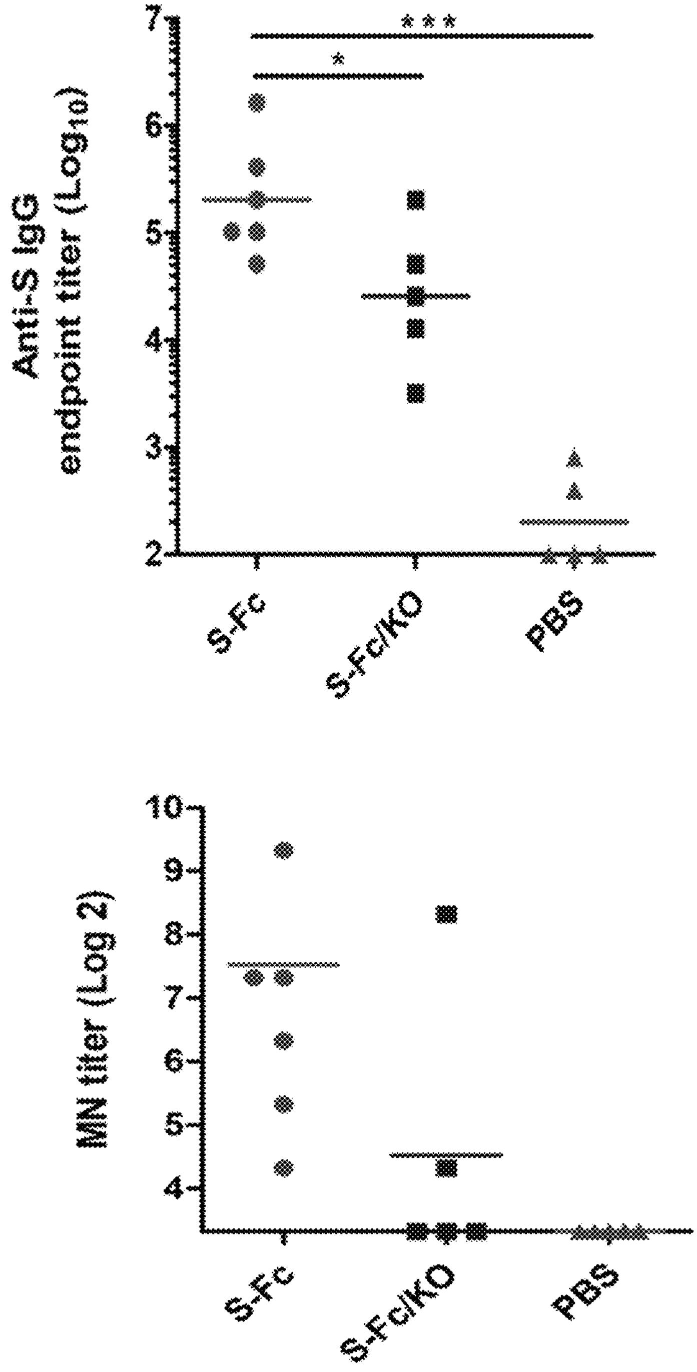
FIG. 5 shows the immune response is FcRn-dependent. Top. S-specific IgG titers in sera were measured by ELISA 14 days after boosting. Bottom. The neutralization antibody titers in the sera were expressed as the reciprocal of the twofold serial dilution preventing the appearance of the cytopathogenic effect (CPE) in Vero E6 cells. KO: FcRn knockout mice

Whether FcRn-dependent respiratory transport augments the immune responses of S antigen was also tested. Wild-type mice (N=6) or FcRn knockout mice (KO) (N=5) were intranasally (i.n.) immunized with 10 μg of S-Fc, or PBS in combination with 10 μg CpG, and boosted 2 weeks later with the same dose. Significantly higher titers of S-specific IgG in sera were seen in the S-Fc immunized mice when compared with that of S-Fc-immunized FcRn KO mice or PBS-treated groups of mice 2 weeks after the boost (FIG. 5, Left). Moreover, sera from the S-Fc/wt immunized mice exhibited strong neutralizing activity relative to FcRn KO or PBS control groups (FIG. 5, Right). Overall, the data indicate that Fc-fused S, S1 or RBD antigens administered via the intranasal route can induce the S-specific neutralizing antibody, this immune response should depend on FcRn transport.

6. FcRn-Targeted Nasal Vaccination Leads to Increased Protection Against Lethal SARS-CoV-2 Infection.

Figure 6:
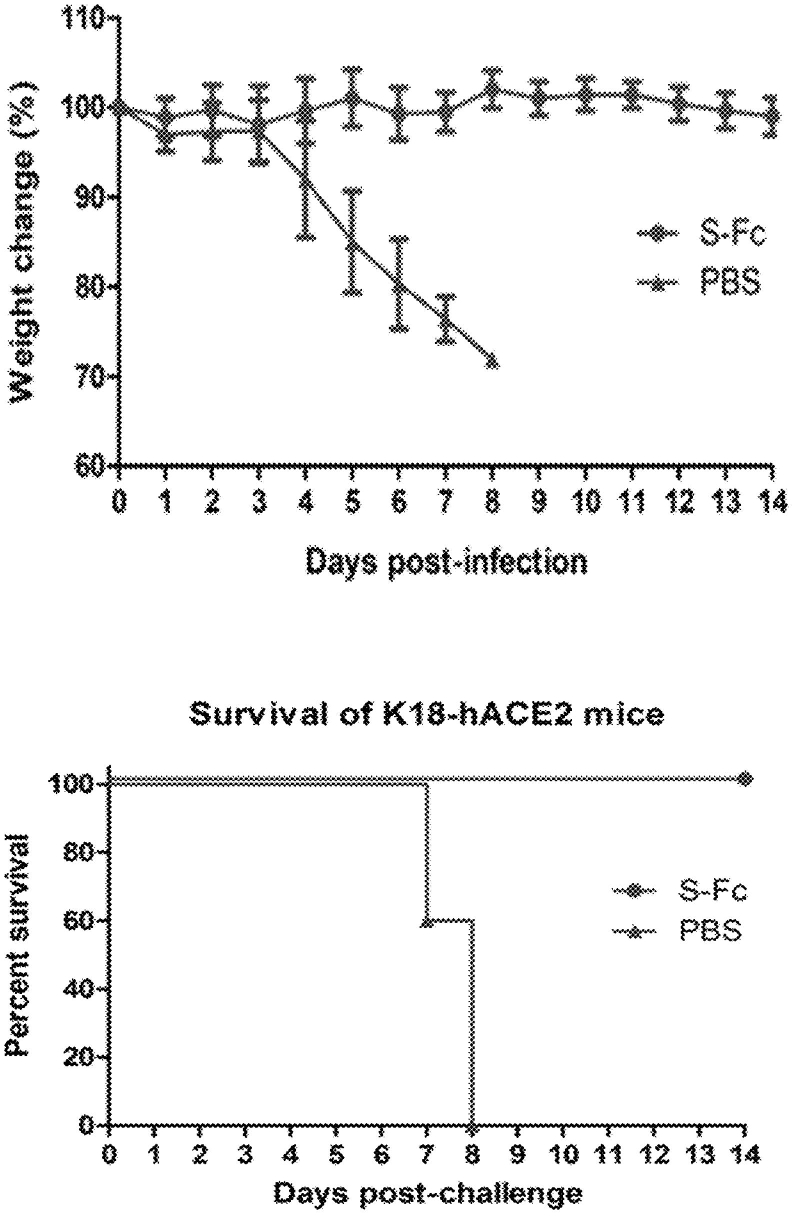
FIG. 6 shows the mean survival following viral challenge. Two weeks after the boost, groups of 5 mice were i.n. challenged with SARS-COV-2 virus and weighed daily for 14 days. Mice were humanely euthanized if above 25% of initial body weight was lost. The percentage of mice from protection after the challenge was shown by the Kaplan-Meier survival curve.
Figure 7:
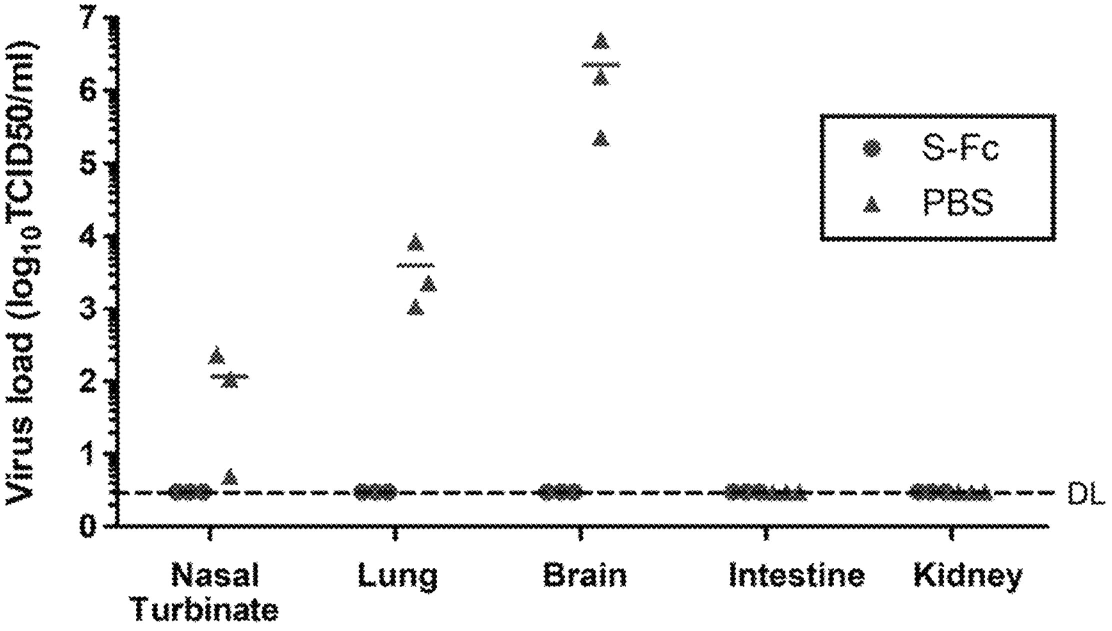
FIG. 7 shows the mean of viral titers following viral challenge. The virus titers in the different organs of the mice (n=3) were determined 5 days after challenge. Supernatants of the tissue homogenates were added onto Vero E6 and incubated for three days. The viral titers were measured by 50% reduction of CPE.
Figure 8:
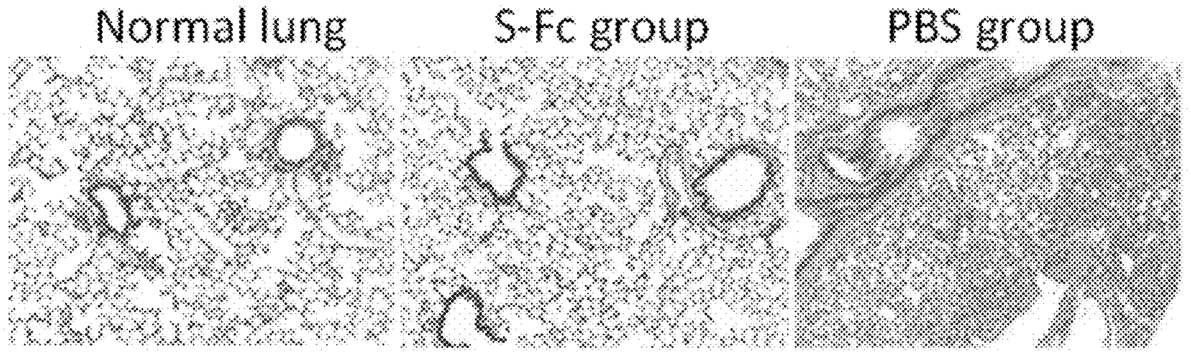
FIG. 8 shows an example of the histopathology of the lungs from the infected or normal mice. Lungs were collected from day 5 post challenge. The sections were stained with H & E to determine the level of inflammation (10×). The representative slides were shown.
Figure 9:
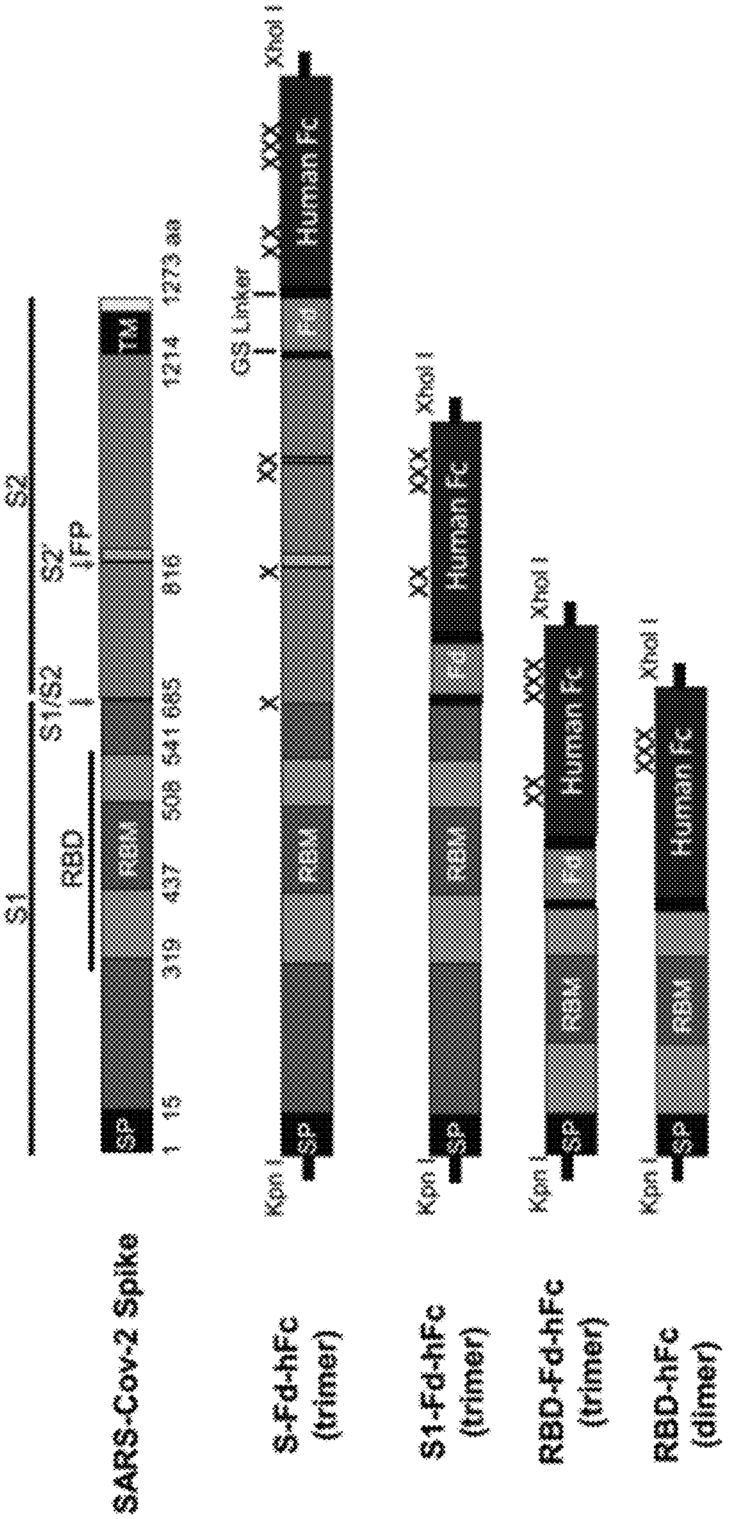
FIG. 9 shows a schematic illustration of the fusion of S, S1, RBD, the foldon, and Fcγ cDNA to create a trimeric S-Fc fusion gene and further includes a RBD-Fc fragment fusion without a trimerization domain. S, Spike; SP, signal peptide; RBD, receptor binding domain; FP, fusion peptide; TM, transmembrane domain. Fd; Foldon domain, cleavage site; R816A, mutation at S2' cleavage site.
Figure 10:
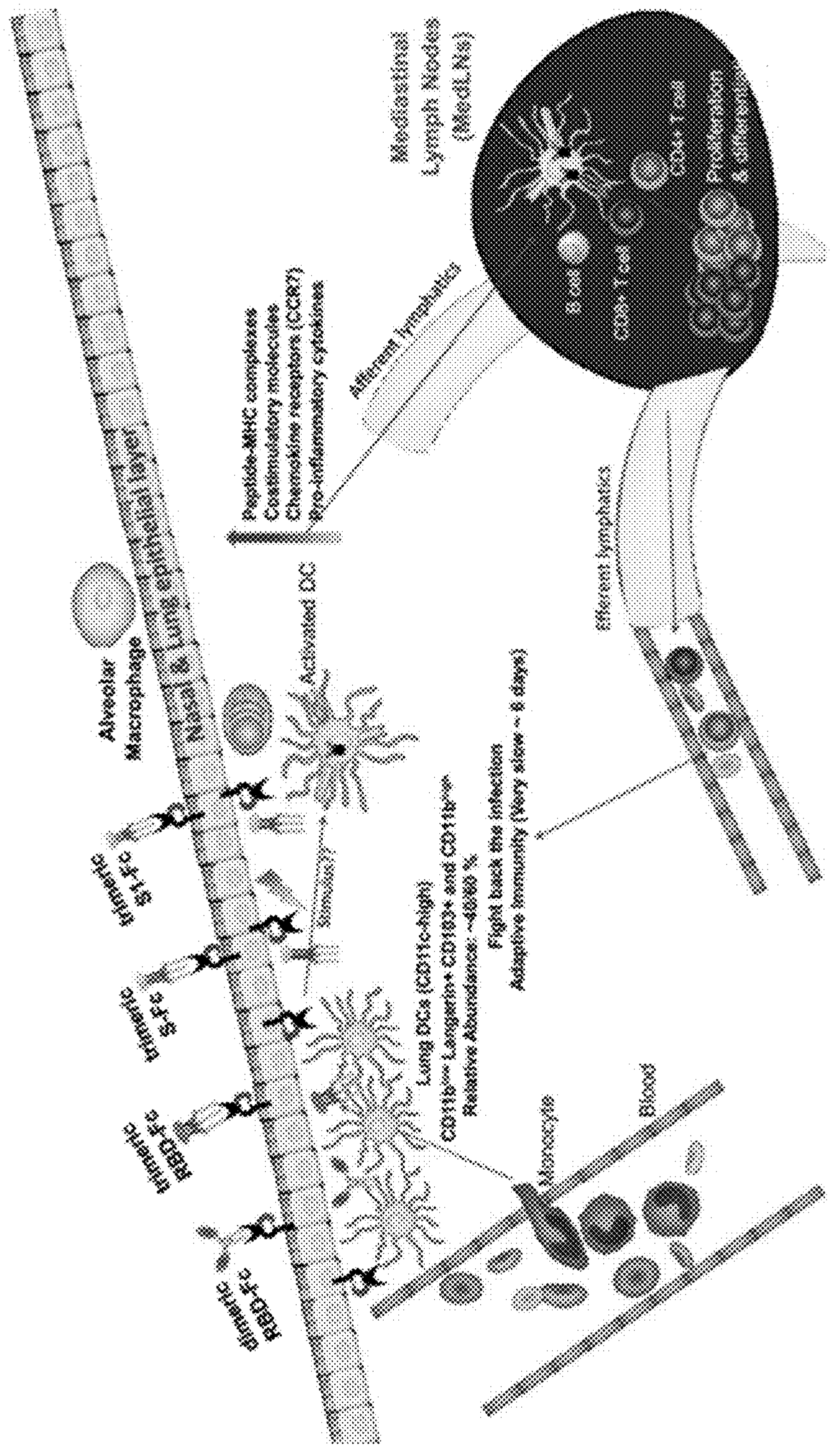
FIG. 10 shows a schematic illustration of an FcRn-mediated delivery of SARS-COV-2 vaccine antigens.

SARS-COV-2 virus infects human ACE2 transgenic mice. To test whether the immune responses elicited by FcRn-targeted intranasal vaccination provide protection, 8-10-week-old human ACE2 transgenic mice were i.n.

immunized intranasally (i.n.) with 10 μg of S-Fc, or PBS in combination with 10 μg CpG, and boosted 2 weeks later with the same dose. The mice were challenged i.n. with a lethal dose ($2.5\times10^4$ TCID50) of SARS-COV-2 virus two weeks after the boost in BSL-3 facility. Mice were monitored and weighed daily for a 14-day period and were euthanized after 25% body weight loss as endpoint. All mice in the PBS groups had weight loss (up to 25%) within 8 days after the challenge and either succumbed to infection or euthanized. In contrast, all the S-Fc-immunized mice had no body-weight loss (FIG. 6, Left). Hence, the trimeric S-Fc protein-immunized mice led to a full protection (FIG. 6, right). Also, virus replicating was assessed in different tissues by 5 days after challenge (FIG. 7). Virus was not detected in tissues, including lung, of trimeric S-Fc-immunized mice. However, different titers of virus were detected in the nasal turbinate, lung, and brain of the PBS group (FIG. 7), indicating these control mice failed to contain viral replication. To further confirm the protection, histopathology was performed and the extent of lung inflammation was determined. The mouse lungs in PBS control mice showed remarkable infiltration of monocytes and lymphocytes after challenge, resulting in high levels of inflammation (FIG. 8, right). In contrast, mice immunized with the trimeric S-Fc/wt protein had significantly lower lung inflammation scores (FIG. 8, middle), which was comparable to the lung structure of uninfected mouse (FIG. 8, left). Overall, the findings show that FcRn-mediated intranasal delivery of the trimeric S-Fc/wt conferred significant protection against lethal SARS-COV-2 virus challenge, resulting in decreased mortality, viral replication, and pulmonary inflammation.

Those skilled in the art will recognize, or be able to ascertain using no more than routine experimentation, many equivalents to the specific embodiments of the method and compositions described herein. Such equivalents are intended to be encompassed by the following claims.

We claim:

1. A peptide comprising a monomeric Fc fragment of an immunoglobulin recognized by a neonatal receptor (FcRn);

a full length soluble SARS-COV-2 spike(S) protein; and a trimerization domain.

2. The peptide of claim 1, wherein the monomeric Fc fragment of an immunoglobulin recognized by a FcRn comprises a mutation in the cysteine residues responsible for dimer formation.

3. The peptide of claim 2, wherein the cysteine residues are at position 11 and 14 of SEQ ID NO:7.

4. The peptide of claim 2, wherein the mutation is a cysteine to serine substitution.

5. The peptide of claim 1, wherein C1q motif has been mutated such that it renders the fragment non-lytic.

6. The peptide of claim 1, wherein the monomeric Fc fragment of an immunoglobulin recognized by a FcRn comprises a CH2 domain and a CH3 domain.

7. The peptide of claim 6, wherein the monomeric Fc fragment of an immunoglobulin recognized by a FcRn comprises one or more mutations in the CH2 domain, wherein the one or more mutations in the CH2 domain ablate C1q binding to the monomeric Fc fragment.

8. The peptide of claim 1, wherein the trimerization domain is a T4 fibritin trimerization domain.

9. The peptide of claim 1, wherein the monomeric Fc fragment is conjugated to the carboxy terminal end of the full length soluble SARS-COV-2 spike protein.

10. A peptide complex comprising three peptides, wherein each of the peptides is the peptide of claim 1.

11. A composition comprising the peptide of claim 1.

12. A composition comprising the peptide complex of claim 10.

13. A method for eliciting a protective immune response against SARS-COV-2 comprising administering to a subject an effective amount of the composition of claim 11.

14. A method for eliciting a protective immune response against SARS-COV-2 comprising administering to a subject an effective amount of a composition comprising a peptide complex, wherein the peptide complex comprises three peptides forming a trimer, wherein each of the three peptides comprises a monomeric Fc fragment of an immunoglobulin recognized by a FcRn; a full length soluble SARS-COV-2 S protein; and a trimerization domain, wherein the administering is to a mucosal epithelium.

15. A method of treating a subject exposed to SARS-COV-2 or at risk of being exposed to SARS-COV-2 comprising administering to the subject an effective amount of the composition of claim 11.

16. A method of treating a subject exposed to SARS-COV-2 or at risk of being exposed to SARS-COV-2 comprising administering to the subject an effective amount of a composition comprising a peptide complex, wherein the peptide complex comprises three peptides forming a trimer, wherein each of the three peptides comprises a monomeric Fc fragment of an immunoglobulin recognized by a FcRn; a full length soluble SARS-COV-2 S protein; and a trimerization domain, wherein the administering is to a mucosal epithelium.

* * * * *